(12) United States Patent
Dineen et al.

(10) Patent No.: US 9,051,311 B2
(45) Date of Patent: Jun. 9, 2015

(54) SULFAMIDE SODIUM CHANNEL INHIBITORS

(71) Applicant: AMGEN INC., Thousand Oaks, CA (US)

(72) Inventors: Thomas Dineen, Somerville, MA (US); Charles Kreiman, Belmont, MA (US); Matthew Weiss, Boston, MA (US); Stephanie Geuns-Meyer, Medford, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/383,880

(22) PCT Filed: Mar. 7, 2013

(86) PCT No.: PCT/US2013/029639
§ 371 (c)(1),
(2) Date: Sep. 8, 2014

(87) PCT Pub. No.: WO2013/134518
PCT Pub. Date: Sep. 12, 2013

(65) Prior Publication Data
US 2015/0018352 A1    Jan. 15, 2015

Related U.S. Application Data

(60) Provisional application No. 61/609,104, filed on Mar. 9, 2012.

(51) Int. Cl.
| | |
|---|---|
| C07D 401/14 | (2006.01) |
| C07D 417/12 | (2006.01) |
| C07D 471/04 | (2006.01) |
| C07D 487/04 | (2006.01) |
| A61K 31/47 | (2006.01) |
| C07D 417/14 | (2006.01) |

(52) U.S. Cl.
CPC ............ *C07D 417/12* (2013.01); *C07D 471/04* (2013.01); *C07D 487/04* (2013.01); *C07D 401/14* (2013.01); *C07D 417/14* (2013.01)

(58) Field of Classification Search
None
See application file for complete search history.

(56) References Cited

U.S. PATENT DOCUMENTS

| | | |
|---|---|---|
| 2008/0200495 A1 | 8/2008 | Boubia et al. |
| 2009/0023716 A1 | 1/2009 | Lijima et al. |
| 2010/0029643 A1 | 2/2010 | Grewal et al. |

FOREIGN PATENT DOCUMENTS

| | | |
|---|---|---|
| RU | 2261246 C1 | 9/2005 |
| WO | 02087513 A2 | 11/2002 |
| WO | 2004/103980 A1 | 12/2004 |
| WO | 2005042537 A1 | 5/2005 |
| WO | 2005066171 A1 | 7/2005 |
| WO | 2006/051662 A1 | 5/2006 |
| WO | 2006119504 A2 | 11/2006 |
| WO | WO 2007016354 A1 | 2/2007 |
| WO | 2009/012241 A1 | 1/2009 |
| WO | 2009011904 A1 | 1/2009 |
| WO | 2010014939 A1 | 2/2010 |
| WO | 2010/026365 A1 | 3/2010 |
| WO | 2010120996 A1 | 10/2010 |
| WO | 2011/137089 A1 | 11/2011 |
| WO | 2013/006596 A1 | 1/2013 |

OTHER PUBLICATIONS

Database Registry [Online] 1,3-5,7, 17,19 Chemical Abstracts Service, Columbus, Ohio, US; Jul. 11, 2006, XP002694732, Database accession No. 891935-81-2 Compounds of the following Registry Nos. 891935-81-2, 891936-13-3, 891936-21-3, 891940-34-4, 891940-42-4, 891944-38-0, 891945-17-8.

Database Registry [Online] 1,3,7, 16-19 Chemical Abstracts Service, Columbus, Ohio, US; Aug. 17, 2006, XP002694733, Database accession No. 902485-35-2 Compound of the following Registry No. 902485-35-2.

Database Registry [Online] 1,3,7, 16-19 Chemical Abstracts Service, Columbus, Ohio, US; Aug. 18, 2006, XP002694734, Database accession No. 902566-77-2 Compound of the following Registry No. 902566-77-2.

Database Registry [Online] 1,3-7, 16,17,19 Chemical Abstracts Service, Columbus, Ohio, US; Aug. 21, 2006, XP002694735, Database accession No. 902885-28-3 Compounds of the following Registry Nos. 902885-28-3, 902885-36-3, 902885-38-5, 902885-40-9, 902886-50-4.

Database Registry [Online] 1,3,6,7, 16,18,19 Chemical Abstracts Service, Columbus, Ohio, US; Apr. 17, 2007, XP002694736, Database accession No. 930524-18-8 Compound of the following Registry No. 930524-18-8.

(Continued)

*Primary Examiner* — Zinna Northington Davis
(74) *Attorney, Agent, or Firm* — Elsa D. Lemoine

(57) ABSTRACT

The present invention provides compounds of Formula I, or pharmaceutically acceptable salts thereof, that are inhibitors of voltage-gated sodium channels, in particular Nav 1.7. The compounds are useful for the treatment of diseases treatable by inhibition of sodium channels such as pain disorders. Also provided are pharmaceutical compositions containing compounds of the present invention.

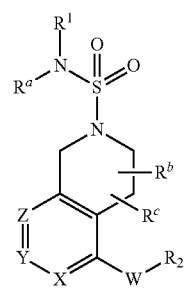

I

20 Claims, No Drawings

(56) References Cited

OTHER PUBLICATIONS

Database Registry [Online] 1,3,4,7, 17-19 Chemical Abstracts Service, Columbus, Ohio, US; Apr. 20, 2007, XP002694737, Database accession No. 931314-73-7 Compound of the following Registry No. 931314-73-7.

Database Registry [Online] 1,3-5,7, 17,19 Chemical Abstracts Service, Columbus, Ohio, US; Apr. 22, 2007, XP002694738, Database accession No. 931703-87-6 Compound of the following Registry No. 931703-87-6.

Database Registry [Online] 1,3,6,8, 16,18,19 Chemical Abstracts Service, Columbus, Ohio, US; Mar. 13, 2008, XP002694740, Database accession No. 1007664-85-8 Compounds of the following Registry Nos. 1007664-85-8, 1007665-10-2.

Database Registry [Online] 1,3-5,7, 17-19 Chemical Abstracts Service, Columbus, Ohio, US; Jun. 22, 2008, XP002694741, Database accession No. 1029777-73-8 Compound of the following Registry No. 1029777-73-8.

Database Registry [Online] 1,3,4,7, 17-19 Chemical Abstracts Service, Columbus, Ohio, US; May 20, 2009, XP002694742, Database accession No. 1147642-90-7 Compound of the following Registry No. 1147642-90-7.

Database Registry [Online] 1,3,6, 16-19 Chemical Abstracts Service, Columbus, Ohio, US; Sep. 15, 2010, XP002694743, Database accession No. 1241200-98-5 Compound of the following Registry No. 1241200-98-5.

Database Registry [Online] 1,3,6,8, 16-19 Chemical Abstracts Service, Columbus, Ohio, US; Sep. 16, 2010, XP002694744, Database accession No. 1241616-76-1 Compound of the following Registry No. 1241616-76-1.

Database Registry [Online] 1,3-6, 16-19 Chemical Abstracts Service, Columbus, Ohio, US; Apr. 14, 2011, XP002694745, Database accession No. 1279855-48-9 Compound of the following Registry No. 1279855-48-9.

Database Registry [Online] 1,3,4,7, 17,19 Chemical Abstracts Service, Columbus, Ohio, US; Feb. 29, 2012, XP002694746, Database accession No. 1358500-50-1 Compound of the following Registry No. 1358500-50-1.

Database Registry [Online] 1,3,4,7, 17,19 Chemical Abstracts Service, Columbus, Ohio, US; Mar. 1, 2012, XP002694747, Database accession No. 1359082-84-0 Compound of the following Registry No. 1359082-84-0.

Database Registry [Online] 1,3,4, 17-19 Chemical Abstracts Service, Columbus, Ohio, US; Jul. 27, 2012, XP002694748, Database accession No. 1384699-84-6 Compound of the following Registry No. 1384699-84-6.

Database Registry [Online] 1,3,4,7, 17-19 Chemical Abstracts Service, Columbus, Ohio, US; Sep. 18, 2012, XP002694749, Database accession No. 1394647-82-5 Compound of the following Registry No. 1394647-82-5.

Valentina Zuliani et al: "Sodium channel blockers for neuropathic pain", Expert Opinion on Therapeutic Patents, Informa Healthcare, GB, vol. 20, No. 6, Jun. 2010, pp. 755-779, XP009152755, I SSN: 1354-3776.

SciFinder®—Bioorganic & Medicinal Chemistry Letters, vol. 19, Issue: 22, pp. 6452-6458, Journal, 2009, CODEN: BMCLE8, ISSN:0960-894X, DOI: 10.1016/j.bmcl.2009.09.027.

SULFAMIDE SODIUM CHANNEL INHIBITORS

RELATED APPLICATIONS

This application is a national stage application under 35 U.S.C. §371 of International Application No. PCT/US2013/029639, having an international filing date of Mar. 7, 2013, which claims the benefit of, and priority to, U.S. Provisional Patent Application No. 61/609,114, filed Mar. 9, 2012, which is hereby incorporated herein by reference in its entirety.

FIELD OF THE INVENTION

The present invention provides compounds that are inhibitors of voltage-gated sodium channels (Nay), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., 3$^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001;
Wood, J. N. and, Boorman, J. "Voltage-gated sodium channel blockers; target validation and therapeutic potential," *Curr. Top Med. Chem.* 5:529-537, 2005). Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway.

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," *J. Med. Genet.* 41:171-174, 2004; Drenth J. P. H., to Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception. Accordingly, a therapeutic agent that inhibits Nav 1.7 should effectively treat pain in humans. The present invention provides compounds that are inhibitors of Nav 1.7.

SUMMARY OF THE INVENTION

In embodiment 1, the present invention provides compounds of Formula I, or pharmaceutically acceptable salts thereof,

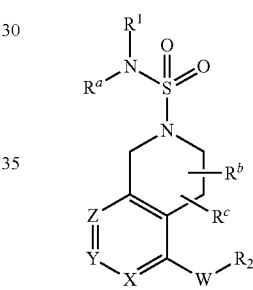

I wherein:
$R^1$ is a five to six membered heteroaryl group, where the heteroaryl group can have from one to three heteroatoms independently selected from O, N or S, and can be unsubstituted or substituted with from 1 to 3 substituents independently selected from halo, $C_{1-6}$alkyl,
—CN, —CF$_3$, —OH, —OCF$_3$, —OC$_{1-6}$alkyl, —CO$_2$R$^e$ or —(CH$_2$)$_n$NR$^e$R$^e$;
$R^2$ is a three to ten membered cycloalkyl, six to ten membered aryl, five to ten membered heteroaryl or three to ten membered heterocycloalkyl group, where the heteroaryl or heterocycloalkyl group can have from one to three heteroatoms independently selected from O, N or S, and where the cycloalkyl, aryl, heteroaryl or heterocycloalkyl group can be unsubstituted or substituted with from 1 to 3 substituents independently selected from an A group, halo, —N$_3$, —CF$_3$, —OH, —OCF$_3$, $C_{1-6}$alkyl,
—OC$_{1-6}$alkyl, —CN, —(CH$_2$)$_n$NR$^e$R$^e$, —O(CH$_2$)$_m$OR$^e$, —CO$_2$R$^e$, —SR$^e$, —S(=O)$_2$R$^e$ or —NR$^e$(CH$_2$)$_m$OR$^e$;
A is a three to ten membered cycloalkyl, six to ten membered aryl, five to ten membered heteroaryl or three to ten membered heterocycloalkyl group, where the heteroaryl or heterocycloalkyl group can have from one to three heteroatoms independently selected from O, N or S, and where the cycloalkyl, aryl, heteroaryl or heterocycloalkyl group can be unsubstituted or substituted with from 1 to 3 substituents independently selected from halo, $C_{1-6}$alkyl, —CN, —CF$_3$, —OH, —OCF$_3$, —OC$_{1-6}$alkyl, —CO$_2$R$^e$ or —(CH$_2$)$_n$NR$^e$R$^e$;

R$^a$ is hydrogen, $C_{1-6}$alkyl or a three to ten membered cycloalkyl group, where the cycloalkyl group may be unsubstituted or substituted with from 1 to 3 substituents independently selected from halo, $C_{1-6}$alkyl, —CN, —CF$_3$, —OH, —OCF$_3$, —CO$_2$R$^e$ or —OC$_{1-6}$alkyl;

R$^b$ is hydrogen, halo, —CN, —OC$_{1-6}$alkyl, $C_{1-6}$alkyl, —CF$_3$, —OH, —CF$_2$H, —OCF$_3$, —OCF$_2$H, —CO$_2$R$^e$, —(=O) or —OCFH$_2$;

R$^c$ is hydrogen, halo, —CN, —OC$_{1-6}$alkyl, $C_{1-6}$alkyl, —CF$_3$, —OH, —CF$_2$H, —OCF$_3$, —OCF$_2$H, —CO$_2$R$^e$ or —OCFH$_2$;

W is a bond, O, N(H) or CH$_2$,

X is CR$^d$ or N;

Y is CR$^d$ or N;

Z is CR$^d$ or N;

each R$^d$ is independently selected from hydrogen, halo, —CN, —OC$_{1-6}$alkyl, $C_{1-6}$alkyl, —CF$_3$, —OH, —CF$_2$H, —OCF$_3$, —OCF$_2$H, —CO$_2$R$^e$ or —OCFH$_2$;

each n is independently 0 to 3;

each m is independently 1 to 3; and each R$^e$ is independently hydrogen or $C_{1-6}$alkyl, provided that the compound of Formula I is not
5-(2-(1,2,3,6-tetrahydropyridin-4-yl)-4-(trifluoromethyl)phenyl)-N-(1,3,4-thiadiazol-2-yl)-3,4-dihydroisoquinoline-2(1H)-sulfonamide or
5-(1,2,3,6-tetrahydropyridin-4-yl)-N-(1,2,4-thiadiazol-5-yl)-3,4-dihydroisoquinoline-2(1H)-sulfonamide.

In embodiment 2, the present invention provides compounds in accordance with embodiment 1, or pharmaceutically acceptable salts thereof, wherein R$^1$ is a five or six membered substituted or unsubstituted heteroaryl group.

In embodiment 3, the present invention provides compounds in accordance with embodiment 1, or pharmaceutically acceptable salts thereof, wherein R$^1$ is a five membered substituted or unsubstituted heteroaryl group.

In embodiment 4, the present invention provides compounds in accordance with embodiment 1, or pharmaceutically acceptable salts thereof, wherein R$^1$ is a six membered substituted or unsubstituted heteroaryl group.

In embodiment 5, the present invention provides compounds in accordance with embodiment 1, or pharmaceutically acceptable salts thereof, wherein R$^1$ is selected from substituted or unsubstituted thiadiazolyl, thiazolyl, pyrimidinyl or pyrazinyl.

In embodiment 6, the present invention provides compounds in accordance with embodiment 1, or pharmaceutically acceptable salts thereof, wherein R$^1$ is selected from substituted or unsubstituted thiadiazolyl.

In embodiment 7, the present invention provides compounds in accordance with any one of embodiments 1 to 6, or pharmaceutically acceptable salts thereof, wherein R$^a$ is hydrogen.

In embodiment 8, the present invention provides compounds in accordance with any one of embodiments 1 to 6, or pharmaceutically acceptable salts thereof, wherein R$^a$ is $C_{1-6}$alkyl.

In embodiment 9, the present invention provides compounds in accordance with any one of embodiments 1 to 8, or pharmaceutically acceptable salts thereof, wherein R$^b$ is hydrogen.

In embodiment 10, the present invention provides compounds in accordance with any one of embodiments 1 to 9, or pharmaceutically acceptable salts thereof, wherein R$^c$ is hydrogen.

In embodiment 11, the present invention provides compounds in accordance with any one of embodiments 1 to 10, or pharmaceutically acceptable salts thereof, wherein X is CH.

In embodiment 12, the present invention provides compounds in accordance with any one of embodiments 1 to 10, or pharmaceutically acceptable salts thereof, wherein X is N.

In embodiment 13, the present invention provides compounds accordance with any one of embodiments 1 to 12, or pharmaceutically acceptable salts thereof, wherein Y is CH.

In embodiment 14, the present invention provides compounds in accordance with any one of embodiments 1 to 12, or pharmaceutically acceptable salts thereof, wherein Y is N.

In embodiment 15, the present invention provides compounds in accordance with any one of embodiments 1 to 14, or pharmaceutically acceptable salts thereof, wherein Z is CH.

In embodiment 16, the present invention provides compounds in accordance with any one of embodiments 1 to 14, or pharmaceutically acceptable salts thereof, wherein Z is N.

In embodiment 17, the present invention provides compounds in accordance with any one of embodiments 1 to 10, or pharmaceutically acceptable salts thereof, wherein X, Y and Z are CH.

In embodiment 18, the present invention provides compounds in accordance with any one of embodiments 1 to 10, or pharmaceutically acceptable salts thereof, wherein X is N, and Y and Z are CH.

In embodiment 19, the present invention provides compounds in accordance with any one of embodiments 1 to 18, or pharmaceutically acceptable salts thereof, wherein R$^2$ is a six to ten membered aryl group, six to ten membered heterocycloalkyl group or five to ten membered heteroaryl group, which group can be substituted or unsubstituted.

In embodiment 20, the present invention provides compounds in accordance with any one of embodiments 1 to 18, or pharmaceutically acceptable salts thereof, wherein R$^2$ is a substituted or unsubstituted six membered aryl group.

In embodiment 21, the present invention provides compounds in accordance with any one of embodiments 1 to 18, or pharmaceutically acceptable salts thereof, wherein R$^2$ is substituted or unsubstituted phenyl.

In embodiment 22, the present invention provides compounds in accordance with any one of embodiments 1 to 18, or pharmaceutically acceptable salts thereof, wherein R$^2$ is phenyl substituted with from 1 to 3 substituents independently selected from an A group, halo, —N$_3$, —CF$_3$, —OH, —OCF$_3$, $C_{1-6}$alkyl, —OC$_{1-6}$alkyl, —CN, —(CH$_2$)$_n$NR$^e$R$^e$, —O(CH$_2$)$_m$OR$^e$, —CO$_2$R$^e$, —SR$^e$, —S(=O)$_2$R$^e$ or —NR$^e$(CH$_2$)$_m$OR$^e$.

In embodiment 23, the present invention provides compounds in accordance with any one of embodiments 1 to 18, or pharmaceutically acceptable salts thereof, wherein R$^2$ is selected from phenyl, tetrahydroisoquinolinyl, isoquinolinyl, naphthalenyl, quinolinyl, indazolyl, pyridyl or dihydropyridyl, which can be substituted or unsubstituted.

In embodiment 24, the present invention provides compounds in accordance with any one of embodiments 1 to 18, or pharmaceutically acceptable salts thereof, wherein R$^2$ is selected from phenyl, tetrahydroisoquinolinyl, isoquinolinyl, naphthalenyl, quinolinyl, indazolyl, pyridyl or dihydropyridyl substituted with from one to three substituents independently selected from an A group or substituted A group, halo, —CF$_3$, —OC$_{1-6}$alkyl, cyclopropyl, or —CO$_2$C$_{1-6}$alkyl.

In embodiment 25, the present invention provides compounds in accordance with any one of embodiments 1 to 18, or pharmaceutically acceptable salts thereof, wherein R$^2$

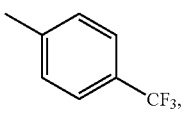

which can have up to two additional substitutents.

In embodiment 26, the present invention provides compounds in accordance with any one of embodiments 1 to 18, or pharmaceutically acceptable salts thereof, wherein $R^2$ is

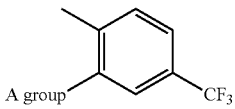

and the A group can be substituted or unsubstituted.

In embodiment 27, the present invention provides compounds in accordance with any one of embodiments 1 to 18, or pharmaceutically acceptable salts thereof, wherein $R^2$

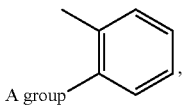

which can have up to two additional substitutents, and the A group can be substituted or unsubstituted.

In embodiment 28, the present invention provides compounds in accordance with any one of embodiments 1 to 18, or pharmaceutically acceptable salts thereof, wherein $R^2$ is phenyl substituted with at least one A group selected from unsubstituted or substituted pyrazolyl, pyridyl, dihydropyridyl, dihydropyranyl, pyrimidinyl, morpholinyl, imidazolyl, dihydropyrrolyl, tetrahydropyridyl, piperazinyl or piperadinyl, and from 0 to 2 additional substituents.

In embodiment 29, the present invention provides compounds in accordance with any one of embodiments 1 to 28, or pharmaceutically acceptable salts thereof, wherein W is a bond.

In embodiment 30, the present invention provides compounds, or pharmaceutically acceptable salts thereof, selected from:
5-(2-(1-methyl-1H-pyrazol-5-yl)-4-(trifluoromethyl)phenyl)-N-(1,2,4-thiadiazol-5-yl)-3,4-dihydroisoquinoline-2(1H)-sulfonamide;
5-(2-(pyridin-4-yl)-4-(trifluoromethyl)phenyl)-N-(1,2,4-thiadiazol-5-yl)-3,4-dihydroisoquinoline-2(1H)-sulfonamide;
5-(2-bromo-4-(trifluoromethyl)phenyl)-N-(thiazol-2-yl)-3,4-dihydroisoquinoline-2(1H)-sulfonamide;
5-(2-bromo-4-(trifluoromethyl)phenyl)-N-(1,2,4-thiadiazol-5-yl)-3,4-dihydroisoquinoline-2(1H)-sulfonamide;
tert-butyl 4-(2-(2-(N-(1,2,4-thiadiazol-5-yl)sulfamoyl)-1,2,3,4-tetrahydroisoquinolin-5-yl)-5-(trifluoromethyl)phenyl)-5,6-dihydropyridine-1(2H)-carboxylate;
5-(2-(1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide;
N-(1,2,4-thiadiazol-5-yl)-5-(4-(trifluoromethyl)phenyl)-3,4-dihydroisoquinoline-2(1H)-sulfonamide;
5-(2-fluoro-4-(trifluoromethyl)phenyl)-N-(1,2,4-thiadiazol-5-yl)-3,4-dihydroisoquinoline-2(1H)-sulfonamide;
5-(2-chloro-4-(trifluoromethyl)phenyl)-N-(1,2,4-thiadiazol-5-yl)-3,4-dihydroisoquinoline-2(1H)-sulfonamide;
5-(2-chloro-4-(trifluoromethyl)phenyl)-N-(1,2,4-thiadiazol-5-yl)-3,4-dihydroisoquinoline-2(1H)-sulfonamide;
5-(4-chloro-2-fluorophenyl)-N-(1,2,4-thiadiazol-5-yl)-3,4-dihydroisoquinoline-2(1H)-sulfonamide;
5-(2,4-dichlorophenyl)-N-(1,2,4-thiadiazol-5-yl)-3,4-dihydroisoquinoline-2(1H)-sulfonamide;
N-(1,2,4-thiadiazol-5-yl)-1',2',3,3',4,4'-hexahydro-[5,5'-biisoquinoline]-2(1H)-sulfonamide;
4-(2-(2-(N-(1,2,4-thiadiazol-5-yl)sulfamoyl)-1,2,3,4-tetrahydroisoquinolin-5-yl)-5-(trifluoromethyl)phenyl)-1,1-dimethyl-1,2,3,6-tetrahydropyridin-1-ium hydroxide;
5-(2-(1-methyl-1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide;
5-(2-(1-methyl-1H-pyrazol-4-yl)-4-(trifluoromethyl)phenyl)-N-(1,2,4-thiadiazol-5-yl)-3,4-dihydroisoquinoline-2(1H)-sulfonamide;
5-(2-(1H-pyrazol-4-yl)-4-(trifluoromethyl)phenyl)-N-(1,2,4-thiadiazol-5-yl)-3,4-dihydroisoquinoline-2(1H)-sulfonamide;
5-(2-(2-aminopyridin-4-yl)-4-(trifluoromethyl)phenyl)-N-(1,2,4-thiadiazol-5-yl)-3,4-dihydroisoquinoline-2(1H)-sulfonamide;
5-(2-(3,6-dihydro-2H-pyran-4-yl)-4-(trifluoromethyl)phenyl)-N-(1,2,4-thiadiazol-5-yl)-3,4-dihydroisoquinoline-2(1H)-sulfonamide;
5-(2-(5-methoxypyridin-3-yl)-4-(trifluoromethyl)phenyl)-N-(1,2,4-thiadiazol-5-yl)-3,4-dihydroisoquinoline-2(1H)-sulfonamide;
5-(2-(5-methylpyridin-3-yl)-4-(trifluoromethyl)phenyl)-N-(1,2,4-thiadiazol-5-yl)-3,4-dihydroisoquinoline-2(1H)-sulfonamide;
5-(2-(pyridin-3-yl)-4-(trifluoromethyl)phenyl)-N-(1,2,4-thiadiazol-5-yl)-3,4-dihydroisoquinoline-2(1H)-sulfonamide;
5-(2-(pyrimidin-5-yl)-4-(trifluoromethyl)phenyl)-N-(1,2,4-thiadiazol-5-yl)-3,4-dihydroisoquinoline-2(1H)-sulfonamide;
5-(naphthalen-1-yl)-N-(1,2,4-thiadiazol-5-yl)-3,4-dihydroisoquinoline-2(1H)-sulfonamide;
N-(1,2,4-thiadiazol-5-yl)-3',4'-dihydro-[4,5'-biisoquinoline]-2'(1'H)-sulfonamide;
5-(2,4-dimethoxyphenyl)-N-(1,2,4-thiadiazol-5-yl)-3,4-dihydroisoquinoline-2(1H)-sulfonamide;
5-(2,5-dimethoxyphenyl)-N-(1,2,4-thiadiazol-5-yl)-3,4-dihydroisoquinoline-2(1H)-sulfonamide;
5-(2,6-dimethoxyphenyl)-N-(1,2,4-thiadiazol-5-yl)-3,4-dihydroisoquinoline-2(1H)-sulfonamide;
5-(5-fluoro-2-methoxyphenyl)-N-(1,2,4-thiadiazol-5-yl)-3,4-dihydroisoquinoline-2(1H)-sulfonamide;
5-(4-fluoro-2-methoxyphenyl)-N-(1,2,4-thiadiazol-5-yl)-3,4-dihydroisoquinoline-2(1H)-sulfonamide;
5-(2-morpholino-4-(trifluoromethyl)phenyl)-N-(1,2,4-thiadiazol-5-yl)-3,4-dihydroisoquinoline-2(1H)-sulfonamide;
5-(2-(1H-imidazol-1-yl)-4-(trifluoromethyl)phenyl)-N-(1,2,4-thiadiazol-5-yl)-3,4-dihydroisoquinoline-2(1H)-sulfonamide;
N-(5-fluorothiazol-2-yl)-5-(2-(1,2,3,6-tetrahydropyridin-4-yl)-4-(trifluoromethyl)phenyl)-3,4-dihydroisoquinoline-2(1H)-sulfonamide;
5-(2-(2,5-dihydro-1H-pyrrol-3-yl)-4-(trifluoromethyl)phenyl)-N-(1,2,4-thiadiazol-5-yl)-3,4-dihydroisoquinoline-2(1H)-sulfonamide;

N-(5-fluorothiazol-2-yl)-5-(2-(piperidin-4-yl)-4-(trifluoromethyl)phenyl)-3,4-dihydroisoquinoline-2(1H)-sulfonamide;

5-(2-(1,2,3,6-tetrahydropyridin-4-yl)-4-(trifluoromethyl)phenyl)-N-(thiazol-2-yl)-3,4-dihydroisoquinoline-2(1H)-sulfonamide;

N-(pyrimidin-4-yl)-5-(2-(1,2,3,6-tetrahydropyridin-4-yl)-4-(trifluoromethyl)phenyl)-3,4-dihydroisoquinoline-2(1H)-sulfonamide;

5-(2-(1H-imidazol-1-yl)-4-(trifluoromethyl)phenyl)-N-(5-fluorothiazol-2-yl)-3,4-dihydroisoquinoline-2(1H)-sulfonamide;

N-(5-fluorothiazol-2-yl)-5-(2-(1-methyl-1,2,3,6-tetrahydropyridin-4-yl)-4-(trifluoromethyl)phenyl)-3,4-dihydroisoquinoline-2(1H)-sulfonamide;

N-(5-fluorothiazol-2-yl)-5-(2-(1-methyl-1,2,3,6-tetrahydropyridin-4-yl)-5-(trifluoromethyl)phenyl)-3,4-dihydroisoquinoline-2(1H)-sulfonamide;

N-(5-fluorothiazol-2-yl)-5-(2-(4-methylpiperazin-1-yl)-4-(trifluoromethyl)phenyl)-3,4-dihydroisoquinoline-2(1H)-sulfonamide;

N-(5-fluorothiazol-2-yl)-5-(2-(4-methylpiperazin-1-yl)-4-(trifluoromethyl)phenyl)-3,4-dihydroisoquinoline-2(1H)-sulfonamide;

N-(5-fluorothiazol-2-yl)-5-(2-(5-methyl-1H-imidazol-1-yl)-4-(trifluoromethyl)phenyl)-3,4-dihydroisoquinoline-2(1H)-sulfonamide;

5-(2-methoxy-4-(trifluoromethyl)phenyl)-N-(1,2,4-thiadiazol-5-yl)-3,4-dihydroisoquinoline-2(1H)-sulfonamide;

5-(4-cyclopropyl-2-methoxyphenyl)-N-(1,2,4-thiadiazol-5-yl)-3,4-dihydroisoquinoline-2(1H)-sulfonamide;

5-(2-methoxy-4-(trifluoromethyl)phenyl)-N-(1,2,4-thiadiazol-5-yl)-3,4-dihydro-2,6-naphthyridine-2(1H)-sulfonamide;

5-(4-cyclopropyl-2-methoxyphenyl)-N-(1,2,4-thiadiazol-5-yl)-3,4-dihydro-2,6-naphthyridine-2(1H)-sulfonamide;

5-(2-methoxy-4-(trifluoromethyl)phenyl)-4-methyl-N-(1,2,4-thiadiazol-5-yl)-3,4-dihydroisoquinoline-2(1H)-sulfonamide;

5-(2-(1-methyl-1H-pyrazol-5-yl)-4-(trifluoromethyl)phenyl)-N-(pyrimidin-2-yl)-3,4-dihydroisoquinoline-2(1H)-sulfonamide;

5-(2-methoxypyridin-3-yl)-N-(1,2,4-thiadiazol-5-yl)-3,4-dihydroisoquinoline-2(1H)-sulfonamide;

5-(1H-indazol-4-yl)-N-(1,2,4-thiadiazol-5-yl)-3,4-dihydroisoquinoline-2(1H)-sulfonamide;

7-chloro-N-(1,2,4-thiadiazol-5-yl)-3',4'-dihydro-[4,5'-biisoquinoline]-2'(1'H)-sulfonamide;

N-(pyrazin-2-yl)-5-(2-(1,2,3,6-tetrahydropyridin-4-yl)-4-(trifluoromethyl)phenyl)-3,4-dihydroisoquinoline-2(1H)-sulfonamide;

5-(4-chloro-2-fluoro-6-(1-methyl-1,2,3,6-tetrahydropyridin-4-yl)phenyl)-N-(5-fluorothiazol-2-yl)-3,4-dihydroisoquinoline-2(1H)-sulfonamide;

8-(2-methoxy-4-(trifluoromethyl)phenyl)-N-(1,2,4-thiadiazol-5-yl)-3,4-dihydroisoquinoline-2(1H)-sulfonamide;

5-(2-bromo-4-(trifluoromethyl)phenyl)-N-(pyrimidin-4-yl)-3,4-dihydroisoquinoline-2(1H)-sulfonamide;

tert-butyl 4-(2-(N-(1,2,4-thiadiazol-5-yl)sulfamoyl)-1,2,3,4-tetrahydroisoquinolin-5-yl)-5,6-dihydropyridine-1(2H)-carboxylate;

tert-butyl 2'-(N-(1,2,4-thiadiazol-5-yl)sulfamoyl)-1',2',3,3',4,4'-hexahydro-[5,5'-biisoquinoline]-2(1H)-carboxylate;

4-(2-methoxy-4-(trifluoromethyl)phenyl)-N-1,3-thiazol-2-yl-5,8-dihydropyrido[3,4-d]pyrimidine-7(6H)-sulfonamide;

N-(5-fluoro-1,3-thiazol-2-yl)-4-(2-methoxy-4-(trifluoromethyl)phenyl)-5,8-dihydropyrido[3,4-d]pyrimidine-7(6H)-sulfonamide;

4-(2-methoxy-4-(trifluoromethyl)phenyl)-N-1,2,4-thiadiazol-5-yl-5,8-dihydropyrido[3,4-d]pyrimidine-7(6H)-sulfonamide;

5-(3',4'-difluoro-3-methoxy-4-biphenylyl)-N-1,3,4-thiadiazol-2-yl-3,4-dihydro-2(1H)-isoquinolinesulfonamide;

5-(3',4'-difluoro-4-methoxy-3-biphenylyl)-N-1,3,4-thiadiazol-2-yl-3,4-dihydro-2(1H)-isoquinolinesulfonamide, or 4-(2-methoxy-4-(trifluoromethyl)phenyl)-N-4-pyrimidinyl-5,8-dihydro-1,7-naphthyridine-7(6H)-sulfonamide.

In embodiment 31, the present invention provides methods of treating pain, the methods comprising administering to a patient in need thereof a therapeutically effective amount of a compound in accordance with any one of embodiments 1 to 30, or a pharmaceutically acceptable salt thereof.

In embodiment 32, the present invention provides methods in accordance with embodiment 31 wherein the treatment is for chronic pain, acute pain, neuropathic pain, pain associated with rheumatoid arthritis, pain associated with osteoarthritis or pain associated with cancer.

In embodiment 33, the present invention provides pharmaceutical compositions comprising a compound in accordance with any one of embodiments 1 to 30, or pharmaceutically acceptable salts thereof, and a pharmaceutically acceptable excipient.

DETAILED DESCRIPTION OF THE INVENTION

The present invention provides compounds of Formula I, as defined above, or pharmaceutically acceptable salts thereof. The present invention also provides pharmaceutical compositions comprising a compound of Formula I, or pharmaceutically acceptable salts thereof, and methods of treating diseases and/or conditions, such as pain, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups. A cycloalkyl group can also be a bicyclic group comprising a cycloalkyl ring fused to an aryl or heteroaryl ring. An example of such a fused bicyclic group is tetrahydronapthalene.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heteroatoms are particularly common. A heterocycloalkyl group can also be a bicyclic group comprising a heterocycloalkyl ring fused to an aryl or heteroaryl ring. Examples of such fused bicyclic ring include tetrahydroquinoline or tetrahydroisoquinoline.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4oxadiazolyl, 1,2,3-triazolyl, 1,2,4-triazolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J. Mol. Cell Cardiol.* 42(3): 469-477, 2007), schizophrenia, neuroprotection after stroke, drug and alcohol abuse (Johannessen L. C., *CNS Drugs* 22(1) 27-47, 2008), Alzheimer's (Kim D. Y., et. al., *Nat. Cell. Biol.* 9(7):755-764, 2007), and cancer (Gillet L., et. al., *J Biol Chem* 2009, Jan. 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may also be used to treat obesity and facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$—$Cl_2$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$)alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Another example of tautomerism is as follows:

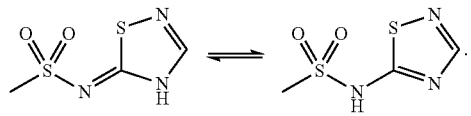

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity can be measured using high performance liquid chromatography (HPLC) system with UV detection at 254 nm and 215 nm (System A: Agilent Zorbax Eclipse XDB-C8 4.6×150 mm, 5 μm, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, Calif.). Silica gel chromatography was generally performed with prepacked silica gel cartridges (Biotage, Uppsala, Sweden or Teledyne-Isco, Lincoln, Nebr.). $^1H$ NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons.

Low-resolution mass spectral (MS) data were determined on an Agilent 1100 Series (Agilent Technologies, Santa Clara, Calif.) LCMS with UV detection at 254 nm and 215 nm and a low resonance electrospray mode (ESI).

The following abbreviations may be used herein:
AmPhos 4-(di-tert-butylphosphino)-N,N-dimethylaniline
AcCl acetyl chloride
ACN acetonitrile
AcOH acetic acid
aq or aq. aqueous
BOC or Boc tert-butyloxycarbonyl
Bn benzyl
DBU 1,8-diazabicyclo[5.4.0]undec-7-ene
DCM dichloromethane
DIPEA N,N-diisopropylethylamine
DMAP 4-dimethylaminopyridine
DMB dimethoxybenzyl
DME dimethoxyethane
DMF N,N-dimethylformamide
DMSO dimethyl sulfoxide
Dppf, DPPF or dppf 1,1'-bis(diphenylphosphino)ferrocene
ESI or ES electrospray ionization
Et ethyl
Et$_2$O diethyl ether
Et$_3$N triethylamine
EtOAc ethyl acetate
eq or eq. equivalent
g grams
h hour
HPLC high pressure liquid chromatography
iPr isopropyl
iPr$_2$NEt N-ethyl diisopropylamine (Hunig's base)
KOAc potassium acetate
LC MS, LCMS, LC-MS or LC/MS liquid chromatography mass spectroscopy
LHMDS or LiHMDS lithium hexamethyldisilazide
m/z mass divided by charge
Me methyl
MeOH methanol
MeCN or ACN acetonitrile
mg milligrams
min minutes
mL milliliters
MPLC medium pressure liquid chromatography
MS mass spectra
NBS N-bromosuccinimide
NCS N-chlorosuccinimide
n-BuLi n-butyllithium
NMR nuclear magnetic resonance
Pd$_2$(dba)$_3$ tris(dibenzylideneacetone)dipalladium(0)
Pd(AmPhos)$_2$Cl$_2$ Bis(di-tert-butyl(4-dimethylaminophenyl)phosphine)dichloropalladium (II)
Ph phenyl
PMB p-methoxybenzyl
RT or rt room temperature
SEM 2-(trimethylsilyl)ethoxymethyl
SFC supercritical fluid chromatography
TBAF tetra-n-butylammonium fluoride
t-BuOH tert-butanol
TEA triethylamine
TIPS-Cl triisopropylsilyl chloride
TFA trifluoroacetic acid
THF tetrahydrofuran
UV ultraviolet
xantphos 4,5-bis(diphenylphosphino)-9,9-dimethylxanthine
X-Phos 2-dicyclohexylphosphino-2',4',6'-triisopropyl-1,1'-biphenyl

EXAMPLES

General Synthetic Schemes

Scheme 1:

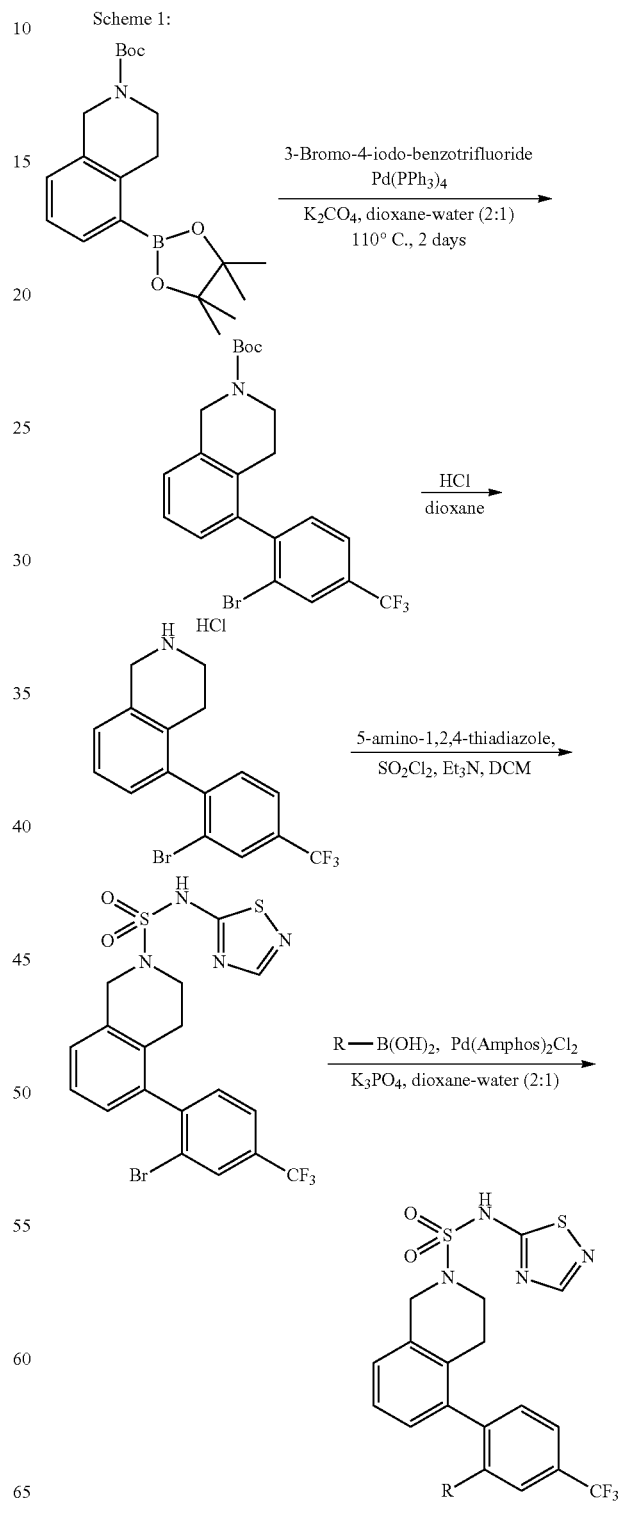

The Suzuki reaction with a suitably protected tetrahydroisoquinoline boronate can be achieved using a variety of bases (such as Cs$_2$CO$_3$, K$_2$CO$_3$, K$_3$PO$_4$ or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). The removal of the tert-butoxycarbonyl protecting group can be accomplished under a number of conditions, including: AcCl in methanol (to generate HCl in situ), neat TFA, a solution of TFA in DCM, or a solution of 4N HCl in 1,4-dioxane. Installation of the heterocyclic sulfamide moiety can be accomplished by treatment with 5-amino-1,2,4-thiadiazole, sulfuryl chloride and TEA or an alternative method with various methods described in Schemes 9 to 12. Further Suzuki reaction with the pentultimate tetrahydroisoquinoline sulfamide bromide can be achieved using a variety of bases (such as Cs$_2$CO$_3$, K$_2$CO$_3$, K$_3$PO$_4$ or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF, or t-BuOH).

Scheme 2:

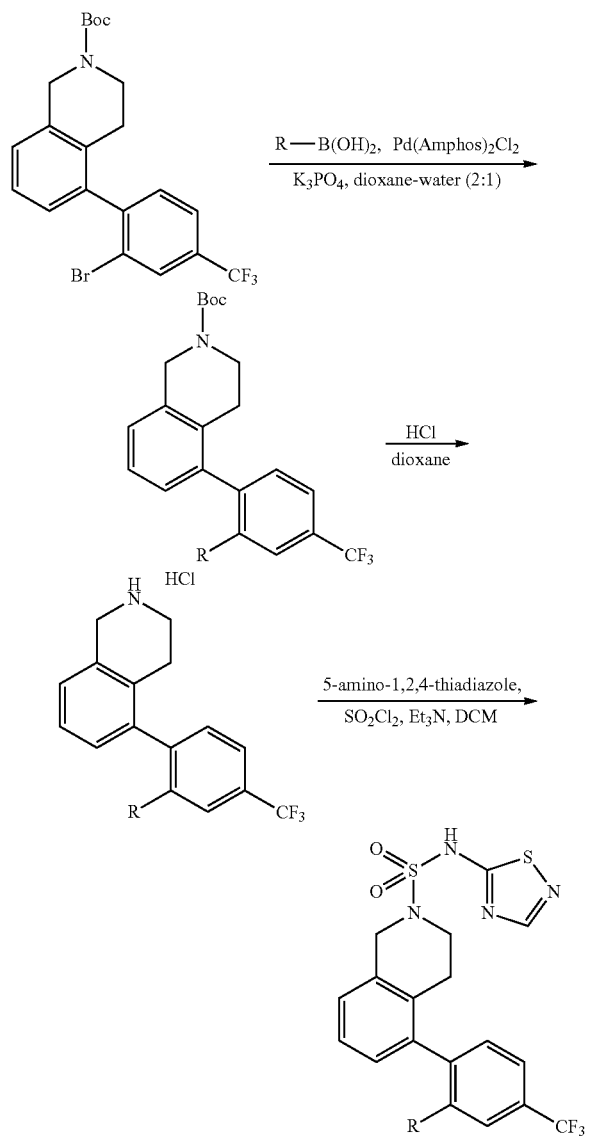

The Suzuki reaction with the protected tetrahydroisoquinoline bromide can be achieved using a variety of bases (such as Cs$_2$CO$_3$, K$_2$CO$_3$, K$_3$PO$_4$ or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). The removal of the tert-butoxycarbonyl protecting group can be accomplished under a number of conditions, including: AcCl in methanol (to generate HCl in situ), neat TFA, a solution of TFA in DCM, or a solution of 4N HCl in 1,4-dioxane. Installation of the heterocyclic sulfamide moiety can be accomplished by treatment with 5-amino-1,2,4-thiadiazole, sulfuryl chloride and TEA or an alternative method described in Schemes 9 to 12.

Scheme 3:

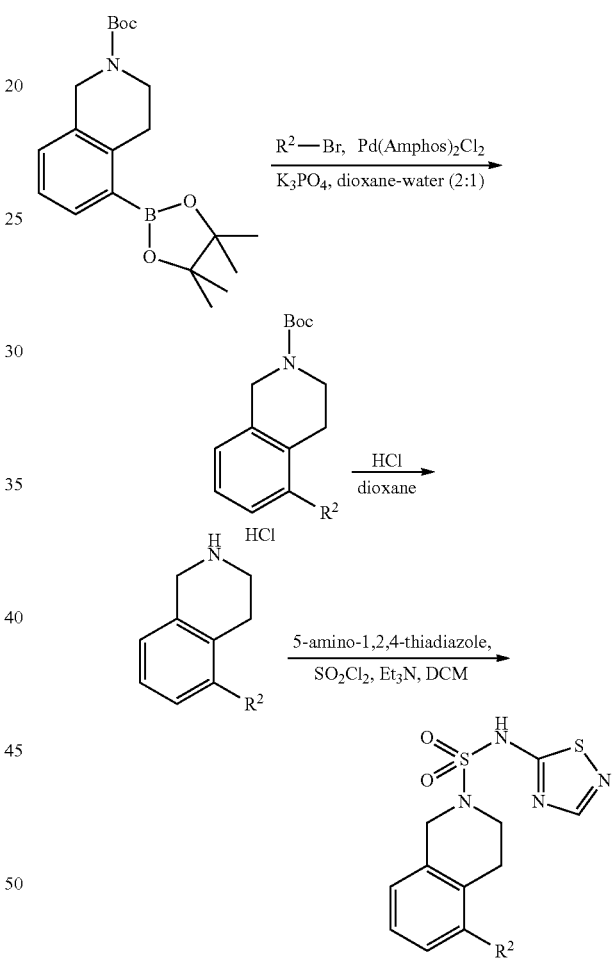

The Suzuki reaction with the protected tetrahydroisoquinoline boronate can be achieved using a variety of bases (such as Cs$_2$CO$_3$, K$_2$CO$_3$, K$_3$PO$_4$ or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). The removal of the tert-butoxycarbonyl protecting group can be accomplished under a number of conditions, including: AcCl in methanol (to generate HCl in situ), neat TFA, a solution of TFA in DCM, or a solution of 4N HCl in 1,4-dioxane. Installation of the heterocyclic sulfamide moiety can be accomplished by treatment with 5-amino-1,2,4-thiadiazole, sulfuryl chloride and TEA or an alternative method described in Schemes 9 to 12.

Scheme 4:

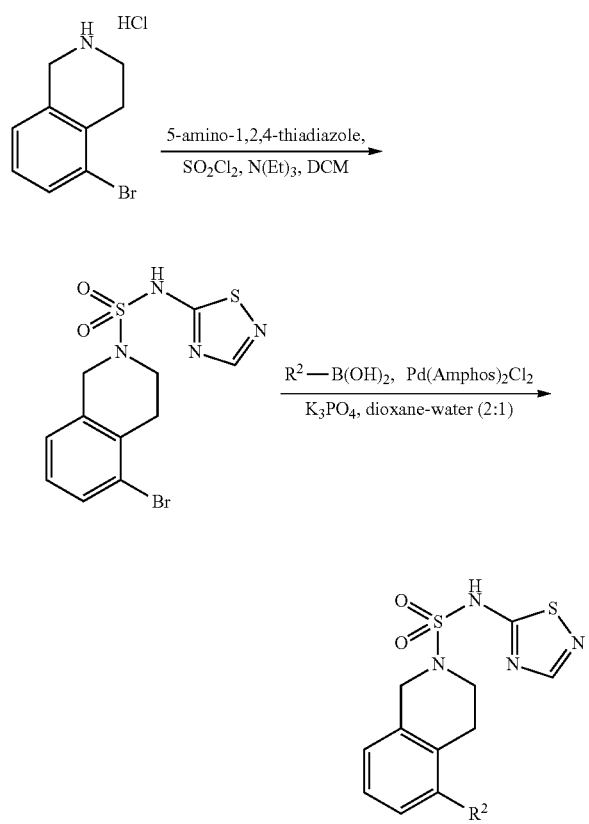

Installation of the heterocyclic sulfamide moiety on the tetrahydroisoquinoline bromide can be accomplished by treatment with 5-amino-1,2,4-thiadiazole, sulfuryl chloride and TEA or an alternative method described in Schemes 9 to 12. The Suzuki reaction with the tetrahydroisoquinoline sulfamide can be achieved using a variety of bases (such as $Cs_2CO_3$, $K_2CO_3$, $K_3PO_4$ or $Na_2CO_3$), catalysts (such as $Pd(AmPhos)_2Cl_2$, $Pd(dppf)Cl_2$ or $Pd(PPh_3)_4$), and solvents (such as aqueous 1,4-dioxane, DME, EtOH, DMF or t-BuOH).

Scheme 5:

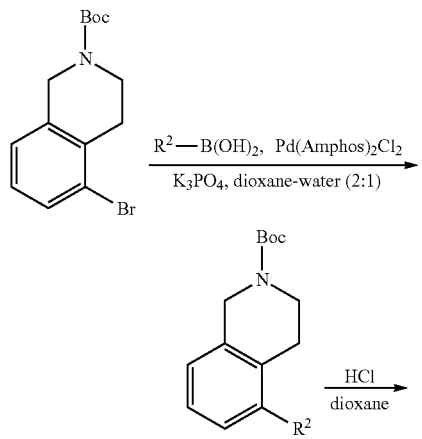

The Suzuki reaction with the protected tetrahydroisoquinoline bromide can be achieved using a variety of bases (such as $Cs_2CO_3$, $K_2CO_3$, $K_3PO_4$ or $Na_2CO_3$), catalysts (such as $Pd(AmPhos)_2Cl_2$, $Pd(dppf)Cl_2$ or $Pd(PPh_3)_4$), and solvents (such as aqueous 1,4-dioxane, DME, EtOH, DMF or t-BuOH). The removal of the tert-butoxycarbonyl protecting group can be accomplished under a number of conditions, including: AcCl in methanol (to generate HCl in situ), neat TFA, a solution of TFA in DCM, or a solution of 4N HCl in 1,4-dioxane. Installation of the heterocyclic sulfamide moiety can be accomplished by treatment with 5-amino-1,2,4-thiadiazole, sulfuryl chloride and TEA or an alternative method described in Schemes 9 to 12.

Scheme 6:

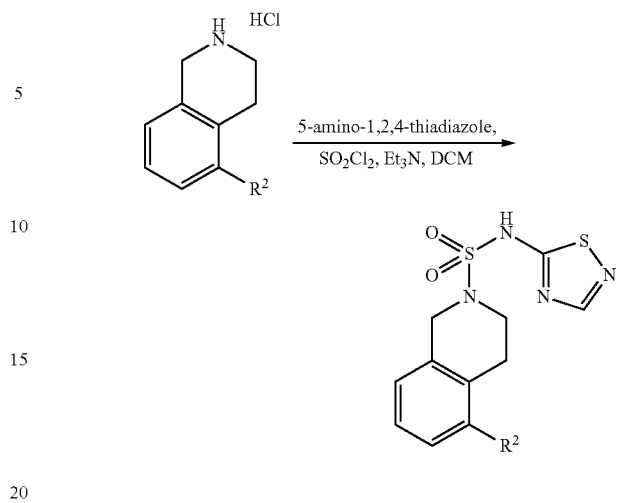

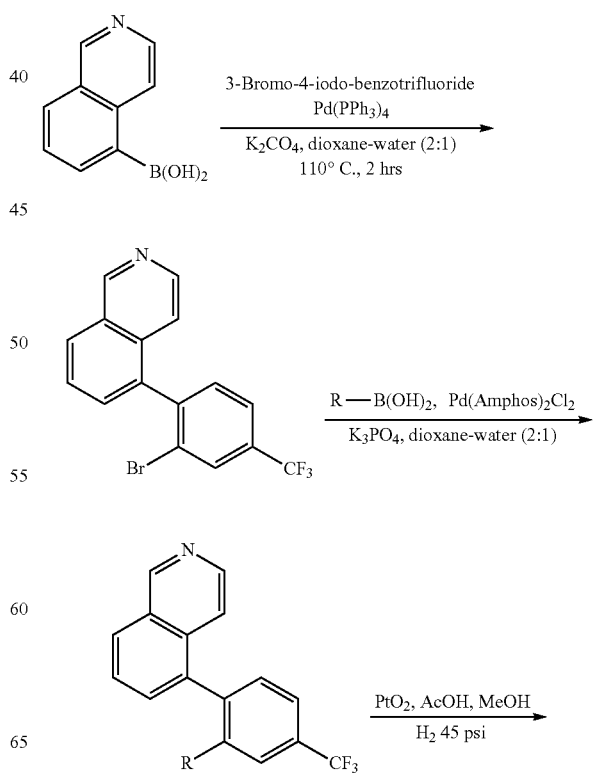

-continued

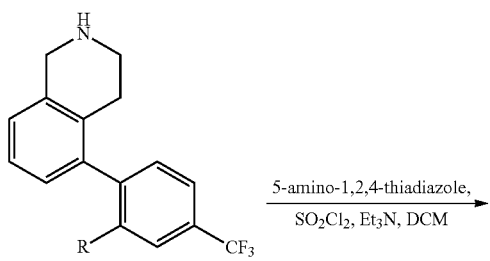

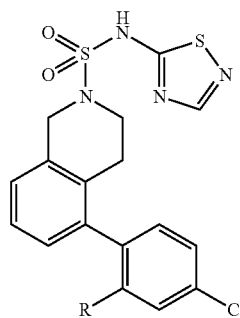

The Suzuki reaction with the isoquinoline boronic acid can be achieved using a variety of bases (such as Cs$_2$CO$_3$, K$_2$CO$_3$, K$_3$PO$_4$ or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). Further Suzuki reaction with the substituted isoquinoline bromide can be achieved using a variety of bases (such as Cs$_2$CO$_3$, K$_2$CO$_3$, K$_3$PO$_4$, or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). Reduction of the isoquinoline can be achieved with various catalysts (such as PtO$_2$, Pd/C or RuO$_2$), acids (such as acetic acid, trifluoroacetic acid, methanesulfonic acid, trifluoromethanesulfonic acid, HCl or BF$_3$ etherate) and solvents (such as MeOH, EtOH, EtOAc, DMF, DMSO or THF) under pressurized hydrogen gas. Installation of the heterocyclic sulfamide moiety can be accomplished by treatment with 5-amino-1,2,4-thiadiazole, sulfuryl chloride and TEA or an alternative method described in Schemes 9 to 12.

Scheme 7:

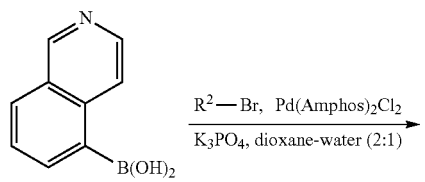

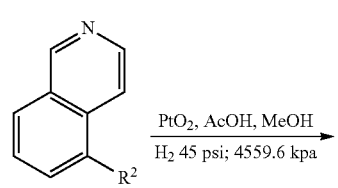

-continued

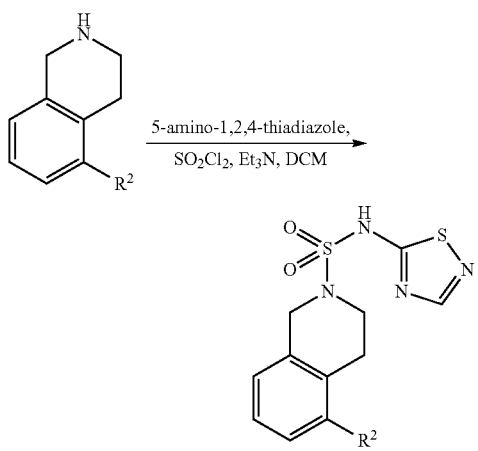

The Suzuki reaction with the isoquinoline boronic acid can be achieved using a variety of bases (such as Cs$_2$CO$_3$, K$_2$CO$_3$, K$_3$PO$_4$ or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). Reduction of the isoquinoline can be achieved with various catalysts (such as PtO$_2$, Pd/C or RuO$_2$), acids (such as acetic acid, trifluoroacetic acid, methanesulfonic acid, trifluoromethanesulfonic acid, HCl or BF$_3$ etherate) and solvents (such as MeOH, EtOH, EtOAc, DMF, DMSO or THF) under pressurized hydrogen gas. Installation of the heterocyclic sulfamide moiety can be accomplished by treatment with 5-amino-1,2,4-thiadiazole, sulfuryl chloride and TEA or an alternative method described in Schemes 9-12. Further suzuki reaction with the substituted isoquinoline bromide can be achieved using a variety of bases (such as Cs$_2$CO$_3$, K$_2$CO$_3$, K$_3$PO$_4$ or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH).

Scheme 8:

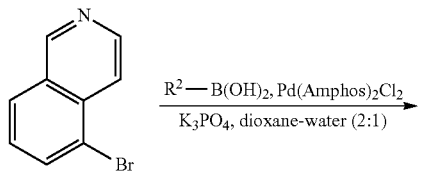

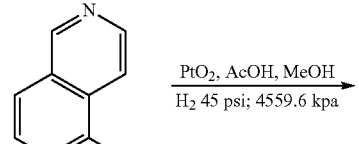

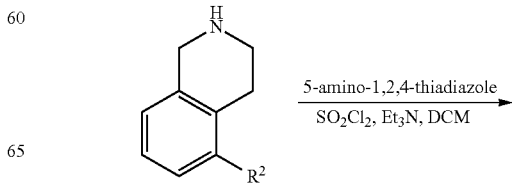

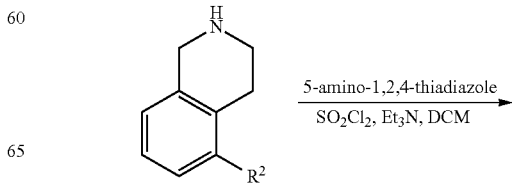

-continued

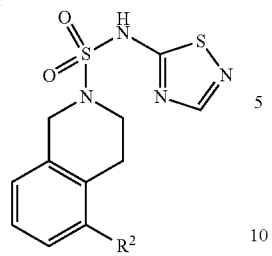

The Suzuki reaction with the isoquinoline bromide can be achieved using a variety of bases (such as $Cs_2CO_3$, $K_2CO_3$, $K_3PO_4$ or $Na_2CO_3$), catalysts (such as $Pd(AmPhos)_2Cl_2$, $Pd(dppf)Cl_2$ or $Pd(PPh_3)_4$), and solvents (such as aqueous 1,4-dioxane, DME, EtOH, DMF or t-BuOH). Reduction of the isoquinoline can be achieved with various catalysts (such as $PtO_2$, Pd/C or $RuO_2$), acids (such as acetic acid, trifluoroacetic acid, methanesulfonic acid, trifluoromethanesulfonic acid, HCl or $BF_3$ etherate) and solvents (such as MeOH, EtOH, EtOAc, DMF, DMSO or THF) under pressurized hydrogen gas. Installation of the heterocyclic sulfamide moiety can be accomplished by treatment with 5-amino-1,2,4-thiadiazole, sulfuryl chloride and TEA or an alternative method described in Schemes 9 to 12.

Scheme 9:

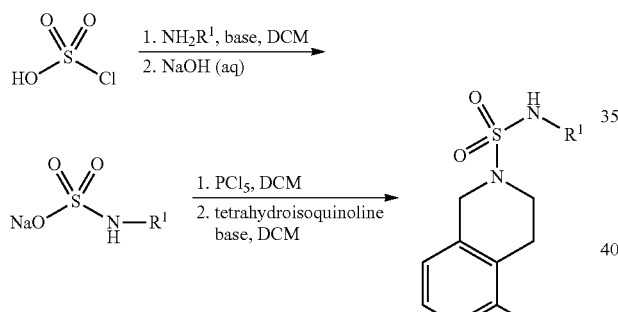

Heterocyclic sulfamates may be prepared by treating chlorosulfonic acid in various solvents (such as DCM, DCE, chloroform, benzene, pyridine or toluene) with organic bases (such as triethylamine, N,N-diisopropylethylamine, DBU or pyridine) and an appropriate amine followed by treatment with aqueous base (such as NaOH, KOH, LiOH or $NH_4OH$). The sulfamate can be activated with various reagents (including $PCl_5$, $POCl_3$, thionyl chloride or oxalyl chloride) in various aprotic solvents (such DCM, DCE, chloroform, THF or acetonitrile). Coupling of the sulfamoyl chloride and tetrahydroisoquinoline may be accomplished with various bases (such as triethylamine, N,N-diisopropylethylamine, DBU, $Cs_2CO_3$, $K_2CO_3$, $K_3PO_4$, or $Na_2CO_3$) in a variety of solvents (including DCM, DCE, THF, acetonitrile, DMF or DMSO).

Scheme 10:

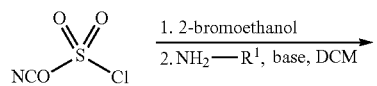

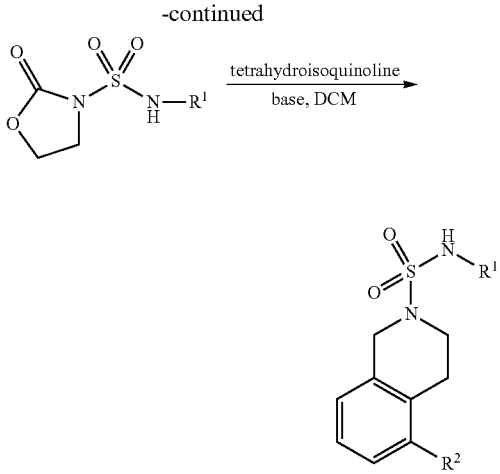

Activated heterocyclic sulfamides may be prepared in various solvents (such as DCM, DCE, chloroform, benzene, pyridine or toluene) by treating cyanic sulfurochloridic anhydride with 2-bromoethanol. The derived reagent can then be reacted with an organic bases (such as triethylamine, N,N-diisopropylethylamine, DBU or pyridine) in the presence of an appropriate amine Coupling of the activated sulfamide and a suitable tetrahydroisoquinoline may be accomplished with various bases (such as triethylamine, N,N-diisopropylethylamine, DBU, $Cs_2CO_3$, $K_2CO_3$, $K_3PO_4$ or $Na_2CO_3$) in a variety of solvents (including DCM, DCE, THF, acetonitrile, DMF or DMSO).

Scheme 11:

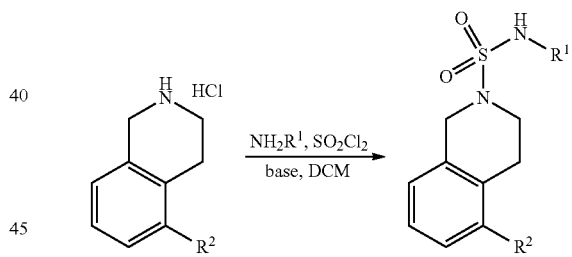

Conversion of a suitably elaborated tetrahydroisoquinoline or derived salt thereof into the corresponding sulfamide can be achieved by treating the appropriate amine ($NH_2R^1$) with sulfuryl chloride and imidazole (or a suitable alternative). The derived activated sulfonylating reagent can then be added to a solution of the tetrahydroisoquinoline in the presence of an appropriate base (including triethylamine, N,N-diisopropylethylamine, DBU or imidazole).

Scheme 12:

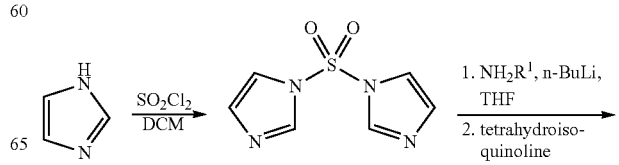

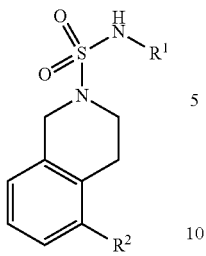

Tetrahydroisoquinoline intermediates can also be converted into sulfamides by the procedure outlined below. Imidazole can be converted to 1,1'-sulfonylbis(1H-imidazole) by treatment with sulfuryl chloride. The derived reagent can the be treated with an appropriate amine (NH₂R¹) and a suitable base (n-BuLi, s-BuLi, LiOtBu, LiHMDS or LDA) to provide a reagent that upon treatment with a suitably substituted tetrahydroisoquinoline provides the desired sulfamide.

Preparation of Intermediates

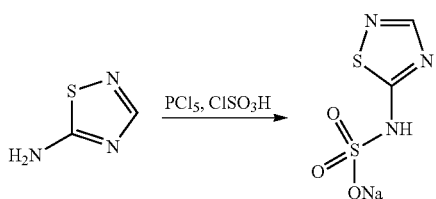

Intermediate A: Sodium 1,2,4-thiadiazol-5-ylsulfamate

In a 15-mL round-bottom flask, 1,2,4-thiadiazol-5-amine (205 mg, 1.711 mmol) was dissolved in pyridine (2 mL). A drop of chlorosulfonic acid was added and the flask was placed in an ice-bath for 5 min before the rest of the chlorosulfonic acid (136 μL, 2.053 mmol) was added. After the addition, a reflux condenser was attached, and the flask was lowered into a 50° C. oil bath. The solids dissolved over the next 20 to 30 min, and those that didn't were scraped off of the sides of the flask. After 1 hour, the flask was removed from the heat. The mixture was diluted with DCM, then concentrated. The residue was placed under high vacuum to remove most of the pyridine. The residue was then diluted with saturated aq. sodium carbonate (20 mL) until basic. The mixture was then diluted with water and the mixture was concentrated to give a solid. The solid was extracted with boiling ethanol (3×20 mL). The ethanol extract was concentrated to give an off-white solid. The solid was taken up in methanol and transferred to a smaller flask to give sodium 1,2,4-thiadiazol-5-ylsulfamate (216.5 mg, 1.066 mmol) after evaporation. [M+H]+=182.1

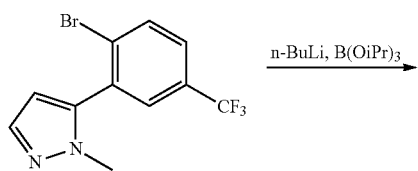

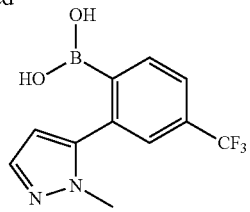

Intermediate B: (2-(1-Methyl-1H-pyrazol-5-yl)-4-(trifluoromethyl)phenyl)boronic acid A 50-mL round-bottom flask was charged with 5-(2-bromo-5-(trifluoromethyl)phenyl)-1-methyl-1H-pyrazole (Intermediate C, 638 mg, 2.091 mmol), diethyl ether (15 mL), and triisopropyl borate (583 μl, 2.509 mmol) to give a slightly opaque, yellow solution. The flask was cooled in a dry ice-acetone bath for 10 min, then n-butyllithium (2.1M in hexane) (1195 μl, 2.509 mmol) was added dropwise over 1 minute. After 1 hour, the cooling bath was removed and a 2N aq. NaOH solution (20 mL) was added, and the resulting biphasic mixture was stirred vigorously. After 1 hour, the mixture was diluted with water. The layers were separated, and the ethereal layer was extracted with water (2×). The water layers were combined, and the combined aq. mixture as washed with diethyl ether. The ethereal layer was back-extracted once more, and the aq. layers were all combined. The combined solution was acidified to about. pH 2 with 6N aq. HCl to give a clear solution. The aq. solution was extracted with EtOAc (3×), and the combined organic extracts were dried over sodium sulfate, filtered and concentrated. The residue was taken up in DCM and concentrated under a vacuum to give (2-(1-methyl-1H-pyrazol-5-yl)-4-(trifluoromethyl)phenyl) boronic acid (471 mg, 1.744 mmol) as a light-yellow solid. [M+H]+=271.2.

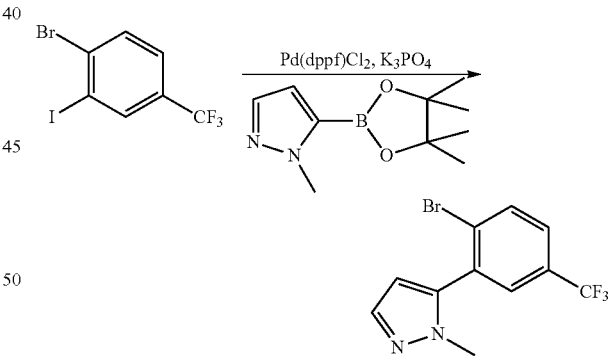

Intermediate C: 5-(2-Bromo-5-(trifluoromethyl)phenyl)-1-methyl-1H-pyrazole

A 75-mL pressure vessel was charged with 1-bromo-2-iodo-4-(trifluoromethyl)benzene (2.015 g, 5.74 mmol), 1-methyl-5-(4,4,5,5-tetramethyl-1,3,2-dioxaborolan-2-yl)-1H-pyrazole (Aldrich, St. Louis, Mo., 1.374 g, 6.60 mmol), potassium phosphate (2.438 g, 11.48 mmol), and PdCl₂ (dppf)-CH₂Cl₂ adduct (Strem Chemicals Inc., Newburyport, Mass., 0.469 g, 0.574 mmol). The vessel was flushed with Ar (g), then DMF (19.14 ml) was added. The vial was sealed and placed in an 80° C. oil bath for 2 hours. The mixture was diluted with water and extracted with EtOAc (3×). The combined organic extracts were washed with brine, dried over sodium sulfate, filtered, and concentrated. The residue was chromatographed on an 80 g silica gel column to give 5-(2-bromo-5-(trifluoromethyl)phenyl)-1-methyl-1H-pyrazole (1.001 g, 3.28 mmol) as a yellow solid. [M+H]+=307.0.

product, so the reaction mixture was concentrated yielding 5-(2-bromo-4-(trifluoromethyl)phenyl)-1,2,3,4-tetrahydroisoquinoline hydrochloride (2.32 g, 5.91 mmol). [M+H]+=357.9.

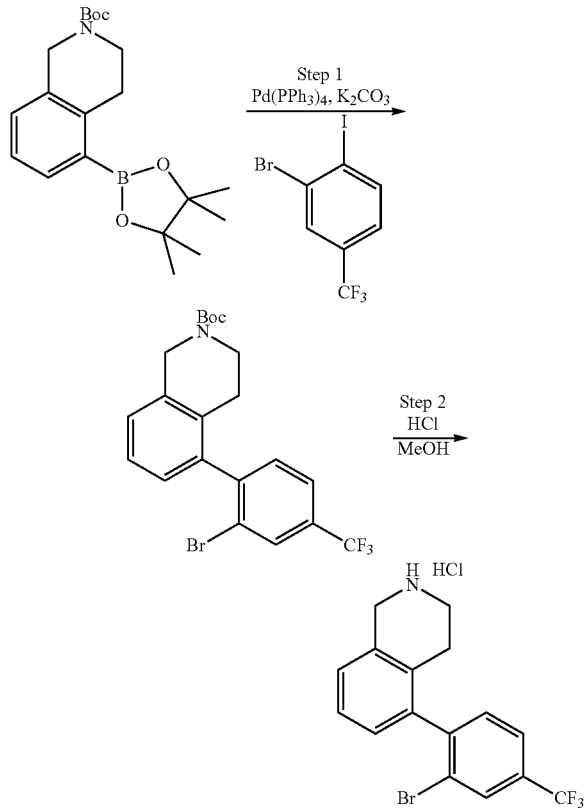

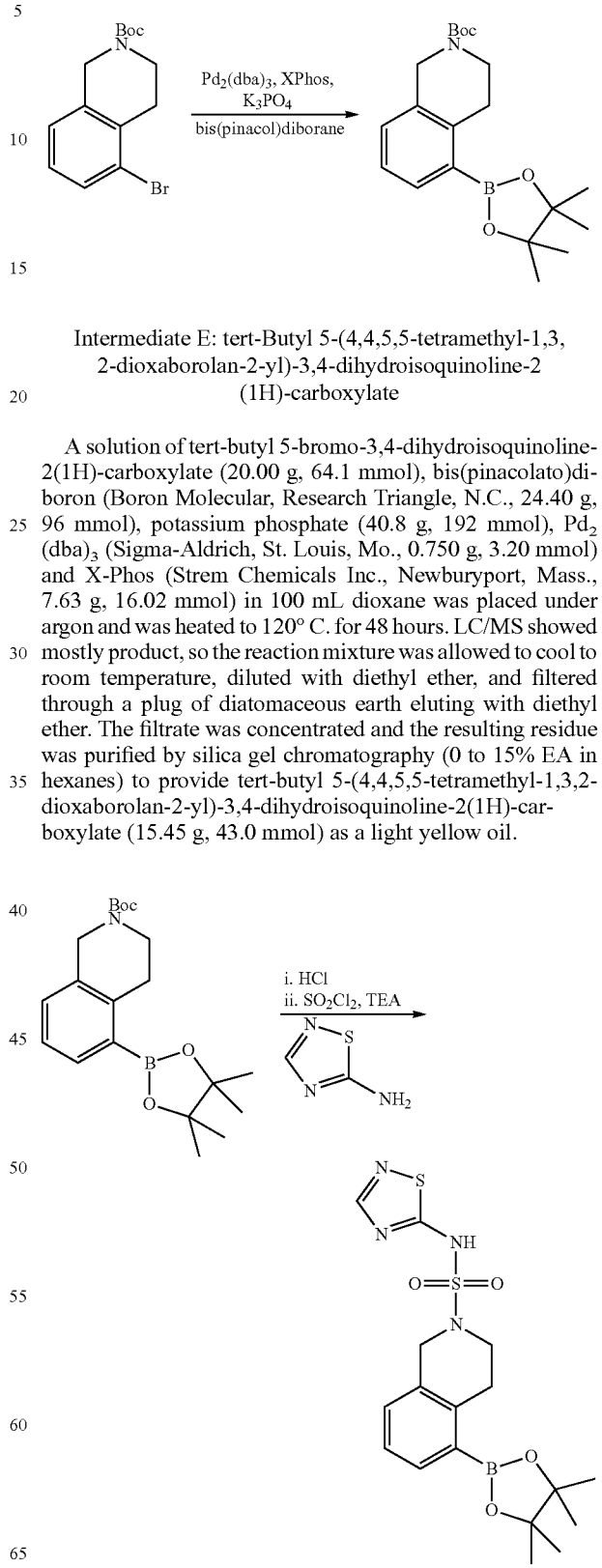

Intermediate E: tert-Butyl 5-(4,4,5,5-tetramethyl-1,3,2-dioxaborolan-2-yl)-3,4-dihydroisoquinoline-2(1H)-carboxylate A solution of tert-butyl 5-bromo-3,4-dihydroisoquinoline-2(1H)-carboxylate (20.00 g, 64.1 mmol), bis(pinacolato)diboron (Boron Molecular, Research Triangle, N.C., 24.40 g, 96 mmol), potassium phosphate (40.8 g, 192 mmol), Pd$_2$(dba)$_3$ (Sigma-Aldrich, St. Louis, Mo., 0.750 g, 3.20 mmol) and X-Phos (Strem Chemicals Inc., Newburyport, Mass., 7.63 g, 16.02 mmol) in 100 mL dioxane was placed under argon and was heated to 120° C. for 48 hours. LC/MS showed mostly product, so the reaction mixture was allowed to cool to room temperature, diluted with diethyl ether, and filtered through a plug of diatomaceous earth eluting with diethyl ether. The filtrate was concentrated and the resulting residue was purified by silica gel chromatography (0 to 15% EA in hexanes) to provide tert-butyl 5-(4,4,5,5-tetramethyl-1,3,2-dioxaborolan-2-yl)-3,4-dihydroisoquinoline-2(1H)-carboxylate (15.45 g, 43.0 mmol) as a light yellow oil.

Intermediate D: 5-(2-Bromo-4-(trifluoromethyl)phenyl)-1,2,3,4-tetrahydroisoquinoline Step 1: A solution of Pd(PPh$_3$)$_4$ (Strem Chemicals Inc., Newburyport, Mass., 0.804 g, 0.696 mmol), 2-bromo-1-iodo-4-(trifluoromethyl)benzene (Matrix Scientific, Columbia, S.C., 3.05 g, 8.70 mmol), tert-butyl 5-(4,4,5,5-tetramethyl-1,3,2-dioxaborolan-2-yl)-3,4-dihydroisoquinoline-2(1H)-carboxylate (ASW Medchem, Brunswick, N.J., 2.500 g, 6.96 mmol), and potassium carbonate (4.81 g, 34.8 mmol) in 14 mL dioxane and 6 mL water was heated to 100° C. overnight. LC/MS showed about 50% conversion, so the reaction mixture was transferred to a microwave vial, and was heated to 130° C. in a microwave reactor for 3 hours. The reaction mixture was diluted with EtOAc, washed with water then brine, the organics dried over MgSO$_4$ and concentrated. Purification of the resulting residue by silica gel column chromatography (0 to 30% EtOAc/heptane) gave tert-butyl 5-(2-bromo-4-(trifluoromethyl)phenyl)-3,4-dihydroisoquinoline-2(1H)-carboxylate (2.73 g, 5.98 mmol).

Step 2: A solution of tert-butyl 5-(2-bromo-4-(trifluoromethyl)phenyl)-3,4-dihydroisoquinoline-2(1H)-carboxylate (2.73 g, 5.98 mmol) in 12 mL THF was treated with methanol (2.421 ml, 59.8 mmol) and was cooled to 0° C. Acetyl chloride (4.25 ml, 59.8 mmol) was added, and the reaction mixture was allowed to stir overnight. LC/MS showed mostly

Intermediate F: 5-(4,4,5,5-Tetramethyl-1,3,2-dioxaborolan-2-yl)-N-(1,2,4-thiadiazol-5-yl)-3,4-dihydroisoquinoline-2(1H)-sulfonamide A solution of tert-butyl 5-(4,4,5,5-tetramethyl-1,3,2-dioxaborolan-2-yl)-3,4-dihydroisoquinoline-2(1H)-carboxylate (ASW Medchem, Brunswick, N.J., 2.340 g, 6.51 mmol) in 7 mL THF was treated with HCl 4 N in dioxane (8.14 ml, 32.6 mmol) and was allowed to stir at room temperature overnight. LC/MS showed mostly product, so the reaction mixture was concentrated. The resulting residue was triturated with heptane, and the solid was dried and collected. A separate flask charged with 1,2,4-thiadiazol-5-amine (1.317 g, 13.03 mmol), 26 mL DCM, and triethylamine (4.54 ml, 32.6 mmol) was cooled to −78° C. and was treated with sulfuryl chloride (1.059 ml, 13.03 mmol). After stirring for one hour, the reaction mixture was filtered through a syringe filter and was treated with the 5-(4,4,5,5-tetramethyl-1,3,2-dioxaborolan-2-yl)-1,2,3,4-tetrahydroisoquinoline derived above. After stirring overnight, LC/MS showed product so the reaction mixture was filtered then concentrated. Purification of the resulting residue by silica gel column chromatography (0 to 100% EtOAc/heptane) gave 5-(4,4,5,5-tetramethyl-1,3,2-dioxaborolan-2-yl)-N-(1,2,4-thiadiazol-5-yl)-3,4-dihydroisoquinoline-2(1H)-sulfonamide (0.711 g, 1.684 mmol). [M+H]+=423.3

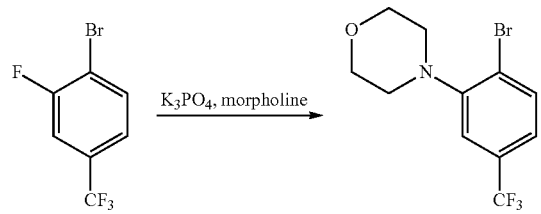 [SMILES: Fc1cc(C(F)(F)F)ccc1Br ; FC(F)(F)c1ccc(Br)c(N2CCOCC2)c1]

Intermediate G: 4-(2-Bromo-5-(trifluoromethyl)phenyl)morpholine

A microwave vial charged with potassium phosphate (0.533 g, 2.51 mmol), 1-bromo-2-fluoro-4-(trifluoromethyl)benzene (0.610 g, 2.51 mmol) and 1 mL dioxane, was treated with morpholine (0.437 ml, 5.02 mmol) and was heated to 150° C. in a microwave reactor for one hour. LC/MS showed mostly starting material, so the reaction mixture was treated with 1 mL DMF and was heated to 150° C. in an oil bath overnight. LC/MS showed product, so the reaction mixture was diluted with DCM, filtered through a syringe filter, and concentrated. Purification of the resulting residue by silica gel column chromatography (0 to 50% EtOAc/heptane) gave 4-(2-bromo-5-(trifluoromethyl)phenyl)morpholine (0.280 g, 0.903 mmol) as a clear oil. [M+H]+=312.0

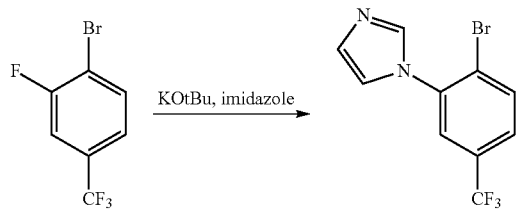

Intermediate H: 1-(2-Bromo-5-(trifluoromethyl)phenyl)-1H-imidazole

A microwave vial charged with a solution of potassium tert-butoxide (0.462 g, 4.12 mmol), imidazole (0.280 g, 4.12 mmol), and 1-bromo-2-fluoro-4-(trifluoromethyl)benzene (1.000 g, 4.12 mmol) in 2 mL DMF was heated to 150° C. in an oil bath overnight. The reaction mixture was diluted with DCM, filtered through a syringe filter, and concentrated. Purification of the resulting residue by silica gel column chromatography (0 to 100% EtOAc/heptane) gave 1-(2-bromo-5-(trifluoromethyl)phenyl)-1H-imidazole (0.720 g, 2.474 mmol). [M+H]+=291.0

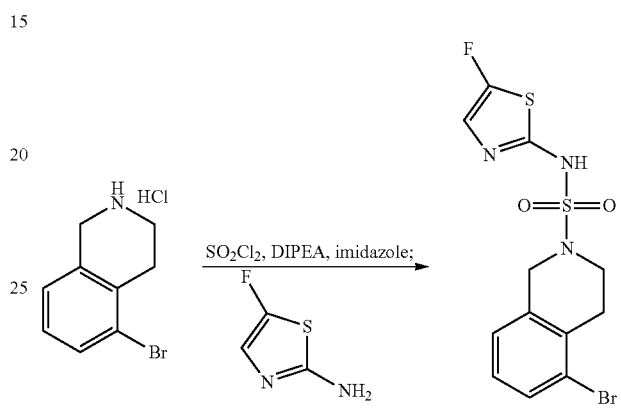

Intermediate I: 5-Bromo-N-(5-fluorothiazol-2-yl)-3,4-dihydroisoquinoline-2(1H)-sulfonamide A solution of 5-fluorothiazol-2-amine hydrochloride (Milestone Pharmatech, Brunswick, N.J., 6.22 g, 40.2 mmol) and 1H-imidazole (10.96 g, 161 mmol) in 200 mL DCM was cooled to −78° C. and was treated with sulfuryl chloride (3.27 ml, 40.2 mmol). After stirring for 10 minutes, the reaction mixture was placed into a 0° C. bath and was allowed to stir for an additional hour. To this mixture was added 30 mL of heptane and the solvent was decanted. The remaining solid was treated with 5-bromo-1,2,3,4-tetrahydroisoquinoline hydrochloride (ASW Medchem, Brunswick, N.J., 5.00 g, 20.12 mmol) then treated sequentially with 100 mL THF and DIPEA (42.2 ml, 241 mmol). The reaction mixture was heated to reflux for one hour before being cooled and poured into 1N citric acid. The desired product was extracted with ethyl acetate. The organics were concentrated and the resulting residue was purified directly by silica gel column chromatography (0 to 100% EtOAc/heptane, 2% MeOH) yielding 5-bromo-N-(5-fluorothiazol-2-yl)-3,4-dihydroisoquinoline-2(1H)-sulfonamide (3.25 g, 8.29 mmol). [M+H]+=393.9

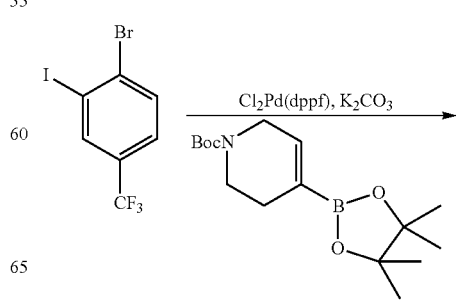

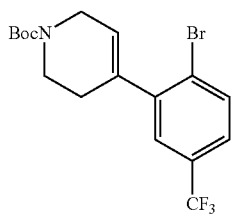

Intermediate J: tert-Butyl 4-(2-bromo-5-(trifluoromethyl)phenyl)-5,6-dihydropyridine-1(2H)-carboxylate A solution of 1-bromo-2-iodo-4-(trifluoromethyl)benzene (1.408 ml, 8.55 mmol), tert-butyl 4-(4,4,5,5-tetramethyl-1,3,2-dioxaborolan-2-yl)-5,6-dihydropyridine-1(2H)-carboxylate (Frontier Scientific, Logan, Utah, 2.78 g, 8.98 mmol), Pd(dppf)Cl$_2$—CH$_2$Cl$_2$ adduct (Strem Chemicals Inc., Newburyport, Mass., 0.349 g, 0.427 mmol), and potassium carbonate (2.052 g, 34.2 mmol) in dioxane (32.1 ml) and water (10.69 ml) was stirred at 70° C. for three hours. (LC-MS MH+ 430.1) The reaction was diluted with ethyl acetate and washed with water. The aqueous layer was extracted with ethyl acetate, and the combined organic layers were dried with sodium sulfate, filtered, and concentrated. The material was purified via column chromatography (silica gel 80 g, gradient elution 0 to 100% Et$_2$O:Heptane) to afford tert-butyl 4-(2-bromo-5-(trifluoromethyl)phenyl)-5,6-dihydropyridine-1(2H)-carboxylate (2.54 g, 6.25 mmol) as a light yellow oil. [M+H]+=428.0. $^1$H NMR (400 MHz, CHLOROFORM-d) δ ppm=7.69 (d, J=8.3 Hz, 1H), 7.43 (d, J=2.2 Hz, 1H), 7.41-7.36 (m, 1H), 5.69 (br. s., 1H), 4.08 (q, J=2.7 Hz, 2H), 3.66 (t, J=5.6 Hz, 2H), 2.48-2.40 (m, 2H), 1.52 (s, 9H)

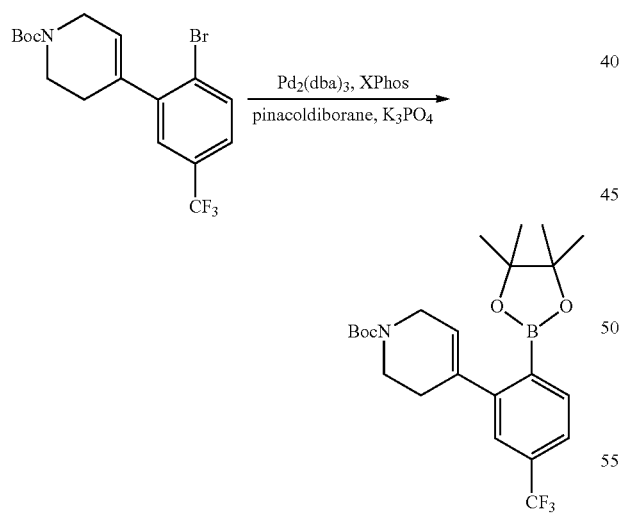

Intermediate K: tert-Butyl 4-(2-(4,4,5,5-tetramethyl-1,3,2-dioxaborolan-2-yl)-5-(trifluoromethyl)phenyl)-5,6-dihydropyridine-1(2H)-carboxylate A round bottom flask was charged with tert-butyl 4-(2-bromo-5-(trifluoromethyl)phenyl)-5,6-dihydropyridine-1(2H)-carboxylate (Intermediate J, 2.73 g, 6.72 mmol), bis(pinacolato)diboron (3.41 g, 13.44 mmol), potassium phosphate (4.28 g, 20.16 mmol), Pd$_2$(dba)$_3$ (Strem Chemicals Inc., Newburyport, Mass., 0.308 g, 0.336 mmol), and X-Phos (Strem Chemicals Inc., Newburyport, Mass., 0.320 g, 0.672 mmol) Dioxane (33.6 ml) was added, the flask was fitted with a reflux condenser, and the reaction was heated to 90° C. and stirred for four hours. (LC-MS [M+H]$^+$ 354.2). The reaction was cooled to room temperature, filtered through diatomaceous earth, and washed with ethyl acetate. The filtrate was concentrated and purified via column chromatography (silica gel 80 g, gradient elution 0 to 25% heptane:diethyl ether) to afford tert-butyl 4-(2-(4,4,5,5-tetramethyl-1,3,2-dioxaborolan-2-yl)-5-(trifluoromethyl)phenyl)-5,6-dihydropyridine-1(2H)-carboxylate (1.86 g, 4.10 mmol) as a yellow oil. [M+H]+=354.2

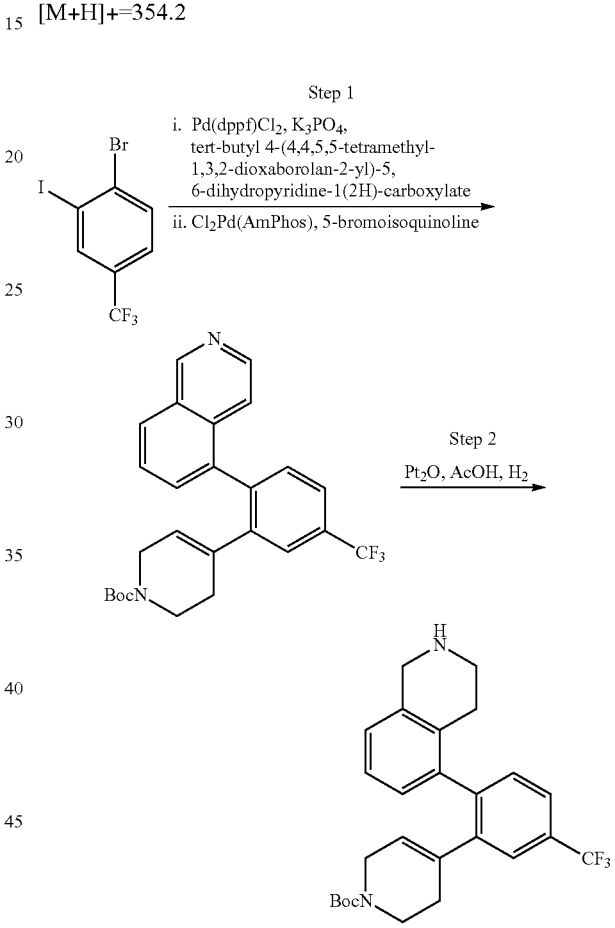

Intermediate L: tert-Butyl 4-(2-(1,2,3,4-tetrahydroisoquinolin-5-yl)-5-(trifluoromethyl)phenyl)-5,6-dihydropyridine-1(2H)-carboxylate Step 1: tert-Butyl 4-(2-(isoquinolin-5-yl)-5-(trifluoromethyl)phenyl)-5,6-dihydropyridine-1(2H)-carboxylate A solution of Cl$_2$Pd(dppf)-CH$_2$Cl$_2$ adduct (Strem Chemicals Inc., Newburyport, Mass., 1.157 g, 1.416 mmol), (n-tert-butoxycarbonyl)-1,2,3,6-tetrahydropyridine-4-boronic acid pinacol ester (Maybridge Chemicals, Cornwall, UK, 8.76 ml, 28.3 mmol), 1-bromo-2-iodo-4-(trifluoromethyl)benzene (Combi-Blocks, San Diego, Calif., 9.94 g, 28.3 mmol), and potassium phosphate (36.1 g, 170 mmol) in 100 mL dioxane and 40 mL water was heated to 100° C. for 3 hours. LC/MS showed clean conversion to tert-butyl 4-(2-bromo-5-(trifluoromethyl)phenyl)-5,6-dihydropyridine-1(2H)-carboxylate. To the resulting mixture was added isoquinolin-5-ylboronic acid (Sigma-Aldrich, St. Louis, Mo., 4.90 g, 28.3 mmol) and Cl$_2$Pd(AmPhos) (Sigma-Aldrich, St. Louis, Mo., 1.003 g, 1.416 mmol). The reaction mixture was again heated to 100° C. an additional hour before the reaction mixture was allowed to cool to room temperature and was diluted with diethyl ether. The organics were washed with water, then brine, dried over MgSO$_4$ and concentrated. Purification of the resulting residue by silica gel column chromatography (0 to 100% EtOAc/heptane) gave tert-butyl 4-(2-(isoquinolin-5-yl)-5-(trifluoromethyl)phenyl)-5,6-dihydropyridine-1(2H)-carboxylate (9.80 g, 21.56 mmol).

Step 2: tert-Butyl 4-(2-(1,2,3,4-tetrahydroisoquinolin-5-yl)-5-(trifluoromethyl)phenyl)-5,6-dihydropyridine-1(2H)-carboxylate A solution of tert-butyl 4-(2-(isoquinolin-5-yl)-5-(trifluoromethyl)phenyl)-5,6-dihydropyridine-1(2H)-carboxylate (9.80 g, 21.56 mmol) in 50 mL MeOH was treated with acetic acid (1.234 ml, 21.56 mmol) and platinum(IV) oxide (0.979 g, 4.31 mmol) and was placed under 45 psi (4459.6 kpa) H$_2$ overnight. LC/MS showed exclusively product, so the reaction mixture was filtered through a plug of diatomaceous earth and concentrated. The resulting residue was taken up in DCM and was washed with saturated NaHCO$_3$ solution. The organics were dried over MgSO$_4$ and concentrated yielding tert-butyl 4-(2-(1,2,3,4-tetrahydroisoquinolin-5-yl)-5-(trifluoromethyl)phenyl)-5,6-dihydropyridine-1(2H)-carboxylate (8.21 g, 17.91 mmol). [M+H]+=459.0

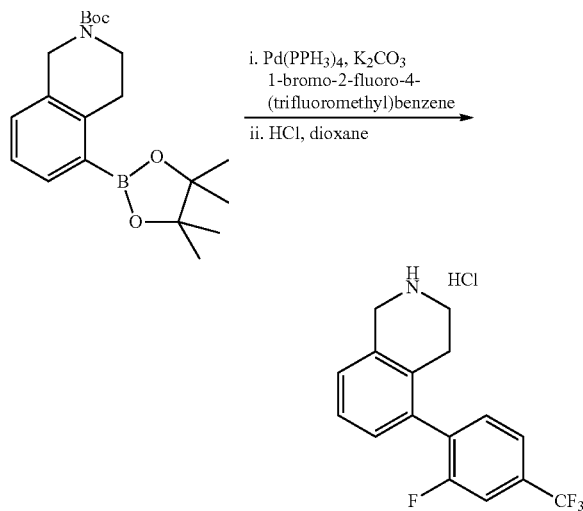

Intermediate M: 5-(2-Fluoro-4-(trifluoromethyl)phenyl)-1,2,3,4-tetrahydroisoquinoline hydrochloride A solution of Pd(PPh$_3$)$_4$ (Strem Chemicals Inc., Newburyport, Mass., 0.643 g, 0.557 mmol), 1-bromo-2-fluoro-4-(trifluoromethyl)benzene (1.353 g, 5.57 mmol), tert-butyl 5-(4,4,5,5-tetramethyl-1,3,2-dioxaborolan-2-yl)-3,4-dihydroisoquinoline-2(1H)-carboxylate (ASW Medchem, Brunswick, N.J., 2.000 g, 5.57 mmol), and potassium carbonate (3.08 g, 22.27 mmol) in 12 mL dioxane and 6 mL water was heated to 120° C. for 3 days. The reaction mixture was diluted with diethyl ether, washed with water, the organics dried over MgSO$_4$ and concentrated to provide tert-butyl 5-(2-fluoro-4-(trifluoromethyl)phenyl)-3,4-dihydroisoquinoline-2(1H)-carboxylate. The resulting residue was dissolved in 10 mL THF and was treated with HCl 4 N in dioxane (9.74 ml, 39.0 mmol), and allowed to stir at room temperature overnight. The reaction mixture was diluted with diethyl ether/heptane, and the resulting solid was filtered and dried yielding 5-(2-fluoro-4-(trifluoromethyl)phenyl)-1,2,3,4-tetrahydroisoquinoline hydrochloride (1.930 g, 5.82 mmol). [M+H]+=296.1

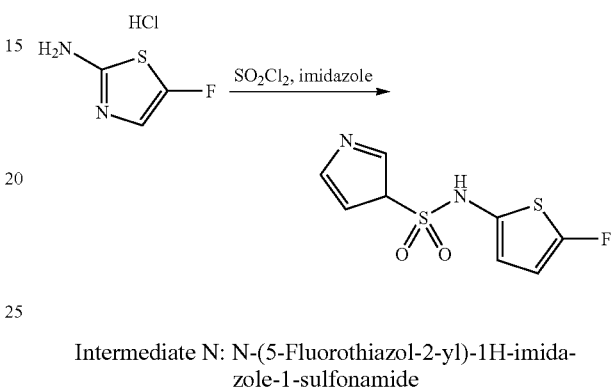

Intermediate N: N-(5-Fluorothiazol-2-yl)-1H-imidazole-1-sulfonamide

A solution of 1H-imidazole (6.17 g, 91 mmol) and 5-fluorothiazol-2-amine hydrochloride (Milestone Pharmatech, Brunswick, N.J., 3.50 g, 22.64 mmol) in 100 mL DCM was cooled to −78° C. sulfuryl chloride (1.841 ml, 22.64 mmol) was added, and the reaction mixture was allowed to stir for 10 minutes. The reaction mixture was then transferred to a 0° C. cooling bath, and was allowed to stir for an additional hour. LC/MS showed mostly product, so the reaction mixture was diluted with a small amount of heptane, and the solvent was decanted off. The resulting solid was dried (kept under vacuum) and used without further purification. [M+H]+=249.0

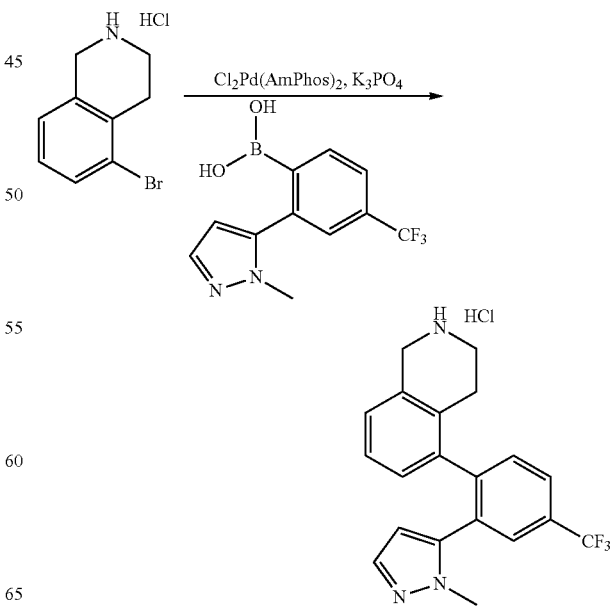

Intermediate O: 5-(2-(1-Methyl-1H-pyrazol-5-yl)-4-(trifluoromethyl)phenyl)-1,2,3,4-tetrahydroisoquinoline A vial was charged with 5-bromo-1,2,3,4-tetrahydroisoquinoline hydrochloride (ASW Medchem, Brunswick, N.J., 400.42 mg, 1.367 mmol), (2-(1-methyl-1H-pyrazol-5-yl)-4-(trifluoromethyl)phenyl)boronic acid (Intermediate B, 443 mg, 1.640 mmol), potassium phosphate (1160 mg, 5.47 mmol), and Pd(AmPhos)$_2$Cl$_2$ (Sigma-Aldrich, St. Louis, Mo., 48.4 mg, 0.068 mmol). The vial was flushed with Ar (g), then dioxane (2928 µl) and water (976 µl) were added in sequence. The mixture was heated in a microwave reactor for 30 min at 90° C. After cooling to room temperature, the mixture was diluted with EtOAc, washed with water (and a small amount of brine to break up emulsions, 2×), washed with brine, dried over sodium sulfate, filtered, and concentrated. The residue was taken up in MeOH, then loaded onto a 10 g SCX-2 ion exchange column. The column was eluted with MeOH, then with 2M ammonia in MeOH. The basic filtrate was concentrated, and the residue was chromatographed on a 40 g silica gel column with 0 to 10% MeOH/DCM to provide 5-(2-(1-methyl-1H-pyrazol-5-yl)-4-(trifluoromethyl)phenyl)-1,2,3,4-tetrahydroisoquinoline as a pale yellow solid. [M+H]+=358.1. $^1$H NMR (400 MHz, DMSO-d$_6$) δ ppm=7.91-7.80 (m, 2H), 7.56 (d, J=8.0 Hz, 1H), 7.28 (d, J=2.0 Hz, 1H), 7.09-6.95 (m, 2H), 6.84 (dd, J=1.3, 7.4 Hz, 1H), 5.96 (d, J=1.9 Hz, 1H), 3.85 (s, 2H), 3.52 (br. s., 3H), 2.93-2.84 (m, 1H), 2.79-2.67 (m, 1H), 2.48-2.39 (m, 1H), 2.09 (td, J=5.3, 16.7 Hz, 1H).

Intermediate P: (2-(Pyridin-4-yl)-4-(trifluoromethyl)phenyl)boronic acid

Step 1: 4-(2-bromo-5-(trifluoromethyl)phenyl)pyridine

A solution of pd(ph3p)4 (1.410 g, 1.220 mmol), 1-bromo-2-iodo-4-(trifluoromethyl)benzene (3.94 ml, 24.41 mmol), pyridin-4-ylboronic acid (3.00 g, 24.41 mmol), and potassium carbonate (13.49 g, 98 mmol) in 32 mL dioxane and 6 mL water was heated to 120° C. overnight. Additional portions of pyridin-4-ylboronic acid (3.00 g, 24.41 mmol) and potassium carbonate (13.49 g, 98 mmol) were added and the reaction mixture was heated to 120° C. for 3 hours. The reaction mixture was then poured into water and was extracted with DCM. The organics were then concentrated. Purification of the crude residue by silica gel column chromatography (0-100% EtOAc/heptane) gave 4-(2-bromo-5-(trifluoromethyl)phenyl)pyridine (3.054 g, 10.11 mmol, 41.4% yield) as a white solid. [M+H]+=303.9

Step 2: (2-(Pyridin-4-yl)-4-(trifluoromethyl)phenyl)boronic acid

A 250-mL round bottom flask was charged with 4-(2-bromo-5-(trifluoromethyl)phenyl)pyridine (0.242 g, 0.801 mmol), Ether (6.16 ml), and triisopropyl borate (0.223 ml, 0.961 mmol). The flask was cooled to −78° C. for 10 minutes, after which butyllithium (2.5M in hexanes) (0.385 ml, 0.961 mmol) was added dropwise. After 30 minutes the dry-ice bath was removed, and 2N aq NaOH (10 mL), and the resulting biphasic mixture was stirred vigorously. After 1 h, the mixture was diluted with water, and the layers separated. The ether was then extracted with water (×2) and the water layers were combined, and washed with ether. The ether layers were back-extracted once more, and all aqueous layers combined and neutralized to ~pH=7 with 1N aq HCl to give a clear solution. The aqueous was extracted with DCM (×3) and the combined organics were dried over sodium sulfate, filtered and concentrated. The dried residue was taken up in DCM, and concentrated to give (2-(pyridin-4-yl)-4-(trifluoromethyl)phenyl)boronic acid (0.136 g, 0.509 mmol, 63.6% yield) as an off-white solid. [M+H]+=268.1

Step 1

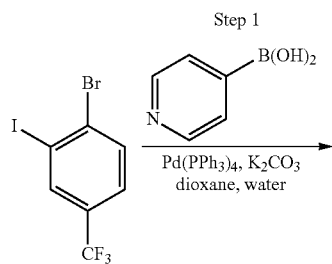

Step 2

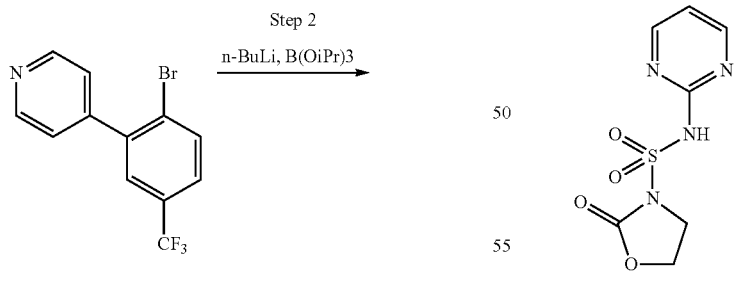

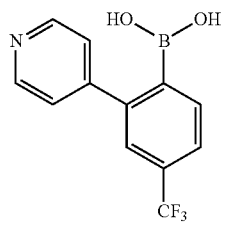

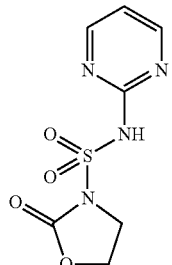

Intermediate Q: 2-Oxo-N-(pyrimidin-2-yl)oxazolidine-3-sulfonamide

In a 200-mL round-bottom flask was charged with DCM (50 mL) and chlorosulfonyl isocyanate (0.913 ml, 10.51 mmol). The flask was cooled in an ice-bath for 20 min, then 2-bromoethanol (0.745 ml, 10.51 mmol) was added dropwise. The mixture was stirred for 2.5 h, then a solution of pyrimidin-2-amine (1.00 g, 10.51 mmol) and triethylamine (4.40 ml, 31.5 mmol) in DCM (30 mL) was added dropwise via an addition funnel over 10 min. When the addition was complete, the cooling bath was removed, and the mixture was stirred for 2 days. The mixture was washed with 2 N aq. HCl, and the aq. layer was extracted with DCM. The combined organic extracts were dried over sodium sulfate, filtered, and concentrated. The mixture was taken up in a mixture of DCM and EtOAc, then filtered and dried under a stream of nitrogen to give 2-oxo-N-(pyrimidin-2-yl)oxazolidine-3-sulfonamide (0.930 g, 3.81 mmol, 36.2) as a cream-colored solid. $^1$H NMR (400 MHz, DMSO-$d_6$) δ ppm=12.98 (br. s, 1H), 8.66 (s, 2H), 7.13 (t, J=5.0 Hz, 1H), 4.44-4.18 (m, 4H).

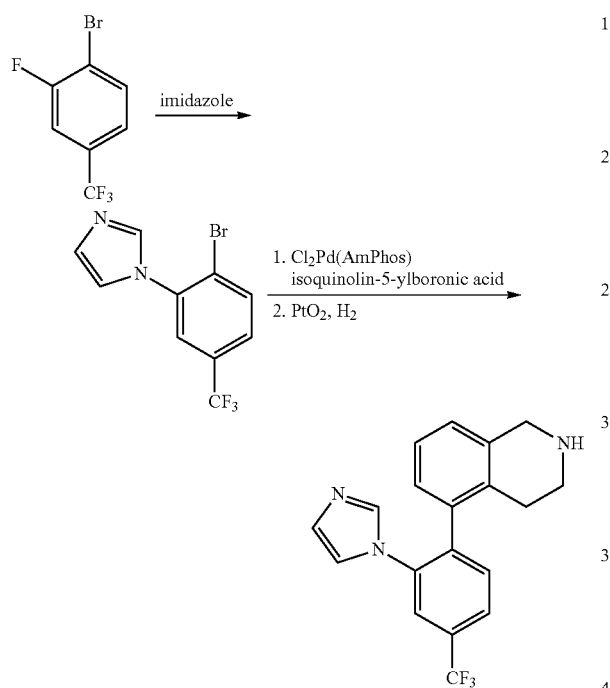

Intermediate R: 8-(2-(1H-Imidazol-1-yl)-4-(trifluoromethyl)phenyl)-1,2,3,4-tetrahydroisoquinoline Step 1:
1-(2-Bromo-5-(trifluoromethyl)phenyl)-1H-imidazole A solution of 1H-imidazole (0.420 g, 6.17 mmol) in 12 mL dioxane was treated with sodium ethoxide (0.441 g, 6.48 mmol) and was allowed to stir for 30 minutes. 1-Bromo-2-fluoro-4-(trifluoromethyl)benzene (0.885 ml, 6.17 mmol) was added and the reaction mixture was heated to 120° C. in a sealed vial overnight. The reaction mixture was poured into water and was extracted with EtOAc. The organics were concentrated and purified directly by reverse phase column chromatography [RediSep Gold C-18 100 g (Teledyne Isco, Lincoln, Nebr.), 10 to 100% (0.1% NH4OH in MeOH)/(0.1% NH4OH in water)] yielding 1-(2-bromo-5-(trifluoromethyl) phenyl)-1H-imidazole (0.400 g, 1.374 mmol).

Step 2: 8-(2-(1H-Imidazol-1-yl)-4-(trifluoromethyl) phenyl)-1,2,3,4-tetrahydroisoquinoline A solution of Cl$_2$Pd(AmPhos) (Sigma-Aldrich, St. Louis, Mo., 0.049 g, 0.069 mmol), isoquinolin-5-ylboronic acid (Frontier Scientific, Logan, Utah, 0.297 g, 1.718 mmol), 1-(2-bromo-5-(trifluoromethyl)phenyl)-1H-imidazole (0.400 g, 1.374 mmol), and potassium phosphate (1.167 g, 5.50 mmol) in 6 mL dioxane 3 mL water was heated to 120° C. overnight. The reaction mixture was diluted with diethyl ether. The organics were separated and concentrated. The resulting residue was taken up in 6 mL MeOH, was treated with platinum (IV) oxide (0.031 g, 0.137 mmol) and acetic acid (0.236 ml, 4.12 mmol) and was placed under 45 psi (4559.6 kpa) H$_2$ for 2 hours. The reaction mixture was filtered through a plug of diatomaceous earth eluting with EtOAc. The filtrate was washed with saturated NaHCO$_3$ solution, the organics dried over MgSO$_4$ and concentrated yielding 5-(2-(1H-imidazol-1-yl)-4-(trifluoromethyl)phenyl)-1,2,3,4-tetrahydroisoquinoline (0.450 g, 1.311 mmol). [M+H]+=344.0

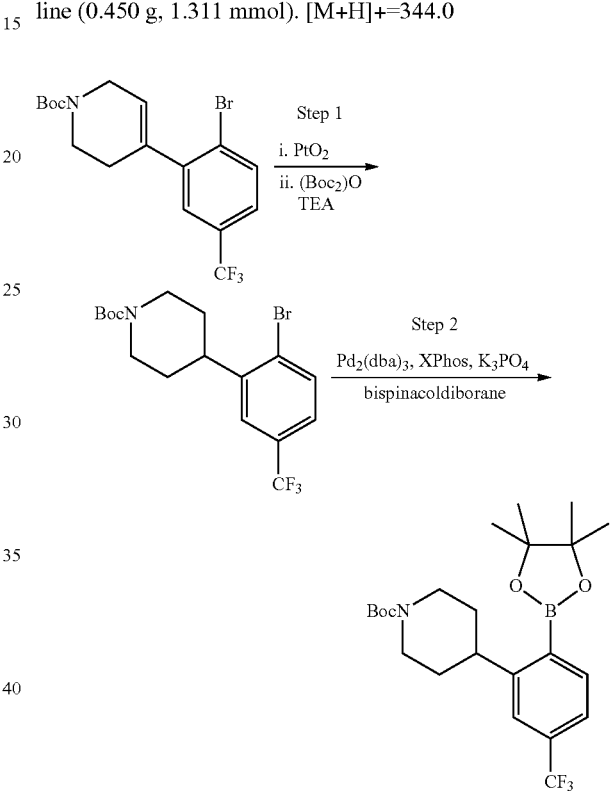

Intermediate S: tert-Butyl 4-(2-(4,4,5,5-tetramethyl-1,3,2-dioxaborolan-2-yl)-5-(trifluoromethyl)phenyl) piperidine-1-carboxylate Step 1: tert-Butyl 4-(2-bromo-5-(trifluoromethyl) phenyl)piperidine-1-carboxylate A solution of tert-butyl 4-(2-bromo-5-(trifluoromethyl) phenyl)-5,6-dihydropyridine-1(2H)-carboxylate (Intermediate J, 8.45 g, 20.80 mmol) and platinum(IV) oxide (0.472 g, 2.080 mmol) in 40 mL MeOH was placed under 45 psi (4559.6 kpa) H$_2$ for 2 hours. The reaction mixture was filtered through a plug of diatomaceous earth and was concentrated. The resulting residue was taken up in 10 mL THF, was treated with di-tert-butyl dicarbonate (10.40 ml, 10.40 mmol) followed by triethylamine (2.90 ml, 20.80 mmol) and was allowed to stir for 4 hours. Concentration and purification of the resulting residue by silica gel column chromatography (0 to 10% EtOAc/heptane) gave tert-butyl 4-(2-bromo-5-(trifluoromethyl)phenyl)piperidine-1-carboxylate (4.812 g, 11.79 mmol) as a clear oil. [M+Na]+=432.0

Step 2: tert-Butyl 4-(2-(4,4,5,5-tetramethyl-1,3,2-dioxaborolan-2-yl)-5-(trifluoromethyl)phenyl)piperidine-1-carboxylate A solution of X-Phos (Sigma-Aldrich, St. Louis, Mo., 0.562 g, 1.179 mmol), Pd$_2$(dba)$_3$ (Strem Chemicals Inc., Newburyport, Mass., 0.069 g, 0.295 mmol), bis(pinacolato)diboron (Sigma-Aldrich, St. Louis, Mo., 0.89 g, 15.32 mmol), tert-butyl 4-(2-bromo-5-(trifluoromethyl)phenyl)piperidine-1-carboxylate (4.81 g, 11.79 mmol), and potassium phosphate (10.01 g, 47.1 mmol) in 100 mL DME was heated to 100° C. overnight. The reaction mixture was allowed to cool to room temperature and was diluted with diethyl ether. The reaction mixture was filtered through a plug of diatomaceous earth and was concentrated. Purification of the resulting residue by silica gel column chromatography (0 to 10% EtOAc/heptane) gave tert-butyl 4-(2-(4,4,5,5-tetramethyl-1,3,2-dioxaborolan-2-yl)-5-(trifluoromethyl)phenyl)piperidine-1-carboxylate (2.22 g, 4.88 mmol). [M+Na]+=477.9

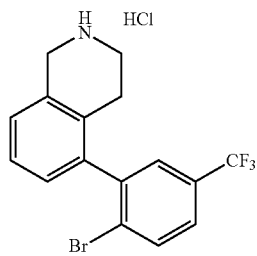 [SMILES: Cl ; FC(F)(F)c1ccc(Br)c(-c2cccc3c2CCNC3)c1]

Intermediate T: 5-(2-Bromo-5-(trifluoromethyl)phenyl)-1,2,3,4-tetrahydroisoquinoline hydrochloride The title compound was prepared in a procedure analogous to Intermediate D with the exception that 2-bromo-1-iodo-5-(trifluoromethyl)benzene was used in Step 1 instead of 2-bromo-1-iodo-4-(trifluoromethyl)benzene. [M+H]+=358.2

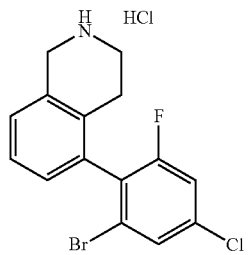 [SMILES: Cl ; Fc1cc(Cl)cc(Br)c1-c1cccc2c1CCNC2]

Intermediate U: 5-(2-Bromo-4-chloro-6-fluorophenyl)-1,2,3,4-tetrahydroisoquinoline hydrochloride The title compound was prepared in a procedure analogous to Intermediate D with the exception that 2-bromo-4-chloro-6-fluoro-1-iodobenzene was used in step 1 instead of 2-bromo-1-iodo-4-(trifluoromethyl)benzene. [M+H]+=342.0

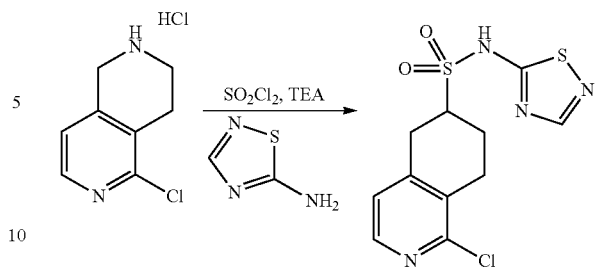

Intermediate V: 5-Chloro-N-(1,2,4-thiadiazol-5-yl)-3,4-dihydro-2,6-naphthyridine-2(1H)-sulfonamide A solution of 1,2,4-thiadiazol-5-amine (0.740 g, 7.31 mmol) and triethylamine (3.06 ml, 21.94 mmol) in 20 mL DCM was cooled to −78° C. and was treated with sulfuryl chloride (0.595 ml, 7.31 mmol). The cooling bath was removed, and the reaction mixture was allowed to stir for 20 minutes. LC/MS showed mostly desired intermediate, so 5-chloro-1,2,3,4-tetrahydro-2,6-naphthyridine hydrochloride (Anichem, North Brunswick, N.J., 0.750 g, 3.66 mmol) was added and the reaction mixture was allowed to stir for one hour. The reaction mixture was then poured into 1N citric acid and was extracted with EtOAc. The organics were concentrated. Purification of the resulting residue by silica gel column chromatography (0 to 100% EtOAc/heptane) gave 5-chloro-N-(1,2,4-thiadiazol-5-yl)-3,4-dihydro-2,6-naphthyridine-2(1H)-sulfonamide (1.064 g, 3.21 mmol). [M+H]+=332.1

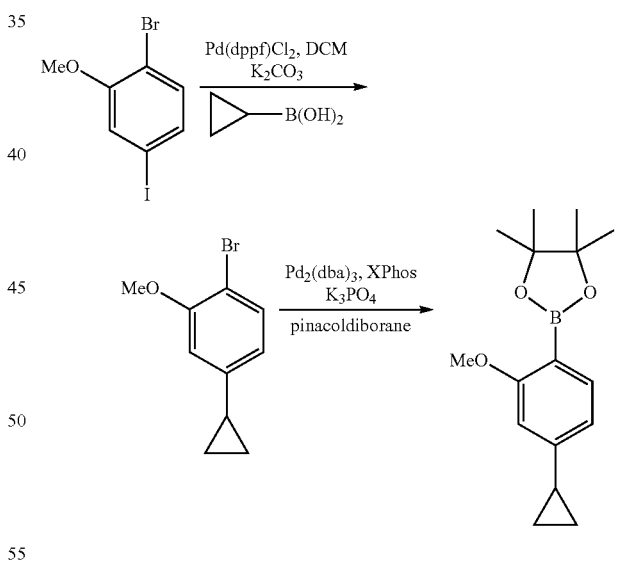

Intermediate W: 2-(4-Cyclopropyl-2-methoxyphenyl)-4,4,5,5-tetramethyl-1,3,2-dioxaborolane A solution of PdCl$_2$(dppf)-CH$_2$Cl$_2$adduct (1.391 g, 1.703 mmol), cyclopropylboronic acid (Frontier Scientific, Logan, Utah, 4.39 g, 51.1 mmol), 1-bromo-4-iodo-2-methoxybenzene (Combi-Blocks, San Diego, Calif., 10.66 g, 34.1 mmol), and potassium carbonate (18.83 g, 136 mmol) in 100 mL dioxane and 50 mL water was heated to 120° C. for 8 hours. The reaction mixture was diluted with heptane and was washed with saturated NaHCO$_3$ solution. The organics were dried over MgSO₄ and concentrated. The resulting residue was taken up in 100 mL dioxane, was treated with Pd₂(dba)₃ (0.399 g, 1.703 mmol), dicyclohexyl(2',4',6'-triisopropyl-[1,1'-biphenyl]-2-yl)phosphine (4.06 g, 8.52 mmol), bis(pinacolato)diboron (12.98 g, 51.1 mmol), and potassium phosphate (28.9 g, 136 mmol) and was heated to 120° C. overnight. The reaction mixture was then diluted with heptane and filtered through a plug of diatomaceous earth. The filtrate was concentrated then purified directly by silica gel column chromatography (0 to 25% EtOAc/heptane) yielding 2-(4-cyclopropyl-2-methoxyphenyl)-4,4,5,5-tetramethyl-1,3,2-dioxaborolane (2.68 g, 9.78 mmol). [M+H]+=275.1

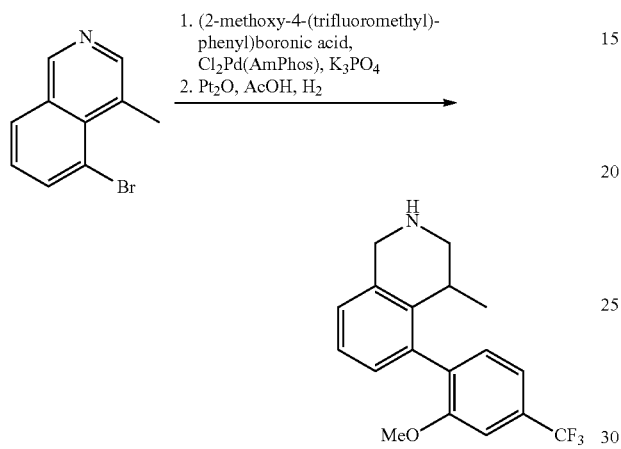

Intermediate X: 5-(2-Methoxy-4-(trifluoromethyl) phenyl)-4-methyl-1,2,3,4-tetrahydroisoquinoline A solution of Cl₂Pd(AmPhos) (Sigma-Aldrich, St. Louis, Mo., 0.319 g, 0.450 mmol), 5-bromo-4-methylisoquinoline (Frontier Scientific, Logan, Utah, 1.000 g, 4.50 mmol), (2-methoxy-4-(trifluoromethyl)phenyl)boronic acid (Combi-Blocks, San Diego, Calif., 0.990 g, 4.50 mmol), and potassium phosphate (3.82 g, 18.01 mmol) in 10 mL dioxane 5 mL water was heated to 80° C. for overnight. The reaction mixture was diluted with heptane, and the organics were separated then concentrated. The resulting residue was dissolved in 10 mL MeOH, was treated with platinum(IV) oxide (0.102 g, 0.450 mmol) and TFA (0.694 ml, 9.01 mmol) and was placed under 45 psi (4559.6 kpa) H₂ overnight. LC/MS showed incomplete reaction, so an additional portion of platinum(IV) oxide (0.102 g, 0.450 mmol) and TFA (0.694 ml, 9.01 mmol) were added, and the reaction mixture was placed under 45 psi (4559.6 kpa) H₂ for an additional 6 hours. The reaction mixture was then filtered through diatomaceous earth. The filtrate was poured into saturated NaHCO₃ solution and extracted with EtOAc. The organics were dried over MgSO₄ and concentrated yielding racemic 5-(2-methoxy-4-(trifluoromethyl)phenyl)-4-methyl-1,2,3,4-tetrahydroisoquinoline (1.810 g, 5.63 mmol). [M+H]+=322.2

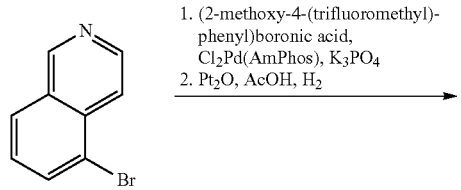

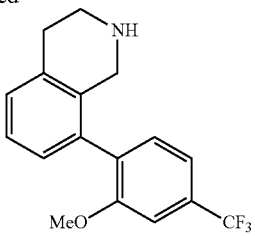

Intermediate Y: 8-(2-Methoxy-4-(trifluoromethyl) phenyl)-1,2,3,4-tetrahydroisoquinoline The title compound was prepared in an analogous manner to Intermediate X except 8-bromoisoquinoline (Synthonix, Inc., Wake Forest, N.C.) was used in place of 5-bromo-4-methylisoquinoline. [M+H]+=308.1

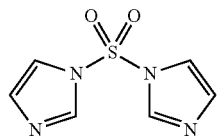 [SMILES: O=S(=O)(n1ccnc1)n1ccnc1]

Intermediate Z: 1,1'-Sulfonylbis(1H-imidazole)

A solution of 1H-imidazole (5.00 g, 73.4 mmol) in 100 mL DCM was cooled to −78° C. and was treated with sulfuryl chloride (1.493 ml, 18.36 mmol). The reaction mixture was allowed to slowly warm to room temperature overnight. The reaction mixture was diluted with diethyl ether and filtered through a plug of diatomaceous earth. The filtrate was concentrated yielding 1,1'-sulfonylbis(1H-imidazole) (3.47 g, 17.51 mmol). [M+H]+=198.9. This intermediate was used without further purification.

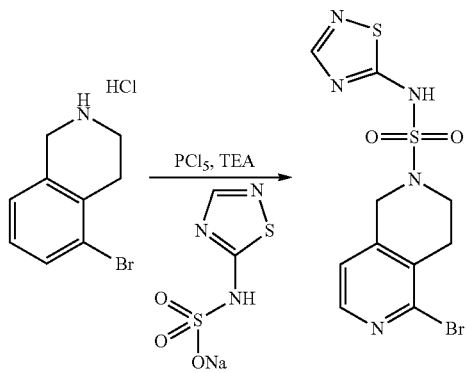

Intermediate AA: 5-Bromo-N-(1,2,4-thiadiazol-5-yl)-3,4-dihydroisoquinoline-2(1H)-sulfonamide To a 50 mL flask containing sodium 1,2,4-thiadiazol-5-ylsulfamate (Intermediate A, 96 mg, 0.472 mmol) and 10 mL of DCM was added PCl₅ (Aldrich, St. Louis, Mo., 245 mg, 1.179 mmol). The resulting slurry was heated at 50° C. for 1.5 hours. LCMS showed conversion to the methyl sulfamate (following quench into methanol). The reaction was cooled to rt and was quenched with the addition of 5 drops of brine. The resulting slurry was stirred vigorously for 5 minutes before being filtered through a plug of diatomaceous earth, washing well with DCM. The mixture was concentrated under reduced pressure. The derived oil was taken up in 1 mL of DCM and was added to a solution of 5-bromo-1,2,3,4-tetrahydroisoquinoline hydrochloride (ASW Medchem, 50 mg, 0.236 mmol) and TEA (164 µl, 1.179 mmol) in 2 mL of DCM at 0° C. Another 0.164 mL of TEA was added and the reaction allowed to warm to room temperature where it was maintained for 2 hours. LCMS showed clean conversion to sulfonamide. The reaction was allowed to stir overnight before being diluted with saturated sodium bicarbonate (10 mL) and poured into a separatory funnel containing methylenechloride (10 mL). The layers were separated and the aqueous layer was extracted with methylenechloride (2×25 mL). The combined organic layers were washed with brine, dried over sodium sulfate, filtered and concentrated under a vacuum to provide a yellow oil that was purified by silica gel chromatography (Redi-Sep pre-packed silica gel column (12 g), 0-10% methanol in methylenechloride) to provide 5-bromo-N-(1,2,4-thiadiazol-5-yl)-3,4-dihydroisoquinoline-2(1H)-sulfonamide as an off white solid. [M+H]+=375.0 $^1$H NMR (400 MHz, Acetone) δ ppm 8.28 (s, 1H), 7.96 (s, 1H), 7.45-7.50 (m, 1H), 7.09-7.20 (m, 2H), 4.32 (s, 2H), 3.48 (t, J=6.1 Hz, 2H), 2.86-2.92 (m, 2H)

(2-(1-methyl-1H-pyrazol-5-yl)-4-(trifluoromethyl)phenyl) boronic acid (Intermediate B, 66.2 mg, 0.245 mmol) and 5-bromo-N-(1,2,4-thiadiazol-5-yl)-3,4-dihydroisoquinoline-2(1H)-sulfonamide (Intermediate AA), 46 mg, 0.123 mmol) were combined in a sealed tube. 3 mL of dioxane and 0.8 mL of water were added, and the reaction mixture was flushed with argon, sealed and heated at 100° C. for 2 hours. The reaction was diluted with saturated sodium bicarbonate (25 mL) and poured into a separatory funnel containing methylene chloride (25 mL). The layers were separated and the aqueous layer was extracted with methylenechloride (3×25 mL). The combined organic layers were washed with brine, dried over sodium sulfate, filtered and concentrated under a vacuum to provide a yellow oil that was purified by silica gel chromatography (40 g), 0 to 10% methanol in methylenechloride to provide product.

The resulting material was taken up in 5 mL of acetonitrile and loaded onto a PE-AX anion exchange column. The column was flushed with MeCN before the product was eluted with HCl in DCM/MeOH. [2 mL of AcCl was added to a solution of 15 mL of MeOH at 0° C. This mixture was then diluted up to 30 mL with DCM.]

The fractions were concentrated to provide 5-(2-(1-methyl-1H-pyrazol-5-yl)-4-(trifluoromethyl)phenyl)-N-(1,2,4-thiadiazol-5-yl)-3,4-dihydroisoquinoline-2(1H)-sulfonamide as a pale yellow solid. [M+H]+=521.0 $^1$H NMR (400 MHz, DMSO-d$_6$) δ ppm: 8.42 (s, 1H), 7.82-7.92 (m, 2H), 7.61 (d, J=8.0 Hz, 1H), 7.27 (d, J=1.9 Hz, 1H), 7.10-7.16 (m, 2H), 6.93 (dd, J=6.1, 2.9 Hz, 1H), 5.95 (d, J=1.9 Hz, 1H), 4.15-4.30 (m, 2H), 3.24-3.35 (m, 1H), 2.94-3.07 (m, 1H), 2.61-2.74 (m, 1H), 2.21-2.36 (m, 1H)

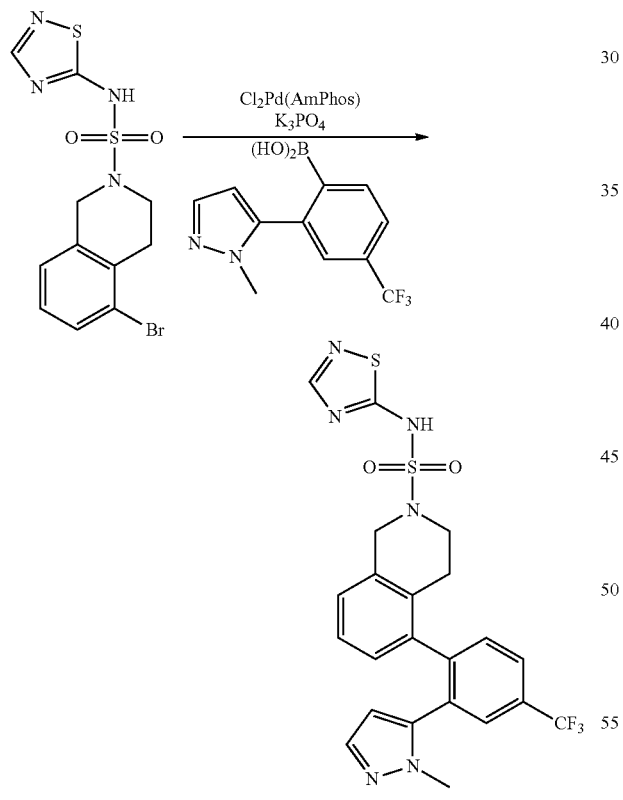

Example 1

5-(2-(1-Methyl-1H-pyrazol-5-yl)-4-(trifluoromethyl)phenyl)-N-(1,2,4-thiadiazol-5-yl)-3,4-dihydroisoquinoline-2(1H)-sulfonamide Potassium phosphate (64.1 mg, 0.368 mmol), Cl$_2$Pd(AmPhos) (Sigma-Aldrich, St. Louis, Mo., 8.68 mg, 0.012 mmol),

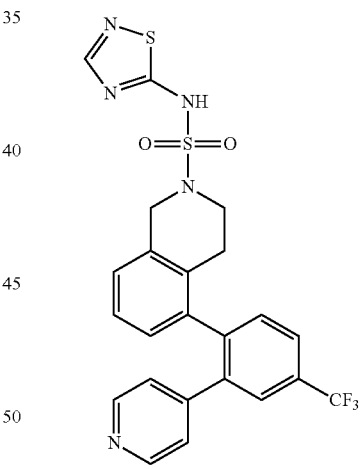

Example 2

5-(2-(Pyridin-4-yl)-4-(trifluoromethyl)phenyl)-N-(1,2,4-thiadiazol-5-yl)-3,4-dihydroisoquinoline-2(1H)-sulfonamide The title compound was prepared in a manner analogous to Example 1 utilizing (2-(pyridin-4-yl)-4-(trifluoromethyl)phenyl)boronic acid (Intermediate P) in place of (2-(1-methyl-1H-pyrazol-5-yl)-4-(trifluoromethyl)phenyl)boronic acid. [M+H]+=518.0. $^1$H NMR (400 MHz, Acetone-d$_6$) δ ppm: 8.43 (d, J=6.1 Hz, 2H), 8.03 (s, 1H), 7.82-7.87 (m, 2H), 7.60 (d, J=8.0 Hz, 1H), 7.09-7.18 (m, 4H), 6.96-6.99 (m, 1H), 4.29 (d, J=15.3 Hz, 1H), 4.18 (d, J=15.8 Hz, 1H), 3.24-3.33 (m, 1H), 2.93-3.14 (m, 1H), 2.57-2.75 (m, 1H), 2.28-2.36 (m, 1H)

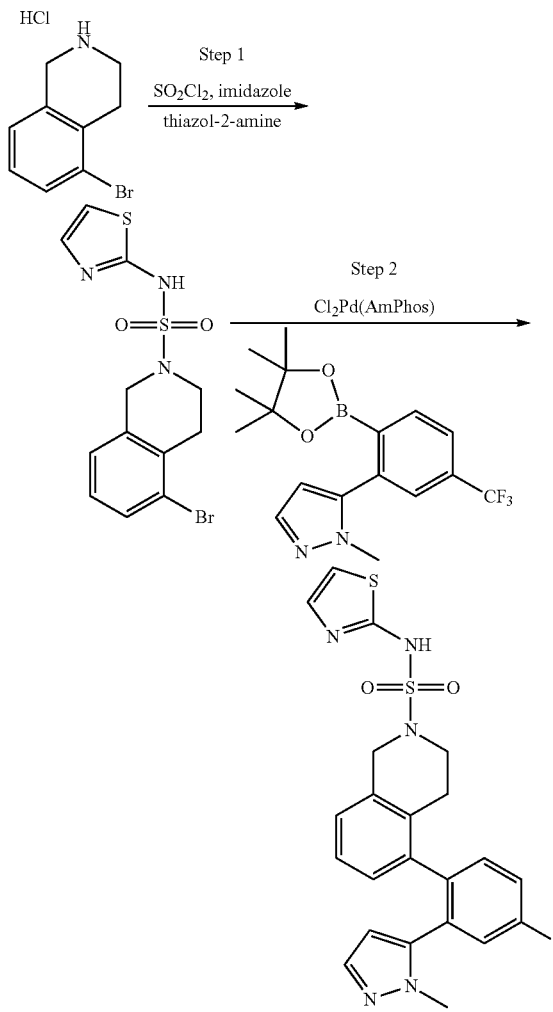

Example 3

5-(2-Bromo-4-(trifluoromethyl)phenyl)-N-(thiazol-2-yl)-3,4-dihydroisoquinoline-2(1H)-sulfonamide Step 1: 5-Bromo-N-(thiazol-2-yl)-3,4-dihydroisoquinoline-2(1H)-sulfonamide A solution of imidazole (1.530 g, 22.47 mmol) and thiazol-2-amine (0.750 g, 7.49 mmol) in 8 mL DCM was cooled to −78° C. and was treated with sulfuryl chloride (0.609 ml, 7.49 mmol). After stirring for 20 minutes, the cooling bath was removed and the reaction mixture was allowed to stir for an additional 30 minutes. 5-Bromo-1,2,3,4-tetrahydroisoquinoline hydrochloride (ASW Medchem, Brunswick, N.J., 1.396 g, 5.62 mmol) was added, followed by triethylamine (7.31 ml, 52.4 mmol). The reaction mixture was then heated to 80° C. for 30 minutes. The mixture was cooled to rt and poured into 1N citric acid solution before being extracted into EtOAc. The organics were dried over MgSO4 and concentrated. Purification of the residue by silica gel column chromatography (0 to 100% EtOAc/heptane) gave 5-bromo-N-(thiazol-2-yl)-3,4-dihydroisoquinoline-2(1H)-sulfonamide (1.092 g, 2.92 mmol). [M+H]+=375.6.

Step 2: 5-(2-Bromo-4-(trifluoromethyl)phenyl)-N-(thiazol-2-yl)-3,4-dihydroisoquinoline-2(1H)-sulfonamide A solution of Cl2Pd(AmPhos) (Sigma-Aldrich, St. Louis, Mo., 0.023 g, 0.032 mmol), 1-methyl-5-(2-(4,4,5,5-tetramethyl-1,3,2-dioxaborolan-2-yl)-5-(trifluoromethyl)phenyl)-1H-pyrazole (Intermediate O, 0.169 g, 0.481 mmol), 5-bromo-N-(thiazol-2-yl)-3,4-dihydroisoquinoline-2(1H)-sulfonamide (0.120 g, 0.321 mmol), and potassium phosphate (0.272 g, 1.282 mmol) in 2.5 mL dioxane, 1.0 mL water was heated to 100° C. 4 hours. The reaction mixture was diluted with EtOAc and washed with 1 N citric acid solution. The organics were dried over MgSO4 and concentrated. Purification of the resulting residue by silica gel column chromatography (0 to 100% EtOAc/heptane) gave 5-(2-(1-methyl-1H-pyrazol-5-yl)-4-(trifluoromethyl)phenyl)-N-(thiazol-2-yl)-3,4-dihydroisoquinoline-2(1H)-sulfonamide (0.053 g, 0.102 mmol). [M+H]+=519.8 1H NMR (400 MHz, Acetone-d6) δ ppm: 7.88 (dd, J=8.0, 1.4 Hz, 1H), 7.81 (s, 1H), 7.63 (d, J=8.0 Hz, 1H), 7.25 (d, J=2.0 Hz, 1H), 7.09-7.17 (m, 3H), 6.98-7.01 (m, 1H), 6.71 (d, J=4.7 Hz, 1H), 6.00 (d, J=2.0 Hz, 1H), 4.31 (d, J=15.7 Hz, 1H), 4.24 (d, J=15.7 Hz, 1H), 3.30-3.38 (m, 1H), 3.12 (m, 1H), 2.63-2.74 (m, 1H), 2.36-2.46 (m, 1H)

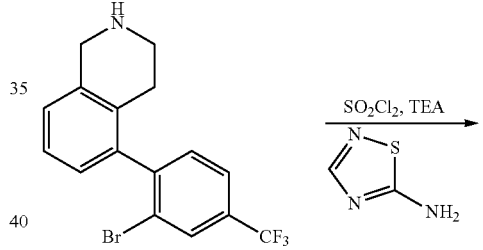

Example 4

5-(2-Bromo-4-(trifluoromethyl)phenyl)-N-(1,2,4-thiadiazol-5-yl)-3,4-dihydroisoquinoline-2(1H)-sulfonamide A suspension of 1,2,4-thiadiazol-5-amine (2.67 g, 26.4 mmol) in 20 mL DCM was treated with triethylamine (3.68 ml, 26.4 mmol) and was allowed to stir for 10 minutes. The reaction mixture was then cooled to −78° C. and was treated with 1 equivalent of sulfuryl chloride. After stirring for 5 minutes, the cooling bath was removed, and the reaction mixture was allowed to stir for an additional hour. LC/MS showed mostly product so the reaction mixture was filtered then concentrated. The resulting residue was dissolved in 10 mL THF and was added to a solution of 5-(2-bromo-4-(trifluoromethyl)phenyl)-1,2,3,4-tetrahydroisoquinoline hydrochloride (Intermediate D, 4.70 g, 13.20 mmol) and triethylamine (4.05 ml, 29.0 mmol) in 10 mL THF. After stirring for an additional 4 hours, the reaction mixture was poured into 1 N citric acid solution and was extracted with EtOAc. The organics were washed with brine, dried over MgSO₄ and concentrated. The resulting residue was triturated with DCM providing a white solid. The washings were purified by silica gel column chromatography (0 to 100% EtOAc/heptane) and combined with the white solid yielding 5-(2-bromo-4-(trifluoromethyl)phenyl)-N-(1,2,4-thiadiazol-5-yl)-3,4-dihydroisoquinoline-2(1H)-sulfonamide (6.90 g, 13.29 mmol). [M+H]⁺=518.9 ¹H NMR (400 MHz, Acetone-d₆) δ ppm: 8.04 (s, 1H), 7.97 (s, 1H), 7.81 (d, J=7.9 Hz, 1H), 7.54 (d, J=7.9 Hz, 1H), 7.28 (t, J=7.5 Hz, 1H), 7.22 (d, J=7.1 Hz, 1H), 7.01 (d, J=6.1 Hz, 1H), 4.34 (s, 2H), 3.30 (m, 2H), 2.47-2.58 (m, 2H)

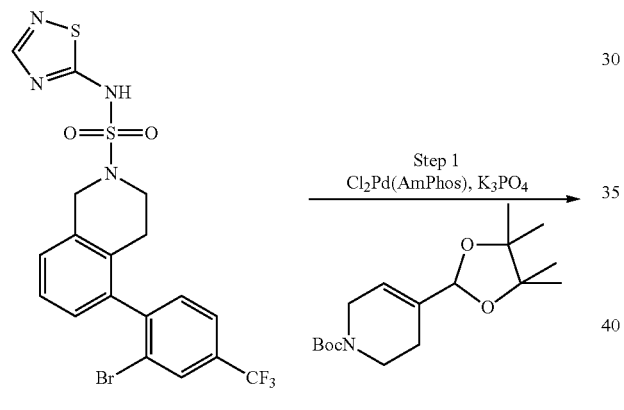

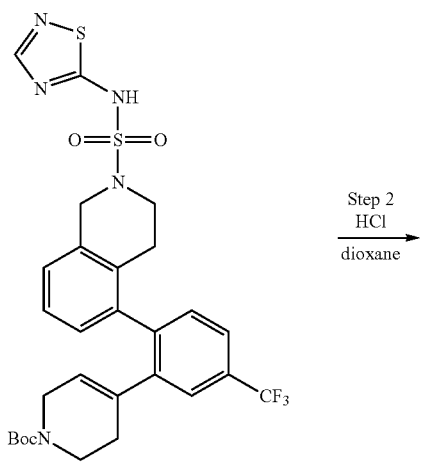

Example 5

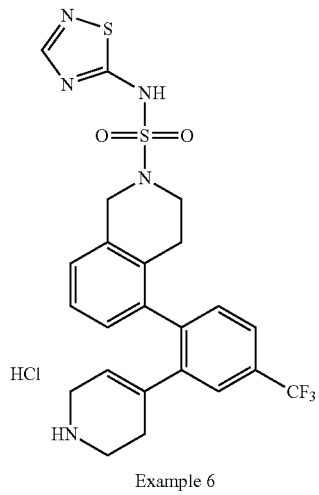

Example 6

Examples 5 and 6 tert-Butyl 4-(2-(2-(N-(1,2,4-thiadiazol-5-yl)sulfamoyl)-1,2,3,4-tetrahydroisoquinolin-5-yl)-5-(trifluoromethyl)phenyl)-5,6-dihydropyridine-1(2H)-carboxylate and 5-(2-(1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide hydrochloride

Step 1: tert-Butyl 4-(2-(2-(N-(1,2,4-thiadiazol-5-yl)sulfamoyl)-1,2,3,4-tetrahydroisoquinolin-5-yl)-5-(trifluoromethyl)phenyl)-5,6-dihydropyridine-1(2H)-carboxylate (Example 5)

A solution of Cl₂Pd(AmPhos) (Sigma-Aldrich, St. Louis, Mo., 0.136 g, 0.193 mmol), tert-butyl 4-(4,4,5,5-tetramethyl-1,3,2-dioxaborolan-2-yl)-5,6-dihydropyridine-1(2H)-carboxylate (Frontier Scientific, Logan, Utah, 1.191 g, 3.85 mmol), 5-(2-bromo-4-(trifluoromethyl)phenyl)-N-(1,2,4-thiadiazol-5-yl)-3,4-dihydroisoquinoline-2(1H)-sulfonamide (Example 4, 1.000 g, 1.925 mmol), and potassium phosphate (1.635 g, 7.70 mmol) in 20 mL dioxane, 10 mL water was heated to 120° C. for 2 hours. The reaction mixture was diluted with EtOAc and washed with 1 N citric acid solution. The organics were dried over MgSO₄ and concentrated. Purification of the resulting residue by silica gel column chromatography (0 to 100% EtOAc/heptane) gave tert-butyl 4-(2-(2-(N-(1,2,4-thiadiazol-5-yl)sulfamoyl)-1,2,3,4-tetrahydroisoquinolin-5-yl)-5-(trifluoromethyl)phenyl)-5,6-dihydropyridine-1(2H)-carboxylate (0.635 g, 1.021 mmol). [M+H]⁺=522.0 ¹H NMR (400 MHz, Acetone-d₆) δ ppm: 8.28 (s, 1H), 7.63-7.70 (m, 2H), 7.43 (d, J=7.8 Hz, 1H), 7.15-7.30 (m, 2H), 7.07 (d, J=7.4 Hz, 1H), 5.72 (s, 1H), 4.31-4.44 (m, 2H), 3.87 (br. s., 2H), 3.41-3.48 (m, 1H), 3.16-3.36 (m, 1H), 2.78 (br. s., 4H), 2.69 (m, 1H), 2.48-2.55 (m, 1H), 1.37-1.47 (m, 9H)

Step 2: 5-(2-(1,2,3,6-Tetrahydropyridin-4-yl)-4-(trifluoromethyl)phenyl)-N-(1,2,4-thiadiazol-5-yl)-3,4-dihydroisoquinoline-2(1H)-sulfonamide hydrochloride (Example 6)

A vial charged with tert-butyl 4-(2-(2-(N-(1,2,4-thiadiazol-5-yl)sulfamoyl)-1,2,3,4-tetrahydroisoquinolin-5-yl)-5-(trifluoromethyl)phenyl)-5,6-dihydropyridine-1(2H)-carboxylate (0.305 g, 0.491 mmol) was treated with HCl 4N in dioxane (3.07 ml, 12.26 mmol) then was heated to 80° C. for one hour. The reaction mixture was cooled to room temperature and was diluted with diethyl ether. The resulting white solid was filtered off and dried yielding 5-(2-(1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide hydrochloride (0.242 g, 0.434 mmol). [M+H]$^+$=522.0. $^1$H NMR (400 MHz, DMSO-d$_6$) δ ppm: 8.81 (br. s., 2H), 8.35-8.44 (m, 1H), 7.73 (d, J=8.0 Hz, 1H), 7.60 (d, J=1.3 Hz, 1H), 7.42 (d, J=7.8 Hz, 1H), 7.18-7.28 (m, 2H), 7.02 (d, J=6.6 Hz, 1H), 5.72 (br. s., 1H), 4.22-4.36 (m, 2H), 3.31-3.52 (m, 4H), 3.26 (m, 2H), 2.83-3.08 (m, 2H), 1.91-2.20 (m, 2H)

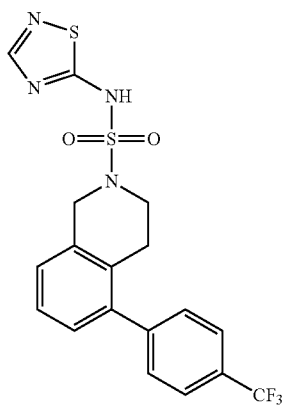 [SMILES: O=S(=O)(Nc1ncns1)N1CCc2c(cccc2-c2ccc(C(F)(F)F)cc2)C1]

Example 7

N-(1,2,4-Thiadiazol-5-yl)-5-(4-(trifluoromethyl)phenyl)-3,4-dihydroisoquinoline-2(1H)-sulfonamide A vial charged with Cl$_2$Pd(AmPhos) (Sigma-Aldrich, St. Louis, Mo., 9.43 μg, 0.013 μmol), (4-(trifluoromethyl)phenyl)boronic acid (0.200 μmol), 5-bromo-N-(1,2,4-thiadiazol-5-yl)-3,4-dihydroisoquinoline-2(1H)-sulfonamide (0.050 mg, 0.133 μmol), and potassium phosphate (0.085 mg, 0.400 μmol) was treated with 2 mL dioxane and 1 mL water. The reaction mixture was heated to 120° C. for 2 hours at which time the mixture was cooled to room temperature then concentrated and purified by reverse phase column chromatography [RediSep Gold C-18 50 g, 5 to 75% (0.1% NH$_4$OH in MeOH)/(0.1% NH$_4$OH in water)] to provide N-(1,2,4-thiadiazol-5-yl)-5-(4-(trifluoromethyl)phenyl)-3,4-dihydroisoquinoline-2(1H)-sulfonamide. [M+H]$^+$=441.0. $^1$H NMR (400 MHz, MeOH-d$_4$) δ ppm: 8.03 (s, 1H), 7.72 (d, J=8.1 Hz, 2H), 7.49 (d, J=7.9 Hz, 2H), 7.22-7.28 (m, 1H), 7.12 (dd, J=15.5, 7.1 Hz, 2H), 4.40 (s, 2H), 3.33-3.38 (m, 2H), 2.77 (m, 2H)

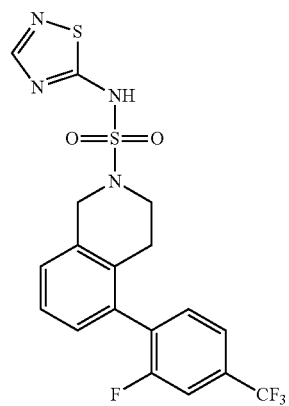 [SMILES: O=S(=O)(Nc1ncns1)N1CCc2c(cccc2-c2ccc(C(F)(F)F)cc2F)C1]

Example 8

5-(2-Fluoro-4-(trifluoromethyl)phenyl)-N-(1,2,4-thiadiazol-5-yl)-3,4-dihydroisoquinoline-2(1H)-sulfonamide The title compound was prepared in a manner analogous to Example 7 employing (2-fluoro-4-(trifluoromethyl)phenyl)boronic acid instead of (4-(trifluoromethyl)phenyl)boronic acid. [M+H]$^+$=459.0 $^1$H NMR (400 MHz, Acetone-d$_6$) δ ppm: 7.90 (s, 1H), 7.54-7.67 (m, 3H), 7.20-7.30 (m, 2H), 7.11 (d, J=6.3 Hz, 1H), 4.33 (s, 2H), 3.24-3.32 (m, 2H), 2.59-2.67 (m, 2H)

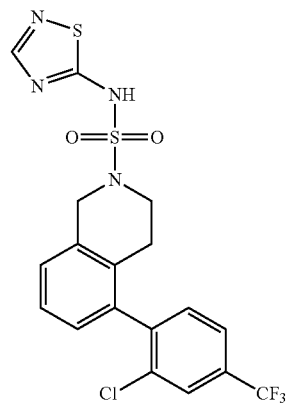 [SMILES: O=S(=O)(Nc1ncns1)N1CCc2c(cccc2-c2ccc(C(F)(F)F)cc2Cl)C1]

Example 9

5-(2-Chloro-4-(trifluoromethyl)phenyl)-N-(1,2,4-thiadiazol-5-yl)-3,4-dihydroisoquinoline-2(1H)-sulfonamide The title compound was prepared in a manner analogous to Example 7 employing (2-chloro-4-(trifluoromethyl)phenyl)boronic acid instead of (4-(trifluoromethyl)phenyl)boronic acid. [M+H]$^+$=475.0 $^1$H NMR (400 MHz, Acetone-d$_6$) δ ppm: 8.18 (s, 1H), 7.88 (s, 1H), 7.77 (d, J=7.6 Hz, 1H), 7.55 (d, J=8.3 Hz, 1H), 7.22-7.33 (m, 2H), 7.06 (d, J=7.1 Hz, 1H), 4.38 (s, 2H), 3.30-3.38 (m, 2H), 2.57 (m, 2H)

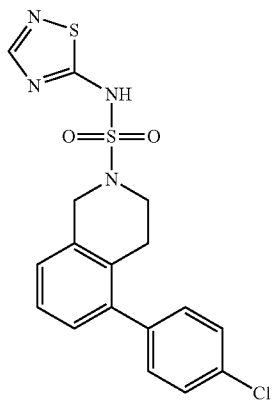 [SMILES: O=S(=O)(Nc1ncns1)N1CCc2c(cccc2-c2ccc(Cl)cc2)C1]

Example 10

5-(2-Chloro-4-(trifluoromethyl)phenyl)-N-(1,2,4-thiadiazol-5-yl)-3,4-dihydroisoquinoline-2(1H)-sulfonamide The title compound was prepared in a manner analogous to Example 7 employing (4-(trifluoromethyl)phenyl)boronic acid instead of (4-(trifluoromethyl)phenyl)boronic acid. [M+H]$^+$=407.0 $^1$H NMR (400 MHz, Acetone-d$_6$) δ ppm: 8.04 (s, 1H), 7.44-7.48 (m, 2H), 7.32-7.37 (m, 2H), 7.20-7.26 (m, 1H), 7.12-7.16 (m, 1H), 7.04-7.08 (m, 1H), 4.33 (s, 2H), 3.28 (t, J=5.9 Hz, 2H), 2.73 (t, J=5.8 Hz, 2H)

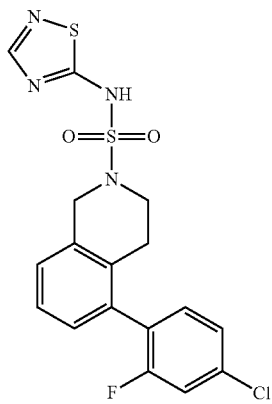 [SMILES: O=S(=O)(Nc1ncns1)N1CCc2c(cccc2-c2ccc(Cl)cc2F)C1]

Example 11

5-(4-Chloro-2-fluorophenyl)-N-(1,2,4-thiadiazol-5-yl)-3,4-dihydroisoquinoline-2(1H)-sulfonamide The title compound was prepared in a manner analogous to Example 7 employing (2-fluoro-4-chlorophenyl)boronic acid instead of (4-(trifluoromethyl)phenyl)boronic acid. [M+H]$^+$=425.0 $^1$H NMR (400 MHz, Acetone-d$_6$) δ ppm: 7.73 (s, 1H), 7.31-7.36 (m, 3H), 7.20-7.26 (m, 1H), 7.14-7.19 (m, 1H), 7.05 (d, J=6.7 Hz, 1H), 4.28 (s, 2H), 3.24 (t, J=5.6 Hz, 2H), 2.61 (t, J=5.5 Hz, 2H)

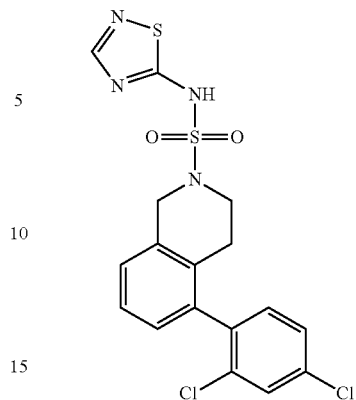

Example 12

5-(2,4-Dichlorophenyl)-N-(1,2,4-thiadiazol-5-yl)-3,4-dihydroisoquinoline-2(1H)-sulfonamide The title compound was prepared in a manner analogous to Example 7 employing (2,4-dichlorophenyl)boronic acid instead of (4-(trifluoromethyl)phenyl)boronic acid. [M+H]$^+$=441.0 $^1$H NMR (400 MHz, Acetone-d$_6$) δ ppm: 7.73 (s, 1H), 7.59 (d, J=2.2 Hz, 1H), 7.45 (dd, J=8.2, 2.1 Hz, 1H), 7.31 (d, J=8.2 Hz, 1H), 7.20-7.25 (m, 1H), 7.14-7.18 (m, 1H), 6.96 (d, J=7.3 Hz, 1H), 4.28 (s, 2H), 3.15-3.30 (m, 2H), 2.51 (t, J=5.9 Hz, 2H)

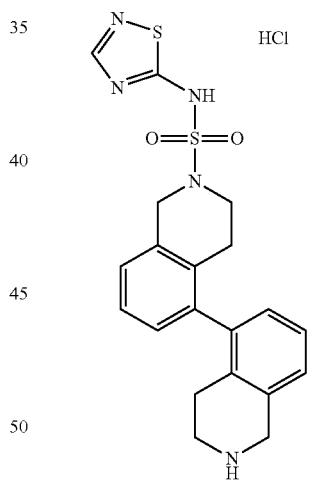

Example 13

N-(1,2,4-Thiadiazol-5-yl)-1',2',3,3',4,4'-hexahydro-[5,5'-biisoquinoline]-2(1H)-sulfonamide hydrochloride The title compound was prepared in a manner analogous to Example 7 employing tert-butyl 5-(4,4,5,5-tetramethyl-1,3,2-dioxaborolan-2-yl)-3,4-dihydroisoquinoline-2(1H)-carboxylate (ASW Medchem, Brunswick, N.J.) instead of (4-(trifluoromethyl)phenyl)boronic acid. The product obtained, (tert-butyl 2'-(N-(1,2,4-thiadiazol-5-yl)sulfamoyl)-1',2',3,3',4,4'-hexahydro-[5,5'-biisoquinoline]-2(1H)-carboxylate), was taken up in THF and treated with 10 equivalents of HCl (4M in dioxane). After stirring at rt overnight the mixture was concentrated to provide N-(1,2,4-thiadiazol-5-yl)-1',2',3,3',4,4'-hexahydro-[5,5'-biisoquinoline]-2(1H)-sulfonamide hydrochloride as a white solid. [M+H]$^+$=428.2 $^1$H NMR (400 MHz, DMSO-d$_6$) δ ppm: 9.07 (br. s., 2H), 8.39 (s, 1H), 7.29-7.37 (m, 1H), 7.18-7.29 (m, 3H), 7.07 (d, J=6.4 Hz, 1H), 6.93 (d, J=6.9 Hz, 1H), 4.23-4.38 (m, 4H), 3.19-3.46 (m, 8H)

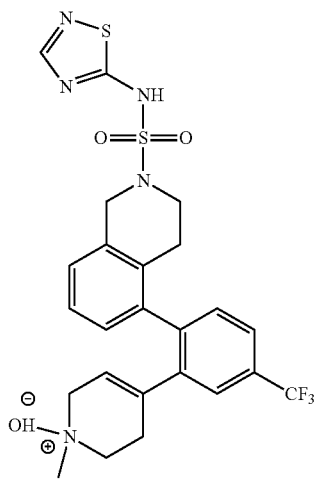 [SMILES: C[N+]1([O-])CC=C(c2cc(C(F)(F)F)ccc2-c2cccc3c2CCN(S(=O)(=O)Nc2ncns2)C3)CC1]

Example 14

4-(2-(2-(N-(1,2,4-Thiadiazol-5-yl)sulfamoyl)-1,2,3,4-tetrahydro isoquinolin-5-yl)-5-(trifluoromethyl)phenyl)-1,1-dimethyl-1,2,3,6-tetrahydropyridin-1-ium hydroxide A solution of 5-(2-(1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide hydrochloride (Example 6, 0.213 g, 0.382 mmol) and DIPEA (0.333 ml, 1.908 mmol) in 4 mL THF was treated with iodomethane (0.036 ml, 0.573 mmol) and was allowed to stir at room temperature overnight. The reaction mixture was concentrated. Purification of the resulting residue by reverse phase column chromatography [RediSep Gold C-18 50 g, 5 to 60% (0.1% NH$_4$OH in MeOH)/(0.1% NH$_4$OH in water)] then by normal phase silica gel column chromatography [(0 to 100% EtOAc/MeOH), Interchim (San Pedro, Calif.) 15 micron MeOH stable column] gave 4-(2-(2-(N-(1,2,4-thiadiazol-5-yl)sulfamoyl)-1,2,3,4-tetrahydro isoquinolin-5-yl)-5-(trifluoromethyl)phenyl)-1,1-dimethyl-1,2,3,6-tetrahydropyridin-1-ium hydroxide (0.026 g, 0.047 mmol). [M+H]$^+$=550.0 $^1$H NMR (400 MHz, Acetone-d$_6$) δ ppm: 7.71-7.79 (m, 3H), 7.48 (d, J=7.9 Hz, 1H), 7.14-7.22 (m, 1H), 7.06 (d, J=7.7 Hz, 2H), 5.75 (br. s., 1H), 4.15-4.45 (m, 4H), 3.67-3.84 (m, 2H), 3.55-3.65 (m, 1H), 3.23 (s, 3H), 3.18 (s, 3H), 3.09 (ddd, J=13.0, 9.6, 4.5 Hz, 1H), 2.64-2.75 (m, 1H), 2.51-2.61 (m, 2H), 2.32 (m, J=16.4, 4.4 Hz, 1H)

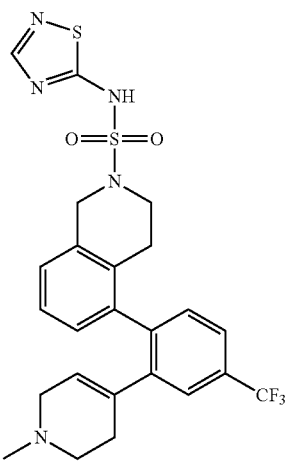 [SMILES: CN1CC=C(c2cc(C(F)(F)F)ccc2-c2cccc3c2CCN(S(=O)(=O)Nc2ncns2)C3)CC1]

Example 15

5-(2-(1-Methyl-1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide The title compound was prepared in a manner analogous to Example 5, Step 1, except that 1-methyl-4-(4,4,5,5-tetramethyl-1,3,2-dioxaborolan-2-yl)-1,2,3,6-tetrahydropyridine (Sigma-Aldrich, St. Louis, Mo.) was used in place of tert-butyl 4-(4,4,5,5-tetramethyl-1,3,2-dioxaborolan-2-yl)-5,6-dihydropyridine-1(2H)-carboxylate. [M+H]$^+$=536.0 $^1$H NMR (400 MHz, Acetone-d$_6$) δ ppm: 7.73-7.78 (m, 1H), 7.68 (s, 1H), 7.60 (s, 1H), 7.41 (d, J=7.8 Hz, 1H), 6.97-7.08 (m, 2H), 6.72 (d, J=7.3 Hz, 1H), 6.03 (m, 1H), 4.49 (d, J=17.4 Hz, 1H), 4.02-4.17 (m, 2H), 3.67-3.84 (m, 3H), 3.09-3.27 (m, 2H), 2.87-3.00 (m, 1H), 2.79-2.84 (s, 3H), 2.15-2.28 (m, 1H), 1.96-2.08 (m, 2H)

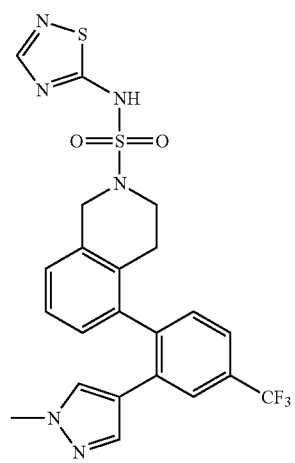 [SMILES: Cn1cc(-c2cc(C(F)(F)F)ccc2-c2cccc3c2CCN(S(=O)(=O)Nc2ncns2)C3)cn1]

Example 16

5-(2-(1-Methyl-1H-pyrazol-4-yl)-4-(trifluoromethyl)phenyl)-N-(1,2,4-thiadiazol-5-yl)-3,4-dihydroisoquinoline-2(1H)-sulfonamide The title compound was prepared in a manner analogous to Example 5, Step 1, except that 1-methyl-4-(4,4,5,5-tetramethyl-1,3,2-dioxaborolan-2-yl)-1H-pyrazole was used in place of tert-butyl 4-(4,4,5,5-tetramethyl-1,3,2-dioxaborolan-2-yl)-5,6-dihydropyridine-1(2H)-carboxylate. [M+H]⁺=521.0 ¹H NMR (400 MHz, Acetone-d₆) δ$_{ππμ}$: 8.25 (s, 1H), 7.92 (d, J=1.3 Hz, 1H), 7.68 (s, 1H), 7.63 (dd, J=8.0, 1.2 Hz, 1H), 7.41 (d, J=7.7 Hz, 1H), 7.26-7.32 (m, 1H), 7.17-7.23 (m, 1H), 7.09 (d, J=7.4 Hz, 1H), 6.88 (d, J=0.8 Hz, 1H), 4.37 (s, 2H), 3.83 (s, 3H), 3.40-3.49 (m, 1H), 3.20-3.30 (m, 1H), 2.40 (t, J=6.1 Hz, 2H)

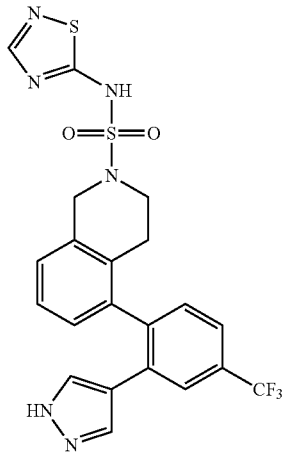 [SMILES: O=S(=O)(Nc1ncns1)N1CCc2c(cccc2-c2ccc(C(F)(F)F)cc2-c2cn[nH]c2)C1]

Example 17

5-(2-(1H-Pyrazol-4-yl)-4-(trifluoromethyl)phenyl)-N-(1,2,4-thiadiazol-5-yl)-3,4-dihydroisoquinoline-2(1H)-sulfonamide The title compound was prepared in a manner analogous to Example 5, except that 4-(4,4,5,5-tetramethyl-1,3,2-dioxaborolan-2-yl)-1H-pyrazole was used in place of tert-butyl 4-(4,4,5,5-tetramethyl-1,3,2-dioxaborolan-2-yl)-5,6-dihydropyridine-1(2H)-carboxylate. [M+H]⁺=507.0 ¹H NMR (400 MHz. Acetone-d₆) δ ppm: 8.23 (s, 1H), 7.98 (s, 1H), 7.65 (d, J=7.9 Hz, 1H), 7.39-7.44 (m, 3H), 7.27-7.33 (m, 1H), 7.19-7.23 (m, 1H), 7.11 (d, J=6.2 Hz, 1H), 4.34-4.39 (m, 2H), 3.37-3.47 (m, 1H), 3.24 (dt, J=13.1, 6.7 Hz, 1H), 2.39 (t, J=6.2 Hz, 2H)

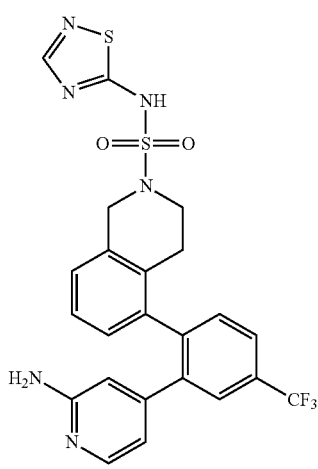 [SMILES: Nc1cc(-c2cc(C(F)(F)F)ccc2-c2cccc3c2CCN(S(=O)(=O)Nc2ncns2)C3)ccn1]

Example 18

5-(2-(2-Aminopyridin-4-yl)-4-(trifluoromethyl)phenyl)-N-(1,2,4-thiadiazol-5-yl)-3,4-dihydroisoquinoline-2(1H)-sulfonamide The title compound was prepared in a manner analogous to Example 5, Step 1, except that 4-(4,4,5,5-tetramethyl-1,3,2-dioxaborolan-2-yl)pyridin-2-amine was used in place of tert-butyl 4-(4,4,5,5-tetramethyl-1,3,2-dioxaborolan-2-yl)-5,6-dihydropyridine-1(2H)-carboxylate. [M+H]⁺=533.0 ¹H NMR (400 MHz, Acetone-d₆) δ ppm: 8.17 (s, 1H), 7.73-7.88 (m, 2H), 7.52-7.62 (m, 1H), 7.07-7.19 (m, 2H), 6.96-7.05 (m, 2H), 6.45 (d, J=0.7 Hz, 1H), 6.38 (dd, J=5.5, 1.5 Hz, 1H), 4.30 (d, J=9.1 Hz, 2H), 3.21-3.32 (m, 2H), 2.53-2.63 (m, 1H), 2.39-2.48 (m, 1H)

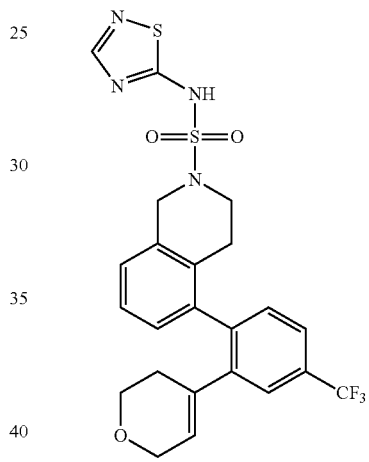

Example 19

5-(2-(3,6-Dihydro-2H-pyran-4-yl)-4-(trifluoromethyl)phenyl)-N-(1,2,4-thiadiazol-5-yl)-3,4-dihydroisoquinoline-2(1H)-sulfonamide The title compound was prepared in a manner analogous to Example 5, Step 1, except that 2-(3,6-dihydro-2H-pyran-4-yl)-4,4,5,5-tetramethyl-1,3,2-dioxaborolane (Pharmacore, High Point, N.C.) was used in place of tert-butyl 4-(4,4,5,5-tetramethyl-1,3,2-dioxaborolan-2-yl)-5,6-dihydropyridine-1(2H)-carboxylate. [M+H]⁺=523.0 ¹H NMR (400 MHz, Acetone-d₆) δ ppm: 8.26 (s, 1H), 7.68 (d, J=7.3 Hz, 1H), 7.64 (s, 1H), 7.40 (d, J=8.1 Hz, 1H), 7.22-7.28 (m, 1H), 7.15-7.21 (m, 1H), 7.08 (d, J=7.3 Hz, 1H), 5.79 (s, 1H), 4.38 (d, J=3.8 Hz, 2H), 4.12 (m, 2H), 3.61-3.69 (m, 1H), 3.49-3.58 (m, 1H), 3.37 (t, J=6.5 Hz, 2H), 2.51-2.82 (m, 4H)

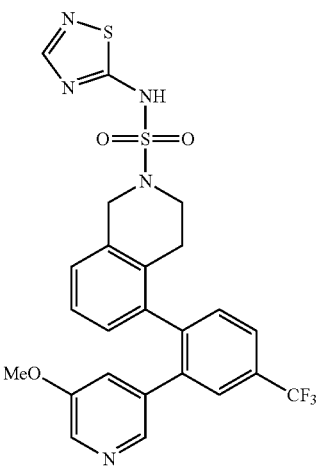 [SMILES: COc1cncc(-c2cc(C(F)(F)F)ccc2-c2cccc3c2CCN(S(=O)(=O)Nc2ncns2)C3)c1]

Example 20

5-(2-(5-Methoxypyridin-3-yl)-4-(trifluoromethyl)
phenyl)-N-(1,2,4-thiadiazol-5-yl)-3,4-dihydroiso-
quinoline-2(1H)-sulfonamide The title compound was prepared in a manner analogous to Example 5, Step 1, except that 3-methoxy-5-(4,4,5,5-tetramethyl-1,3,2-dioxaborolan-2-yl)pyridine was used in place of tert-butyl 4-(4,4,5,5-tetramethyl-1,3,2-dioxaborolan-2-yl)-5,6-dihydropyridine-1(2H)-carboxylate. [M+H]$^+$=548.0 $^1$H NMR (400 MHz, Acetone-d$_6$) δ ppm: 8.25-8.28 (m, 2H), 8.00 (s, 1H), 7.84-7.89 (m, 2H), 7.64 (d, J=7.9 Hz, 1H), 7.61 (dd, J=2.7, 1.9 Hz, 1H), 6.97-7.03 (m, 2H), 6.76 (d, J=6.3 Hz, 1H), 4.40-4.48 (m, 1H), 4.26-4.34 (m, 1H), 3.91 (s, 3H), 3.78-3.88 (m, 1H), 3.40 (m, 1H), 2.70-2.78 (m, 2H)

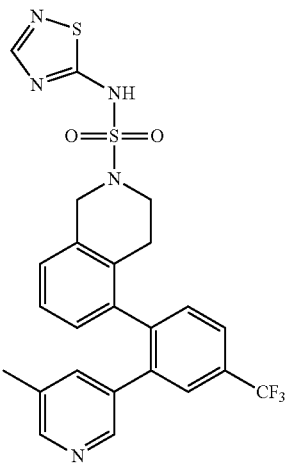 [SMILES: Cc1cncc(-c2cc(C(F)(F)F)ccc2-c2cccc3c2CCN(S(=O)(=O)Nc2ncns2)C3)c1]

Example 21

5-(2-(5-Methylpyridin-3-yl)-4-(trifluoromethyl)phe-
nyl)-N-(1,2,4-thiadiazol-5-yl)-3,4-dihydroisoquino-
line-2(1H)-sulfonamide The title compound was prepared in a manner analogous to Example 5, Step 1, except that (5-methylpyridin-3-yl)boronic acid was used in place of tert-butyl 4-(4,4,5,5-tetramethyl-1,3,2-dioxaborolan-2-yl)-5,6-dihydropyridine-1(2H)-carboxylate. [M+H]$^+$=532.0 $^1$H NMR (400 MHz, Acetone-d$_6$) δ ppm: 8.40 (s, 1H), 8.25 (s, 1H), 8.02 (d, J=2.2 Hz, 1H), 7.96 (d, J=10.0 Hz, 2H), 7.86 (d, J=8.0 Hz, 1H), 7.64 (d, J=8.1 Hz, 1H), 6.94-7.03 (m, 2H), 6.71 (d, J=6.5 Hz, 1H), 4.40-4.49 (d, J=17.7 Hz, 1H), 4.27-4.35 (d, J=17.7 Hz, 1H), 3.91 (m, 1H), 3.35-3.46 (m, 1H), 2.73-2.79 (m, 2H), 2.40 (s, 3H)

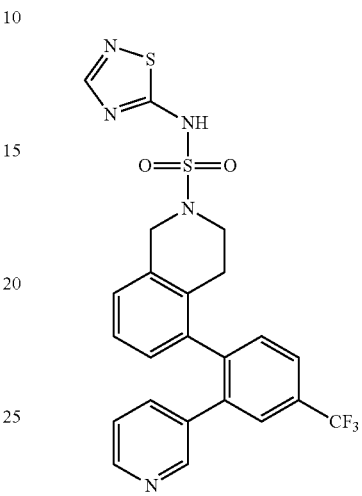

Example 22

5-(2-(Pyridin-3-yl)-4-(trifluoromethyl)phenyl)-N-(1,
2,4-thiadiazol-5-yl)-3,4-dihydroisoquinoline-2(1H)-
sulfonamide The title compound was prepared in a manner analogous to Example 5, Step 1, except that pyridin-3-ylboronic acid was used in place of tert-butyl 4-(4,4,5,5-tetramethyl-1,3,2-dioxaborolan-2-yl)-5,6-dihydropyridine-1(2H)-carboxylate. [M+H]$^+$=518.0 $^1$H NMR (400 MHz, Acetone-d$_6$) δ ppm: 8.56 (d, J=5.0 Hz, 1H), 8.28 (s, 1H), 8.22 (d, J=2.4 Hz, 1H), 8.08 (dt, J=8.0, 2.0 Hz, 1H), 7.97 (s, 1H), 7.84-7.90 (m, 1H), 7.65 (d, J=7.9 Hz, 1H), 7.56 (m, 1H), 6.95-7.04 (m, 2H), 6.70-6.76 (m, 1H), 4.45 (d, J=17.4 Hz, 1H), 4.31 (d, J=17.0 Hz, 1H), 3.80-3.93 (m, 1H), 3.37-3.45 (m, 1H), 2.71-2.79 (m, 2H)

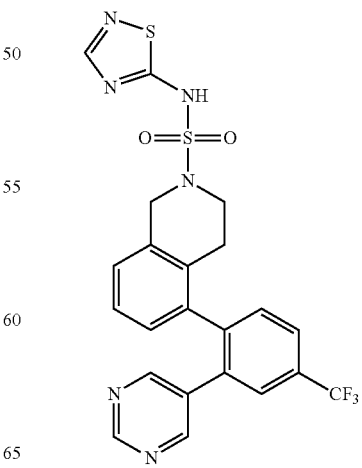

Example 23

5-(2-(Pyrimidin-5-yl)-4-(trifluoromethyl)phenyl)-N-(1,2,4-thiadiazol-5-yl)-3,4-dihydroisoquinoline-2(1H)-sulfonamide The title compound was prepared in a manner analogous to Example 5, Step 1, except that pyrimidin-5-ylboronic acid was used in place of tert-butyl 4-(4,4,5,5-tetramethyl-1,3,2-dioxaborolan-2-yl)-5,6-dihydropyridine-1(2H)-carboxylate. [M+H]$^+$=519.0 $^1$H NMR (400 MHz, Acetone-d$_6$) δ ppm: 9.10 (s, 1H), 8.68 (s, 2H), 8.28 (s, 1H), 8.06 (s, 1H), 7.90-7.96 (m, 1H), 7.68 (d, J=8.0 Hz, 1H), 7.06-7.10 (m, 2H), 6.88 (t, J=4.4 Hz, 1H), 4.25-4.46 (m, 2H), 3.59-3.69 (m, 1H), 3.32-3.46 (m, 1H), 2.69-2.78 (m, 1H), 2.56-2.65 (m, 1H)

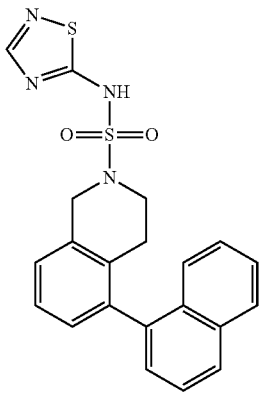 [SMILES: O=S(=O)(Nc1ncns1)N1CCc2c(cccc2-c2cccc3ccccc23)C1]

Example 24

5-(Naphthalen-1-yl)-N-(1,2,4-thiadiazol-5-yl)-3,4-dihydroisoquinoline-2(1H)-sulfonamide The title compound was prepared in a manner analogous to Example 1, except that 4,4,5,5-tetramethyl-2-(naphthalen-1-yl)-1,3,2-dioxaborolane was used in place of (2-(1-methyl-1H-pyrazol-5-yl)-4-(trifluoromethyl)phenyl)boronic acid. [M+H]$^+$=423.3 $^1$H NMR (400 MHz, DMSO-d$_6$) δ ppm: 8.40 (s, 1H), 7.96 (d, J=8.2 Hz, 1H), 7.99 (d, J=8.1 Hz, 1H), 7.50-7.60 (m, 2H), 7.44 (t, J=7.1 Hz, 1H), 7.26-7.36 (m, 4H), 7.11 (d, J=6.1 Hz, 1H), 4.42 (d, J=15.7 Hz, 1H), 4.33 (d, J=15.6 Hz, 1H), 3.12-3.20 (m, 2H), 2.44 (dt, J=17.0, 5.7 Hz, 1H), 2.26 (dt, J=16.8, 6.3 Hz, 1H)

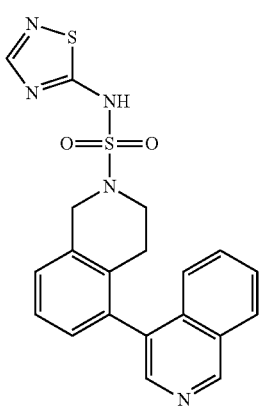 [SMILES: O=S(=O)(Nc1ncns1)N1CCc2c(cccc2-c2cncc3ccccc23)C1]

Example 25

N-(1,2,4-Thiadiazol-5-yl)-3',4'-dihydro-[4,5'-biisoquinoline]-2'(1'H)-sulfonamide The title compound was prepared in a manner analogous to Example 1, except that 4-(4,4,5,5-tetramethyl-1,3,2-dioxaborolan-2-yl)isoquinoline was used in place of (2-(1-methyl-1H-pyrazol-5-yl)-4-(trifluoromethyl)phenyl)boronic acid. [M+H]$^+$=424.3 $^1$H NMR (400 MHz, DMSO-d$_6$) δ ppm: 9.53 (s, 1H), 8.43 (d, J=9.1 Hz, 2H), 8.34 (d, J=8.2 Hz, 1H), 7.80-7.88 (m, 2H), 7.35-7.45 (m, 3H), 7.18-7.21 (m, 1H), 4.40-4.49 (m, 1H), 4.33-4.39 (m, 1H), 3.17-3.30 (m, 2H), 2.48-2.55 (m, 1H), 2.25-2.32 (m, 1H)

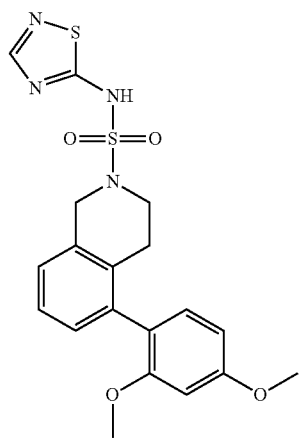 [SMILES: COc1ccc(-c2cccc3c2CCN(S(=O)(=O)Nc2ncns2)C3)c(OC)c1]

Example 26

5-(2,4-Dimethoxyphenyl)-N-(1,2,4-thiadiazol-5-yl)-3,4-dihydroisoquinoline-2(1H)-sulfonamide The title compound was prepared in a manner analogous to Example 1, except that (2,4-dimethoxyphenyl)boronic acid was used in place of (2-(1-methyl-1H-pyrazol-5-yl)-4-(trifluoromethyl)phenyl)boronic acid. [M+H]$^+$=433.4 $^1$H NMR (400 MHz, DMSO-d$_6$) δ ppm: 8.39 (s, 1H), 7.18 (t, J=7.5 Hz, 1H), 7.11 (d, J=7.3 Hz, 1H), 6.94-7.00 (m, 2H), 6.63 (d, J=2.3 Hz, 1H), 6.57 (dd, J=8.3, 2.4 Hz, 1H), 4.33 (d, J=14.8 Hz, 1H), 4.21 (d, J=15.5 Hz, 1H), 3.80 (s, 3H), 3.69 (s, 3H), 3.01-3.20 (m, 2H), 2.58-2.64 (m, 1H), 2.36-2.49 (m, 1H)

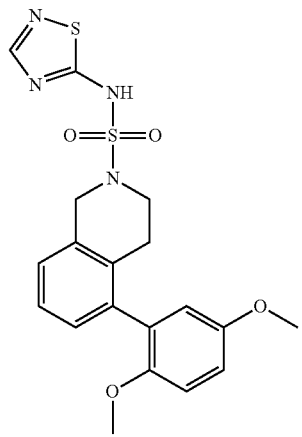 [SMILES: COc1ccc(OC)c(-c2cccc3c2CCN(S(=O)(=O)Nc2ncns2)C3)c1]

Example 27

5-(2,5-Dimethoxyphenyl)-N-(1,2,4-thiadiazol-5-yl)-3,4-dihydroisoquinoline-2(1H)-sulfonamide The title compound was prepared in a manner analogous to Example 1, except that (2,5-dimethoxyphenyl)boronic acid was used in place of (2-(1-methyl-1H-pyrazol-5-yl)-4-(trifluoromethyl)phenyl)boronic acid. [M+H]$^+$=433.3 $^1$H NMR (400 MHz, DMSO-d$_6$) δ ppm: 8.39 (s, 1H), 7.13-7.22 (m, 2H), 7.00 (d, J=9.0 Hz, 2H), 6.91 (dd, J=8.9, 3.1 Hz, 1H), 6.64 (d, J=3.1 Hz, 1H), 4.34 (d, J=15.4 Hz, 1H), 4.22 (d, J=15.6 Hz, 1H), 3.71 (s, 3H), 3.63 (s, 3H), 3.06-3.20 (m, 2H), 2.58-2.66 (m, 1H), 2.43-2.49 (m, 1H)

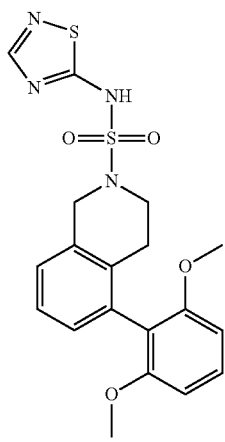 [SMILES: COc1cccc(OC)c1-c1cccc2c1CCN(S(=O)(=O)Nc1ncns1)C2]

Example 28

5-(2,6-Dimethoxyphenyl)-N-(1,2,4-thiadiazol-5-yl)-3,4-dihydroisoquinoline-2(1H)-sulfonamide The title compound was prepared in a manner analogous to Example 1, except that (2,6-dimethoxyphenyl)boronic acid was used in place of (2-(1-methyl-1H-pyrazol-5-yl)-4-(trifluoromethyl)phenyl)boronic acid. [M+H]$^+$=433.3 $^1$H NMR (400 MHz, DMSO-d$_6$) δ ppm: 8.40 (s, 1H), 7.32 (t, J=8.4 Hz, 1H), 7.16 (t, J=7.5 Hz, 1H), 7.09 (d, J=7.2 Hz, 1H), 6.90 (d, J=6.7 Hz, 1H), 6.73 (d, J=8.4 Hz, 2H), 4.26 (s, 2H), 3.63 (s, 6H), 3.20 (t, J=5.9 Hz, 2H), 2.41 (t, J=5.9 Hz, 2H)

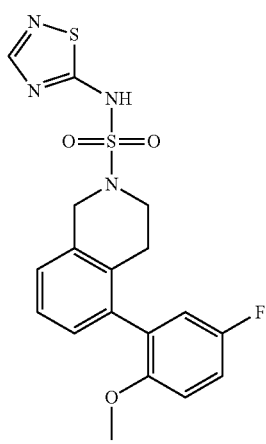 [SMILES: COc1ccc(F)cc1-c1cccc2c1CCN(S(=O)(=O)Nc1ncns1)C2]

Example 29

5-(5-Fluoro-2-methoxyphenyl)-N-(1,2,4-thiadiazol-5-yl)-3,4-dihydroisoquinoline-2(1H)-sulfonamide The title compound was prepared in a manner analogous to Example 1, except that (5-fluoro-2-methoxyphenyl)boronic acid was used in place of (2-(1-methyl-1H-pyrazol-5-yl)-4-(trifluoromethyl)phenyl)boronic acid. [M+H]$^+$=421.3 $^1$H NMR (400 MHz, DMSO-d$_6$) δ ppm: 8.39 (s, 1H), 7.13-7.23 (m, 3H), 7.08 (dd, J=9.0, 4.6 Hz, 1H), 6.91-7.04 (m, 2H), 4.34 (d, J=14.8 Hz, 1H), 4.23 (d, J=14.9 Hz, 1H), 3.68 (s, 3H), 3.14-3.18 (m, 2H), 2.56-2.65 (m, 1H), 2.44-2.49 (m, 1H)

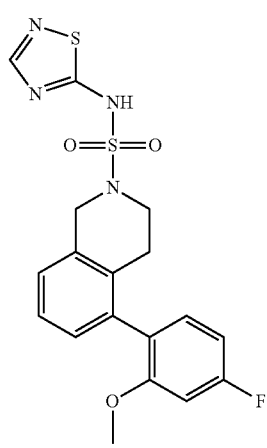 [SMILES: COc1cc(F)ccc1-c1cccc2c1CCN(S(=O)(=O)Nc1ncns1)C2]

Example 30

5-(4-Fluoro-2-methoxyphenyl)-N-(1,2,4-thiadiazol-5-yl)-3,4-dihydroisoquinoline-2(1H)-sulfonamide The title compound was prepared in a manner analogous to Example 1, except that (4-fluoro-2-methoxyphenyl)boronic acid was used in place of (2-(1-methyl-1H-pyrazol-5-yl)-4-(trifluoromethyl)phenyl)boronic acid. [M+H]$^+$=421.3 $^1$H NMR (400 MHz, DMSO-d$_6$) δ ppm: 8.39 (s, 1H), 7.07-7.25 (m, 3H), 6.96-7.02 (m, 2H), 6.82 (td, J=8.3, 2.4 Hz, 1H), 4.34 (d, J=15.4 Hz, 1H), 4.22 (d, J=15.4 Hz, 1H), 3.72 (s, 3H), 3.09-3.20 (m, 2H), 2.51-2.70 (m, 1H), 2.33-2.49 (m, 1H)

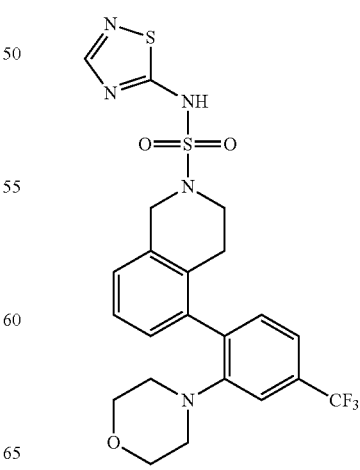

Example 31

5-(2-Morpholino-4-(trifluoromethyl)phenyl)-N-(1,2,4-thiadiazol-5-yl)-3,4-dihydroisoquinoline-2(1H)-sulfonamide A solution of Cl$_2$Pd(AmPhos) (Sigma-Aldrich, St. Louis, Mo., 0.023 g, 0.033 mmol), 4-(2-bromo-5-(trifluoromethyl)phenyl)morpholine (Intermediate G, 0.154 g, 0.497 mmol), 5-(4,4,5,5-tetramethyl-1,3,2-dioxaborolan-2-yl)-N-(1,2,4-thiadiazol-5-yl)-3,4-dihydroisoquinoline-2(1H)-sulfonamide (Intermediate F, 0.140 g, 0.331 mmol), and potassium phosphate (0.281 g, 1.326 mmol) in 2.5 mL dioxane and 1 mL water was heated to 100° C. 2 hours. The reaction mixture was cooled to rt, diluted with EtOAc and washed with 1 N citric acid solution. The organic layers were dried over MgSO$_4$ and concentrated. Purification of the resulting residue by reverse phase column chromatography [RediSep Gold C-18 50 g, 5 to 100% (0.1% NH$_4$OH in MeOH)/(0.1% NH$_4$OH in water)] gave 5-(2-morpholino-4-(trifluoromethyl)phenyl)-N-(1,2,4-thiadiazol-5-yl)-3,4-dihydroisoquinoline-2(1H)-sulfonamide (0.016 g, 0.030 mmol). [M+H]$^+$=525.8 $^1$H NMR (400 MHz, Acetone-d$_6$) δ ppm: 8.23 (s, 1H), 7.38-7.44 (m, 1H), 7.26-7.36 (m, 3H), 7.14-7.22 (m, 2H), 4.35-4.40 (m, 2H), 3.39-3.49 (m, 3H), 3.28-3.38 (m, 2H), 2.86-2.96 (m, 2H), 2.73-2.81 (m, 2H), 2.47-2.60 (m, 1H)

DCM was cooled to −78° C. and was treated with sulfuryl chloride (0.213 ml, 2.62 mmol). The cooling bath was removed, and the reaction mixture was allowed to stir for 20 minutes before 8-(2-(1H-imidazol-1-yl)-4-(trifluoromethyl)phenyl)-1,2,3,4-tetrahydroisoquinoline (Intermediate R, 0.450 g, 1.311 mmol) was added as a solution in 5 mL DCM. The reaction mixture was allowed to stir for one hour before being poured into 1N citric acid and extracted with EtOAc. The organic layers were concentrated and purified by reverse phase column chromatography [RediSep Gold C-18 150 g, 10 to 100% (0.1% NH4OH in MeOH)/(0.1% NH4OH in water)] gave 5-(2-(1H-imidazol-1-yl)-4-(trifluoromethyl)phenyl)-N-(1,2,4-thiadiazol-5-yl)-3,4-dihydroisoquinoline-2(1H)-sulfonamide. [M+H]$^+$=507.0 $^1$H NMR (400 MHz, Acetone-d$_6$) δ ppm: 8.16 (s, 1H), 7.99 (s, 1H), 7.92 (d, J=8.0 Hz, 1H), 7.71 (d, J=8.0 Hz, 1H), 7.55 (s, 1H), 7.48 (t, J=1.3 Hz, 1H), 7.03-7.15 (m, 3H), 6.92-6.97 (m, 1H), 4.25-4.45 (m, 2H), 3.75-3.86 (m, 1H), 3.28-3.35 (m, 1H), 2.46-2.63 (m, 2H)

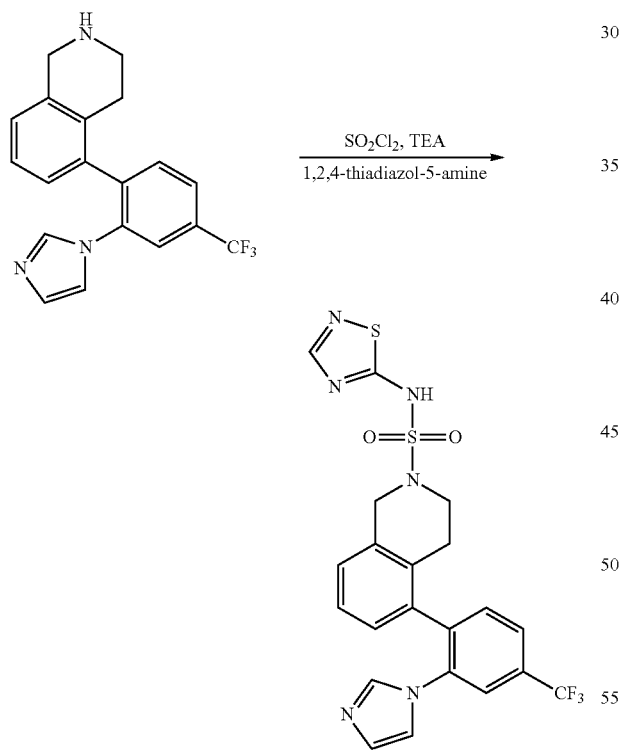
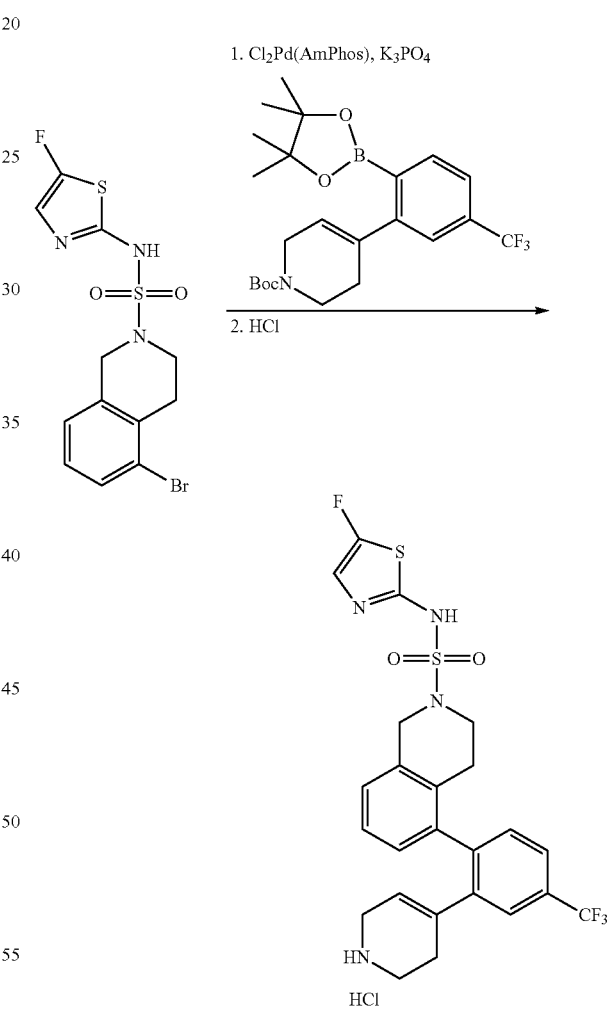

Example 32

5-(2-(1H-Imidazol-1-yl)-4-(trifluoromethyl)phenyl)-N-(1,2,4-thiadiazol-5-yl)-3,4-dihydroisoquinoline-2(1H)-sulfonamide A solution of 1,2,4-thiadiazol-5-amine (0.265 g, 2.62 mmol) and triethylamine (1.096 ml, 7.86 mmol) in 5 mL

Example 33

N-(5-Fluorothiazol-2-yl)-5-(2-(1,2,3,6-tetrahydropyridin-4-yl)-4-(trifluoromethyl)phenyl)-3,4-dihydroisoquinoline-2(1H)-sulfonamide hydrochloride A solution of Cl$_2$Pd(AmPhos) (Sigma-Aldrich, St. Louis, Mo., 0.027 g, 0.038 mmol), tert-butyl 4-(2-(4,4,5,5-tetramethyl-1,3,2-dioxaborolan-2-yl)-5-(trifluoromethyl)phenyl)-5,6-dihydropyridine-1(2H)-carboxylate (Intermediate K, 0.260 g, 0.574 mmol), 5-bromo-N-(5-fluorothiazol-2-yl)-3,4-dihydroisoquinoline-2(1H)-sulfonamide (Intermediate I, 0.150 g, 0.382 mmol), and potassium phosphate (0.325 g, 1.530 mmol) in 2.5 mL dioxane, 1 mL water was heated to 100° C. 2 hours. The reaction mixture was diluted with EtOAc and washed with 1 N citric acid solution. The organics were dried over MgSO₄ and concentrated. Purification of the resulting residue by silica gel column chromatography (0 to 100% EtOAc/heptane) gave tert-butyl 4-(2-(2-(N-(5-fluorothiazol-2-yl)sulfamoyl)-1,2,3,4-tetrahydroisoquinolin-5-yl)-5-(trifluoromethyl)phenyl)-5,6-dihydropyridine-1(2H)-carboxylate (0.063 g, 0.099 mmol). This material was taken up in 1 mL THF, was treated with HCl 4N in dioxane (1.912 ml, 7.65 mmol) and was allowed to stir at room temperature overnight. The reaction mixture was concentrated yielding N-(5-fluorothiazol-2-yl)-5-(2-(1,2,3,6-tetrahydropyridin-4-yl)-4-(trifluoromethyl)phenyl)-3,4-dihydroisoquinoline-2(1H)-sulfonamide hydrochloride (0.063 g, 0.117 mmol). [M+H]⁺=538.8 ¹H NMR (400 MHz, DMSO-d₆) δ ppm: 8.82 (br. s., 2H), 7.73 (d, J=7.9 Hz, 1H), 7.60 (s, 1H), 7.43 (d, J=8.0 Hz, 1H), 7.30 (s, 1H), 7.25 (d, J=4.7 Hz, 2H), 7.02 (t, J=4.5 Hz, 1H), 5.71 (br. s., 1H), 4.29 (s, 2H), 3.62-3.68 (m, 1H), 3.53-3.59 (m, 2H), 3.37-3.44 (m, 1H), 3.18-3.28 (m, 2H), 2.85-3.07 (m, 2H), 2.06-2.20 (m, 1H), 1.92-2.02 (m, 1H)

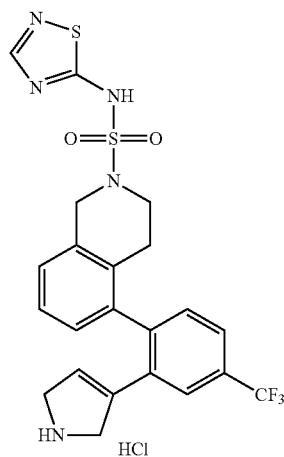 [SMILES: O=S(=O)(Nc1ncns1)N1CCc2c(cccc2-c2ccc(C(F)(F)F)cc2C2=CCNC2)C1 ; Cl]

Example 34

5-(2-(2,5-Dihydro-1H-pyrrol-3-yl)-4-(trifluoromethyl)phenyl)-N-(1,2,4-thiadiazol-5-yl)-3,4-dihydroisoquinoline-2(1H)-sulfonamide hydrochloride The title compound was prepared in a manner analogous to Example 1, except that tert-butyl 3-(4,4,5,5-tetramethyl-1,3,2-dioxaborolan-2-yl)-2,5-dihydro-1H-pyrrole-1-carboxylate was used in place of (2-(1-methyl-1H-pyrazol-5-yl)-4-(trifluoromethyl)phenyl)boronic acid and the resulting product, (tert-butyl 3-(2-(2-(N-(1,2,4-thiadiazol-5-yl)sulfamoyl)-1,2,3,4-tetrahydroisoquinolin-5-yl)-5-(trifluoromethyl)phenyl)-2,5-dihydro-1H-pyrrole-1-carboxylate), was converted to the final product by treatment with 50 equivalents of HCl in dioxane. The reaction mixture was concentrated under a vacuum to provide 5-(2-(2,5-dihydro-1H-pyrrol-3-yl)-4-(trifluoromethyl)phenyl)-N-(1,2,4-thiadiazol-5-yl)-3,4-dihydroisoquinoline-2(1H)-sulfonamide hydrochloride. [M+H]⁺=508.8 ¹H NMR (400 MHz, DMSO-d₆) δ ppm: 9.36 (br. s., 2H), 8.38 (s, 1H), 7.73-7.83 (m, 2H), 7.43 (d, J=7.8 Hz, 1H), 7.23-7.33 (m, 2H), 6.97-7.16 (m, 2H), 5.77 (br. s., 1H), 4.20-4.38 (m, 2H), 3.92 (br. s., 2H), 3.74 (br. s., 2H), 3.64 (t, J=6.7 Hz, 1H), 3.41 (t, J=6.3 Hz, 1H), 3.26-3.36 (m, 1H), 3.12-3.24 (m, 1H)

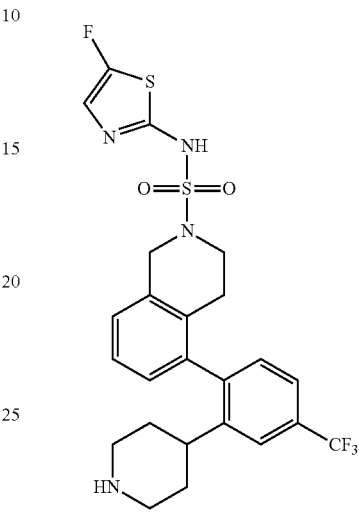

Example 35

N-(5-Fluorothiazol-2-yl)-5-(2-(piperidin-4-yl)-4-(trifluoromethyl)phenyl)-3,4-dihydroisoquinoline-2(1H)-sulfonamide hydrochloride The title compound was prepared in a method analogous to Example 33 with the exception that tert-butyl 4-(2-(4,4,5,5-tetramethyl-1,3,2-dioxaborolan-2-yl)-5-(trifluoromethyl)phenyl)piperidine-1-carboxylate (Intermediate S) was used in place of tert-butyl 4-(2-(4,4,5,5-tetramethyl-1,3,2-dioxaborolan-2-yl)-5-(trifluoromethyl)phenyl)-5,6-dihydropyridine-1(2H)-carboxylate. [M+H]⁺=540.8 ¹H NMR (400 MHz, DMSO-d₆) δ ppm: 8.06-8.28 (m, 1H), 7.59-7.68 (m, 2H), 7.32 (d, J=7.9 Hz, 1H), 7.20 (dt, J=14.7, 7.3 Hz, 2H), 6.95 (d, J=6.0 Hz, 1H), 6.53 (d, J=1.6 Hz, 1H), 4.11-4.29 (m, 2H), 3.14-3.27 (m, 4H), 2.97-3.13 (m, 1H), 2.81-2.93 (m, 1H), 2.65-2.78 (m, 2H), 2.25-2.39 (m, 2H), 1.89-2.04 (m, 1H), 1.68-1.78 (m, 2H)

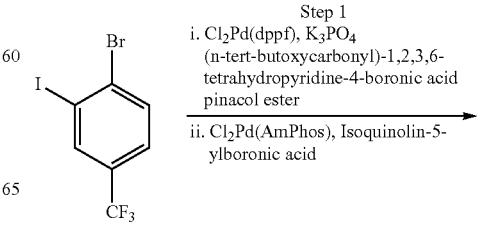

Step 1
i. Cl₂Pd(dppf), K₃PO₄ (n-tert-butoxycarbonyl)-1,2,3,6-tetrahydropyridine-4-boronic acid pinacol ester
ii. Cl₂Pd(AmPhos), Isoquinolin-5-ylboronic acid

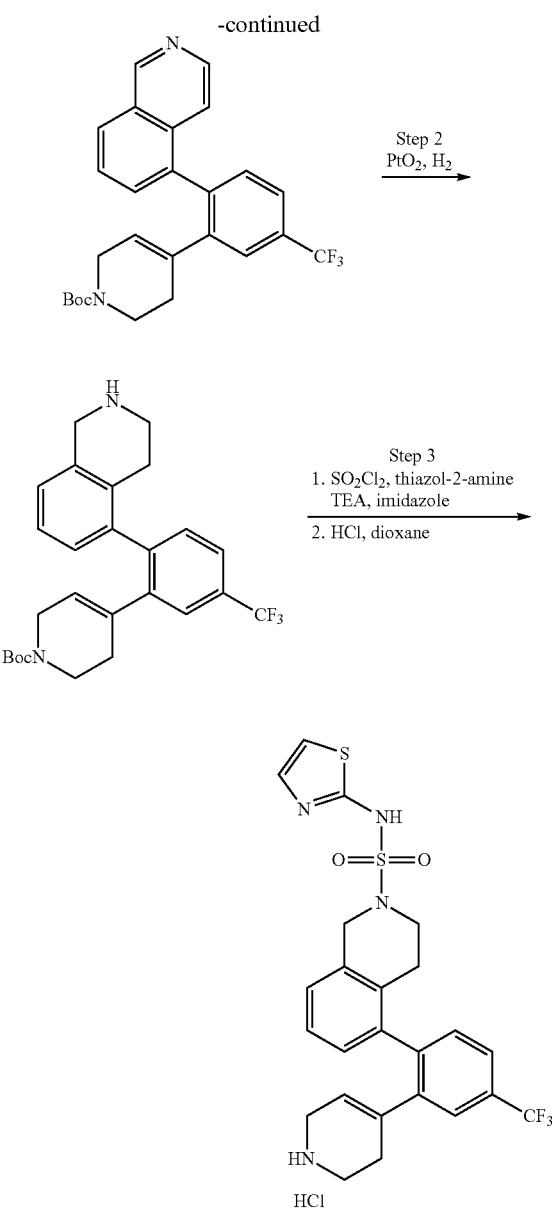

Example 36

5-(2-(1,2,3,6-Tetrahydropyridin-4-yl)-4-(trifluoromethyl)phenyl)-N-(thiazol-2-yl)-3,4-dihydroisoquinoline-2(1H)-sulfonamide hydrochloride Step 1: tert-Butyl 4-(2-(isoquinolin-5-yl)-5-(trifluoromethyl)phenyl)-5,6-dihydropyridine-1(2H)-carboxylate A solution of Cl₂Pd(dppf)-CH₂Cl₂ adduct (Strem Chemicals Inc., Newburyport, Mass., 1.157 g, 1.416 mmol), (n-tert-butoxycarbonyl)-1,2,3,6-tetrahydropyridine-4-boronic acid pinacol ester (8.76 ml, 28.3 mmol), 1-bromo-2-iodo-4-(trifluoromethyl)benzene (9.94 g, 28.3 mmol), and potassium phosphate (36.1 g, 170 mmol) in 100 mL dioxane, 40 mL water was heated to 100° C. 3 hours. LC/MS showed complete consumption of starting material. Isoquinolin-5-ylboronic acid (4.90 g, 28.3 mmol) and Cl₂Pd(AmPhos) (Sigma-Aldrich, St. Louis, Mo., 1.003 g, 1.416 mmol) were added, and the reaction mixture was again heated to 100° C. for an additional hour. The reaction mixture was allowed to cool to room temperature and was diluted with diethyl ether. The organics were washed with water, then brine, dried over MgSO₄ and concentrated. Purification of the resulting residue by silica gel column chromatography (0 to 100% EtOAc/heptane) gave tert-butyl 4-(2-(isoquinolin-5-yl)-5-(trifluoromethyl)phenyl)-5,6-dihydropyridine-1(2H)-carboxylate (9.80 g, 21.56 mmol).

Step 2: tert-Butyl 4-(2-(1,2,3,4-tetrahydroisoquinolin-5-yl)-5-(trifluoromethyl)phenyl)-5,6-dihydropyridine-1(2H)-carboxylate A solution of tert-butyl 4-(2-(isoquinolin-5-yl)-5-(trifluoromethyl)phenyl)-5,6-dihydropyridine-1(2H)-carboxylate (9.80 g, 21.56 mmol) in 50 mL MeOH was treated with acetic acid (1.234 ml, 21.56 mmol) and platinum(IV) oxide (Sigma-Aldrich, St. Louis, Mo., 0.979 g, 4.31 mmol) and was placed under 45 psi (4559.6 kpa) H₂ overnight. The reaction mixture was filtered through a plug of diatomaceous earth and concentrated. The resulting residue was taken up in DCM, was washed with saturated NaHCO₃ solution, the organics dried over MgSO₄ and concentrated yielding tert-butyl 4-(2-(1,2,3,4-tetrahydroisoquinolin-5-yl)-5-(trifluoromethyl)phenyl)-5,6-dihydropyridine-1(2H)-carboxylate (8.21 g, 17.91 mmol).

Step 3: 5-(2-(1,2,3,6-Tetrahydropyridin-4-yl)-4-(trifluoromethyl)phenyl)-N-(thiazol-2-yl)-3,4-dihydroisoquinoline-2(1H)-sulfonamide hydrochloride A solution of 1H-imidazole (0.238 g, 3.49 mmol) and thiazol-2-amine (TCI America, Portland, Oreg., 0.087 g, 0.872 mmol) in 6 mL DCM was cooled to −10° C. and was treated with sulfuryl chloride (0.071 ml, 0.872 mmol). After stirring for 15 minutes, the cooling bath was removed, and the reaction mixture was allowed to stir for an additional 15 minutes. The reaction mixture was treated with tert-butyl 4-(2-(1,2,3,4-tetrahydroisoquinolin-5-yl)-5-(trifluoromethyl)phenyl)-5,6-dihydropyridine-1(2H)-carboxylate (0.200 g, 0.436 mmol) and triethylamine (0.608 ml, 4.36 mmol) and was heated to 80° C. for 20 minutes. The reaction mixture was diluted with EtOAc, washed with 1N citric acid solution and the organics concentrated. Purification of the resulting residue by reverse phase column chromatography [RediSep Gold C-18 100 g, 10 to 100% (0.1% NH₄OH in MeOH)/(0.1% NH₄OH in water)] gave tert-butyl 4-(2-(2-(N-(thiazol-2-yl)sulfamoyl)-1,2,3,4-tetrahydroisoquinolin-5-yl)-5-(trifluoromethyl)phenyl)-5,6-dihydropyridine-1(2H)-carboxylate (0.133 g, 0.214 mmol). This material was taken up in 1 mL THF, was treated with HCl 4N in dioxane (1.090 ml, 4.36 mmol) and was heated to 80° C. for one hour. Concentration and purification of the resulting residue by reverse phase column chromatography [RediSep Gold C-18 50 g 10 to 100% (0.1% NH₄OH in MeOH)/(0.1% NH₄OH in water)] gave 5-(2-(1,2,3,6-tetrahydropyridin-4-yl)-4-(trifluoromethyl)phenyl)-N-(thiazol-2-yl)-3,4-dihydroisoquinoline-2(1H)-sulfonamide (0.053 g, 0.102 mmol). [M+H]⁺=520.8 ¹H NMR (400 MHz, DMSO-d₆) δ ppm: 7.75 (d, J=8.1 Hz, 1H), 7.49 (d, J=7.9 Hz, 1H), 7.43 (s, 1H), 7.12 (t, J=7.9 Hz, 1H), 6.90-7.04 (m, 3H), 6.54 (d, J=4.1 Hz, 1H), 5.75 (br. s., 1H), 4.11-4.40 (m, 2H), 3.52 (br. s., 2H), 3.33-3.48 (m, 1H), 3.00-3.13 (m, 2H), 2.73-2.86 (m, 1H), 2.60-2.73 (m, 1H), 2.08-2.23 (m, 1H), 1.77-2.03 (m, 2H)

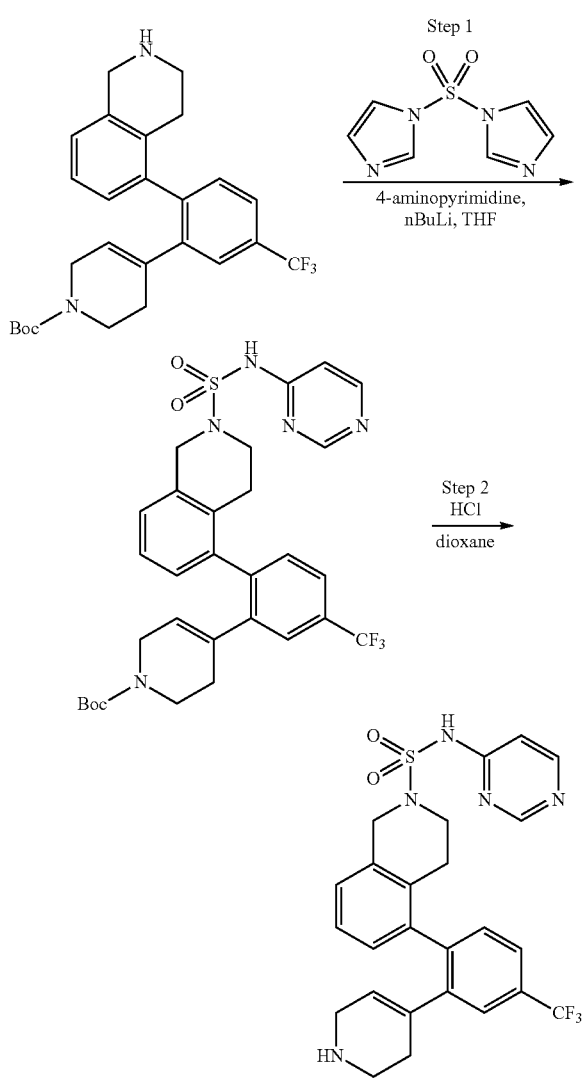

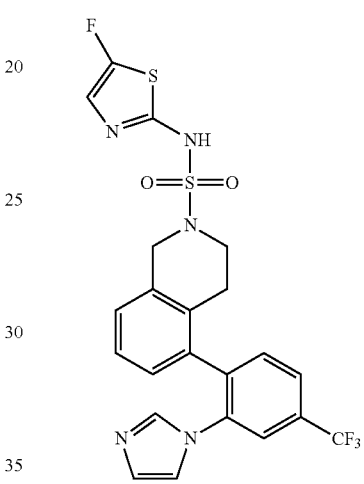

Example 37

N-(Pyrimidin-4-yl)-5-(2-(1,2,3,6-tetrahydropyridin-4-yl)-4-(trifluoromethyl)phenyl)-3,4-dihydroisoquinoline-2(1H)-sulfonamide Step 1: A solution of pyrimidin-4-amine (0.083 g, 0.872 mmol) in 3 mL THF was cooled to −78° C. and was treated with n-butyllithium 2.5N in hexane (0.349 ml, 0.872 mmol). The cooling bath was removed, and the reaction mixture was allowed to stir for 10 minutes. 1,1'-sulfonylbis(1H-imidazole) (Intermediate Z; 0.173 g, 0.872 mmol) was added, and the reaction mixture was heated to reflux for one hour. Intermediate L (0.200 g, 0.436 mmol) was added, and the reaction mixture was heated to 100° C. overnight. The reaction mixture was then diluted with EtOAc, washed with 1N citric acid, the organics dried over MgSO4 and concentrated. Purification of the resulting residue by reverse phase column chromatography [RediSep Gold C-18 100 g 10 to 100% (0.1% NH4OH in MeOH)/(0.1% NH4OH in water)] yielded tert-butyl 4-(2-(2-(N-(pyrimidin-4-yl)sulfamoyl)-1,2,3,4-tetrahydroisoquinolin-5-yl)-5-(trifluoromethyl)phenyl)-5,6-dihydropyridine-1(2H)-carboxylate (0.108 g, 0.175 mmol).

Step 2: The material from Step 1 was taken up in 2 mL THF, treated with HCl 4N in dioxane (1.090 ml, 4.36 mmol) and was heated to 80° C. overnight. The reaction mixture was then concentrated. Purification of the resulting residue by reverse phase column chromatography [RediSep Gold C-18 100 g 10 to 100% (0.1% NH4OH in MeOH)/(0.1% NH4OH in water)] gave N-(pyrimidin-4-yl)-5-(2-(1,2,3,6-tetrahydropyridin-4-yl)-4-(trifluoromethyl)phenyl)-3,4-dihydroisoquinoline-2(1H)-sulfonamide (0.085 g, 0.165 mmol). [M+H]⁺=515.8 ¹H NMR (400 MHz, Acetone-d₆) δ ppm: 8.58 (s, 1H), 8.34 (d, J=5.8 Hz, 1H), 7.77 (d, J=8.1 Hz, 1H), 7.61 (d, J=7.8 Hz, 1H), 7.49 (s, 1H), 7.21-7.26 (m, 2H), 7.10-7.20 (m, 2H), 5.87 (br. s., 1H), 4.46-4.78 (m, 2H), 3.80 (br. s., 2H), 3.69-3.77 (m, 1H), 3.47 (dd, J=10.1, 4.6 Hz, 1H), 3.13-3.22 (m, 2H), 3.03-3.12 (m, 2H), 2.74-2.84 (m, 1H), 2.34-2.43 (m, 1H).

Example 38

5-(2-(1H-Imidazol-1-yl)-4-(trifluoromethyl)phenyl)-N-(5-fluorothiazol-2-yl)-3,4-dihydroisoquinoline-2(1H)-sulfonamide The title compound was prepared in a procedure analogous to Intermediate I, wherein 8-(2-(1H-imidazol-1-yl)-4-(trifluoromethyl)phenyl)-1,2,3,4-tetrahydroisoquinoline (Intermediate R) was substituted for 5-bromo-1,2,3,4-tetrahydroisoquinoline hydrochloride [M+H]⁺=524.0 ¹H NMR (400 MHZ, Acetone-d₆) δ ppm: 7.97 (s, 1H), 7.91 (dd, J=7.9, 1.0 Hz, 1H), 7.70 (d, J=8.0 Hz, 1H), 7.48 (d, J=1.0 Hz, 1H), 7.44 (t, J=1.3 Hz, 1H), 7.10-7.19 (m, 2H), 6.97-7.02 (m, 3H), 4.28-4.41 (m, 2H), 3.68-3.77 (m, 1H), 3.21-3.32 (m, 1H), 2.44-2.54 (m, 2H)

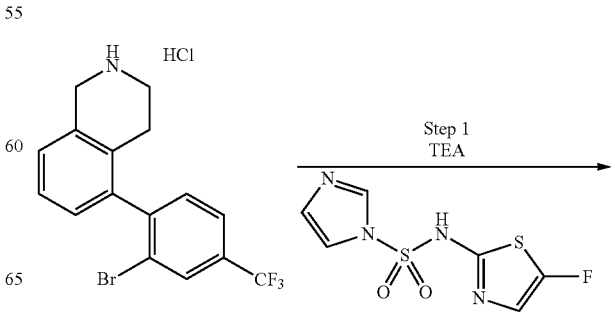

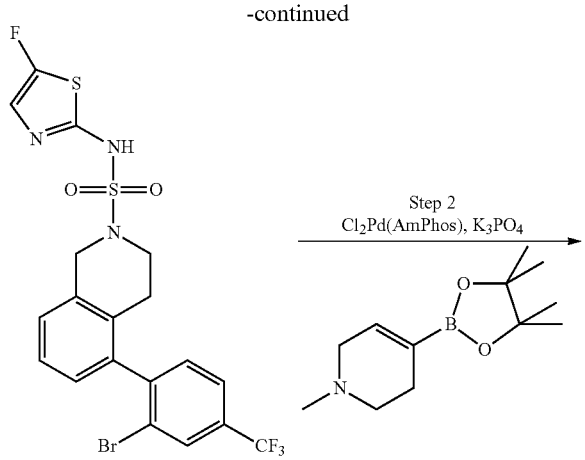

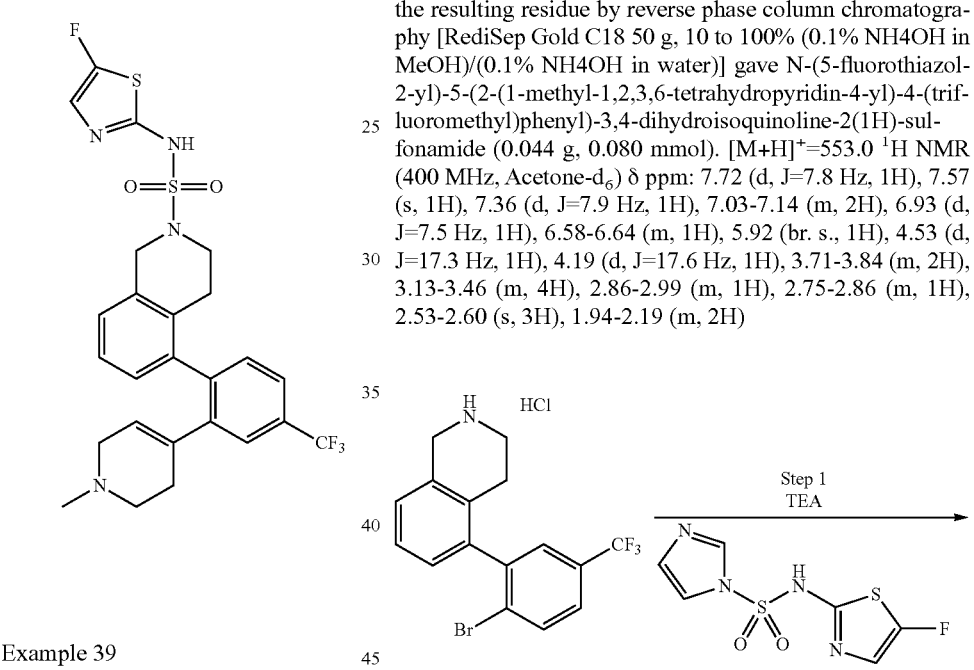

Example 39

N-(5-Fluorothiazol-2-yl)-5-(2-(1-methyl-1,2,3,6-tetrahydropyridin-4-yl)-4-(trifluoromethyl)phenyl)-3,4-dihydroisoquinoline-2(1H)-sulfonamide Step 1: 5-(2-Bromo-4-(trifluoromethyl)phenyl)-N-(5-fluorothiazol-2-yl)-3,4-dihydroisoquinoline-2(1H)-sulfonamide A solution of 5-(2-bromo-4-(trifluoromethyl)phenyl)-1,2,3,4-tetrahydroisoquinoline hydrochloride (Intermediate D, 0.400 g, 1.019 mmol), N-(5-fluorothiazol-2-yl)-1H-imidazole-1-sulfonamide (Intermediate N, 1.012 g, 4.07 mmol), and triethylamine (2.84 ml, 20.37 mmol) in 3 mL THF was heated to 80° C. for 30 minutes. LC/MS showed product so the reaction mixture was diluted with EtOAc and washed with 1 N citric acid. The organics were dried over MgSO4 and concentrated. Purification of the resulting residue by silica gel column chromatography (0 to 100% EtOAc/heptane) gave 5-(2-bromo-4-(trifluoromethyl)phenyl)-N-(5-fluorothiazol-2-yl)-3,4-dihydroisoquinoline-2(1H)-sulfonamide (0.150 g, 0.280 mmol). $^1$H NMR (400 MHz, Acetone-d$_6$) δ ppm: 8.06 (s, 1H), 7.83 (d, J=7.8 Hz, 1H), 7.51-7.57 (m, 1H), 7.24-7.35 (m, 2H), 7.08 (s, 1H), 7.05 (d, J=5.7 Hz, 1H), 4.37 (s, 2H), 3.30-3.39 (m, 2H), 2.47-2.60 (m, 2H)

Step 2: N-(5-Fluorothiazol-2-yl)-5-(2-(1-methyl-1,2,3,6-tetrahydropyridin-4-yl)-4-(trifluoromethyl)phenyl)-3,4-dihydroisoquinoline-2(1H)-sulfonamide A solution of Cl$_2$Pd(AmPhos) (Sigma-Aldrich, St. Louis, Mo., 0.020 g, 0.028 mmol), 1-methyl-4-(4,4,5,5-tetramethyl-1,3,2-dioxaborolan-2-yl)-1,2,3,6-tetrahydropyridine (0.078 g, 0.350 mmol), 5-(2-bromo-4-(trifluoromethyl)phenyl)-N-(5-fluorothiazol-2-yl)-3,4-dihydroisoquinoline-2(1H)-sulfonamide (0.150 g, 0.280 mmol), and potassium phosphate (0.237 g, 1.119 mmol) in 2 mL dioxane 1 mL water, was heated to 110° C. 2 hours. After cooling to rt, the reaction mixture was diluted with EtOAc and washed with 1N citric acid. The organic layer was then concentrated. Purification of the resulting residue by reverse phase column chromatography [RediSep Gold C18 50 g, 10 to 100% (0.1% NH4OH in MeOH)/(0.1% NH4OH in water)] gave N-(5-fluorothiazol-2-yl)-5-(2-(1-methyl-1,2,3,6-tetrahydropyridin-4-yl)-4-(trifluoromethyl)phenyl)-3,4-dihydroisoquinoline-2(1H)-sulfonamide (0.044 g, 0.080 mmol). [M+H]$^+$=553.0 $^1$H NMR (400 MHz, Acetone-d$_6$) δ ppm: 7.72 (d, J=7.8 Hz, 1H), 7.57 (s, 1H), 7.36 (d, J=7.9 Hz, 1H), 7.03-7.14 (m, 2H), 6.93 (d, J=7.5 Hz, 1H), 6.58-6.64 (m, 1H), 5.92 (br. s., 1H), 4.53 (d, J=17.3 Hz, 1H), 4.19 (d, J=17.6 Hz, 1H), 3.71-3.84 (m, 2H), 3.13-3.46 (m, 4H), 2.86-2.99 (m, 1H), 2.75-2.86 (m, 1H), 2.53-2.60 (s, 3H), 1.94-2.19 (m, 2H)

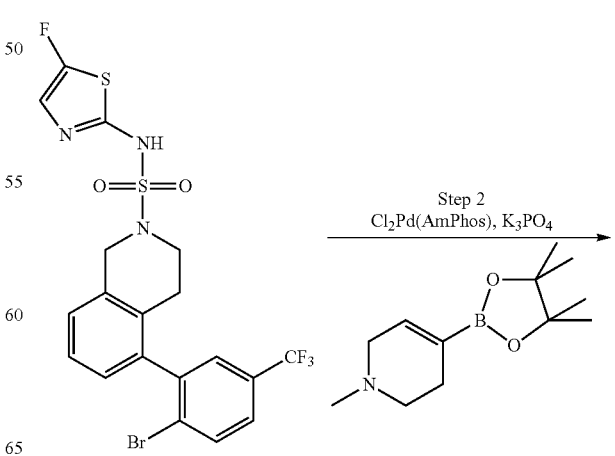

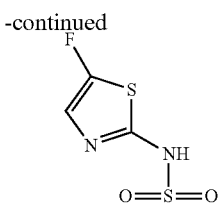

Example 40

N-(5-Fluorothiazol-2-yl)-5-(2-(1-methyl-1,2,3,6-tetrahydropyridin-4-yl)-5-(trifluoromethyl)phenyl)-3,4-dihydroisoquinoline-2(1H)-sulfonamide

Step 1: 5-(2-Bromo-5-(trifluoromethyl)phenyl)-N-(5-fluorothiazol-2-yl)-3,4-dihydroisoquinoline-2(1H)-sulfonamide A solution of 5-(2-bromo-5-(trifluoromethyl)phenyl)-1,2,3,4-tetrahydroisoquinoline hydrochloride (Intermediate T, 0.200 g, 0.509 mmol), N-(5-fluorothiazol-2-yl)-1H-imidazole-1-sulfonamide (Intermediate N, 0.506 g, 2.037 mmol), and triethylamine (1.420 ml, 10.19 mmol) in 3 mL THF was heated to 80° C. for 30 minutes. The reaction mixture was diluted with EtOAc and washed with 1N citric acid. The organics were dried over MgSO4 and concentrated. Purification of the resulting residue by silica gel column chromatography (0 to 100% EtOAc/heptane) gave 5-(2-bromo-5-(trifluoromethyl)phenyl)-N-(5-fluorothiazol-2-yl)-3,4-dihydroisoquinoline-2(1H)-sulfonamide (0.104 g, 0.194 mmol).

Step 2: N-(5-Fluorothiazol-2-yl)-5-(2-(1-methyl-1,2,3,6-tetrahydropyridin-4-yl)-5-(trifluoromethyl)phenyl)-3,4-dihydroisoquinoline-2(1H)-sulfonamide A solution of Cl2Pd(AmPhos) (Sigma-Aldrich, St. Louis, Mo., 0.014 g, 0.019 mmol), 1-methyl-4-(4,4,5,5-tetramethyl-1,3,2-dioxaborolan-2-yl)-1,2,3,6-tetrahydropyridine (0.054 g, 0.242 mmol), 5-(2-bromo-5-(trifluoromethyl)phenyl)-N-(5-fluorothiazol-2-yl)-3,4-dihydroisoquinoline-2(1H)-sulfonamide (0.104 g, 0.194 mmol), and potassium phosphate (0.165 g, 0.776 mmol) in 2 mL dioxane and 1 mL water, was heated to 110° C. 2 hours. The reaction mixture was allowed to cool to room temperature, was diluted with EtOAc and washed with 1N citric acid. The organic layer was then concentrated. Purification of the resulting residue by reverse phase column chromatography [RediSep Gold C18 50 g, 10 to 100% (0.1% NH4OH in MeOH)/(0.1% NH4OH in water)] gave N-(5-fluorothiazol-2-yl)-5-(2-(1-methyl-1,2,3,6-tetrahydropyridin-4-yl)-5-(trifluoromethyl)phenyl)-3,4-dihydroisoquinoline-2(1H)-sulfonamide (0.011 g, 0.020 mmol). [M+H]+=553.0 $^1$H NMR (400 mHz, Acetone-$d_6$) δ ppm: 7.70-7.77 (m, 1H), 7.50 (d, J=8.1 Hz, 1H), 7.42 (s, 1H), 7.05-7.14 (m, 2H), 6.93 (d, J=6.7 Hz, 1H), 6.62 (d, J=0.9 Hz, 1H), 5.87-5.93 (m, 1H), 4.48-4.56 (d, J=17.4 Hz, 1H), 4.19 (d, J=17.4 Hz, 1H), 3.70-3.84 (m, 2H), 3.32-3.43 (m, 1H), 3.12-3.32 (m, 3H), 2.87-2.98 (m, 1H), 2.76-2.82 (m, 1H), 2.57 (s, 3H), 1.98-2.04 (m, 2H)

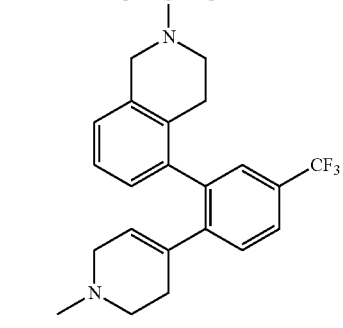

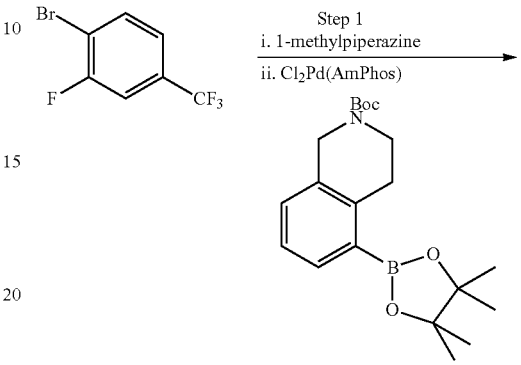

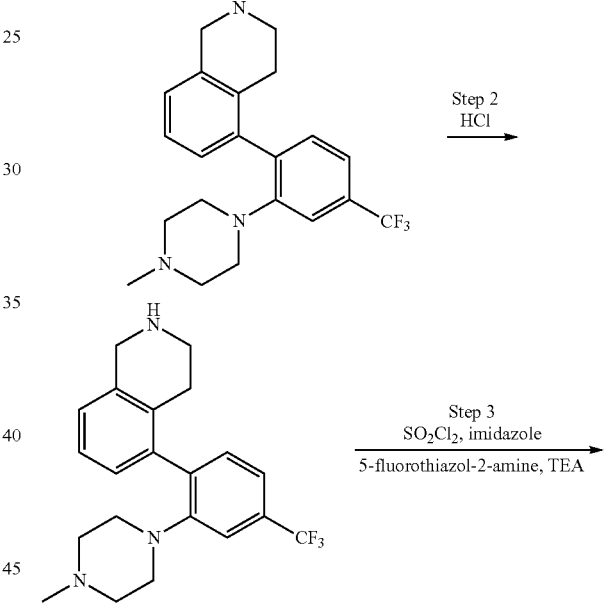

Example 41

N-(5-Fluorothiazol-2-yl)-5-(2-(4-methylpiperazin-1-yl)-4-(trifluoromethyl)phenyl)-3,4-dihydroisoquinoline-2(1H)-sulfonamide

Step 1: tert-Butyl 5-(2-(4-methylpiperazin-1-yl)-4-(trifluoromethyl)phenyl)-3,4-dihydroisoquinoline-2(1H)-carboxylate A microwave vial charged with 1-methylpiperazine (2.74 ml, 24.69 mmol) and 1-bromo-2-fluoro-4-(trifluoromethyl)benzene (2.000 g, 8.23 mmol) was heated to 180° C. in a microwave reactor for 90 minutes. The reaction mixture was concentrated then transferred to a vial charged with $Cl_2Pd$ (AmPhos) (Sigma-Aldrich, St. Louis, Mo., 0.291 g, 0.412 mmol), tert-butyl 5-(4,4,5,5-tetramethyl-1,3,2-dioxaborolan-2-yl)-3,4-dihydroisoquinoline-2(1H)-carboxylate (ASW Medchem, Brunswick, N.J., 2.96 g, 8.23 mmol), and potassium phosphate (8.74 g, 41.2 mmol). 8 mL dioxane and 4 mL water were added, and the reaction mixture was heated to 120° C. for 2 hours. After cooling to rt, the reaction mixture was poured into water and extracted with DCM. The organics were concentrated then purified by reverse phase column chromatography [RediSep Gold C18 150 g, 15 to 100% (0.1% $NH_4OH$ in MeOH)/(0.1% $NH_4OH$ in water)] yielding tert-butyl 5-(2-(4-methylpiperazin-1-yl)-4-(trifluoromethyl)phenyl)-3,4-dihydroisoquinoline-2(1H)-carboxylate (1.68 g, 3.53 mmol).

Step 2: 5-(2-(4-Methylpiperazin-1-yl)-4-(trifluoromethyl)phenyl)-1,2,3,4-tetrahydroisoquinoline A solution of tert-butyl 5-(2-(4-methylpiperazin-1-yl)-4-(trifluoromethyl)phenyl)-3,4-dihydroisoquinoline-2(1H)-carboxylate (1.680 g, 3.53 mmol) in 4 mL THF was treated with HCl 4N in dioxane (8.83 ml, 35.3 mmol) and was heated to reflux with a heat gun. The reaction mixture was allowed to stir for an additional hour then the reaction mixture was concentrated. Purification of the resulting residue by reverse phase column chromatography [RediSep Gold C18 150 g, 5-100% (0.1% $NH_4OH$ in MeOH)/(0.1% $NH_4OH$ in water)] gave 5-(2-(4-methylpiperazin-1-yl)-4-(trifluoromethyl)phenyl)-1,2,3,4-tetrahydroisoquinoline (1.031 g, 2.75 mmol,) as a light yellow solid.

Step 3: N-(5-Fluorothiazol-2-yl)-5-(2-(4-methylpiperazin-1-yl)-4-(trifluoromethyl)phenyl)-3,4-dihydroisoquinoline-2(1H)-sulfonamide A solution of 1H-imidazole (0.464 g, 6.82 mmol) and 5-fluorothiazol-2-amine hydrochloride (0.264 g, 1.705 mmol) in 6 mL DCM was cooled to −78° C. and was treated with sulfuryl chloride (0.139 ml, 1.705 mmol). After stirring for 10 minutes, the reaction mixture was placed in a 0° C. bath and was allowed to stir for an additional hour. The organics were decanted off and the remaining solid was treated with a solution of 5-(2-(4-methylpiperazin-1-yl)-4-(trifluoromethyl)phenyl)-1,2,3,4-tetrahydroisoquinoline (derived above, 0.320 g, 0.852 mmol) in 5 mL DCM followed by DIPEA (1.786 ml, 10.23 mmol). The reaction mixture was then heated to 80° C. for 30 minutes. The reaction mixture was diluted with EtOAc and washed with 1N citric acid. The organics were concentrated then purified directly by reverse phase column chromatography [RediSep Gold C18 50 g, 10 to 100% (0.1% $NH_4OH$ in MeOH)/(0.1% $NH_4OH$ in water)] yielding N-(5-fluorothiazol-2-yl)-5-(2-(4-methylpiperazin-1-yl)-4-(trifluoromethyl)phenyl)-3,4-dihydroisoquinoline-2(1H)-sulfonamide (0.062 g, 0.112 mmol). $[M+H]^+=556.0$ $^1H$ NMR (400 MHz, Acetone-$d_6$) δ ppm: 7.26-7.41 (m, 4H), 7.13-7.21 (m, 2H), 6.96-6.98 (m, 1H), 4.31-4.47 (m, 2H), 3.47-3.59 (m, 1H), 3.15-3.26 (m, 1H), 2.99-3.12 (m, 4H), 2.87-2.99 (m, 4H), 2.46-2.54 (m, 1H), 2.36-2.45 (m, 1H), 2.31-2.36 (m, 3H)

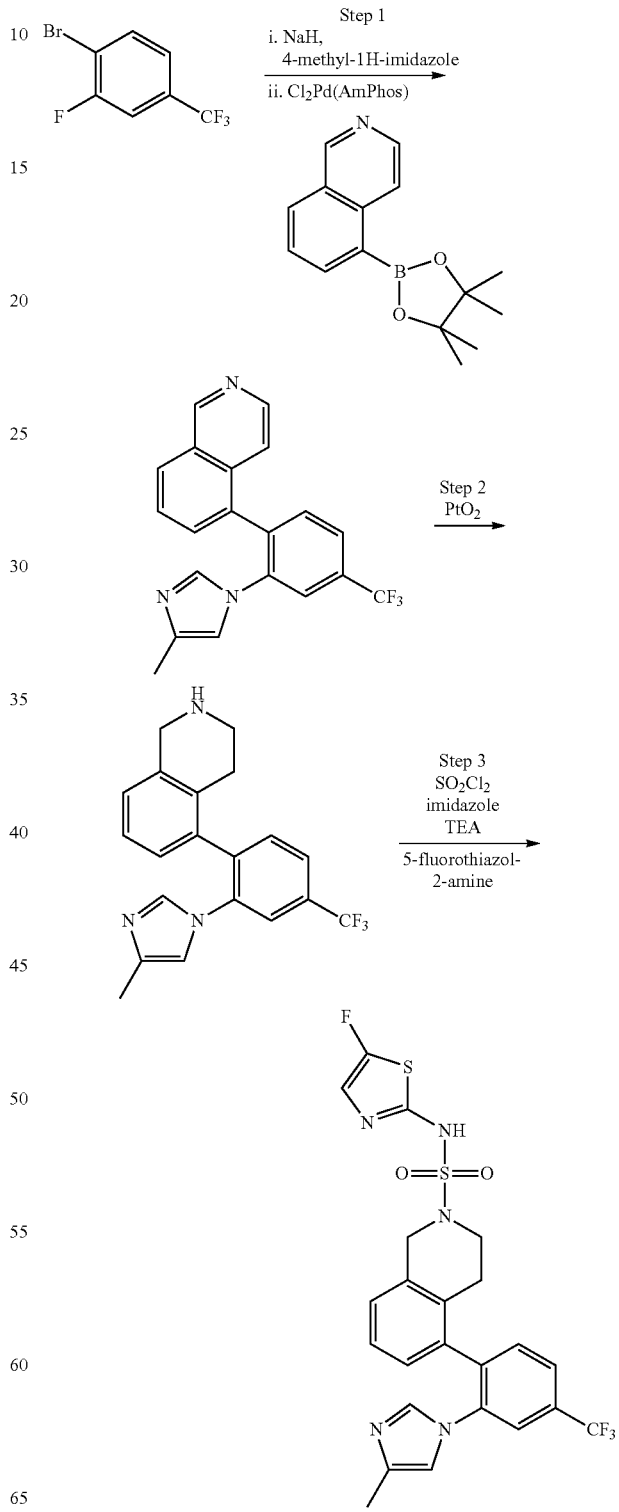

Example 42

N-(5-Fluorothiazol-2-yl)-5-(2-(4-methylpiperazin-1-yl)-4-(trifluoromethyl)phenyl)-3,4-dihydroisoquinoline-2(1H)-sulfonamide

Step 1: 5-(2-(4-Methyl-1H-imidazol-1-yl)-4-(trifluoromethyl)phenyl)isoquinoline A suspension of sodium hydride 60% (0.330 g, 13.75 mmol) in 8 mL DMF was cooled to 0° C. and was treated with 4-methyl-1H-imidazole (0.676 g, 8.23 mmol). After stirring for 40 minutes, 1-bromo-2-fluoro-4-(trifluoromethyl)benzene (1.180 ml, 8.23 mmol) was added, and the reaction mixture was heated to 120° C. for 90 minutes. At this point Cl$_2$Pd(AmPhos) (Sigma-Aldrich, St. Louis, Mo., 0.291 g, 0.412 mmol), isoquinolin-5-ylboronic acid (1.424 g, 8.23 mmol), potassium phosphate (6.99 g, 32.9 mmol), 16 mL dioxane and 12 mL water were added, and the reaction mixture was heated to 120° C. overnight. The reaction mixture was poured into saturated NaHCO$_3$ solution and was extracted with DCM. The organics were concentrated then purified by reverse phase column chromatography [RediSep Gold C18 150 g, 15 to 100% (0.1% NH4OH in MeOH)/(0.1% NH4OH in water)] yielding 5-(2-(4-methyl-1H-imidazol-1-yl)-4-(trifluoromethyl)phenyl)isoquinoline (1.435 g, 4.06 mmol) as an about 4:1 mixture of isomers.

Step 2: 5-(2-(4-Methyl-1H-imidazol-1-yl)-4-(trifluoromethyl)phenyl)-1,2,3,4-tetrahydroisoquinoline A solution of 5-(2-(4-methyl-1H-imidazol-1-yl)-4-(trifluoromethyl)phenyl)isoquinoline (1.435 g, 4.06 mmol) in 15 mL MeOH was treated with platinum(IV) oxide (0.092 g, 0.406 mmol) and acetic acid (0.697 ml, 12.18 mmol) and was placed under 45 psi (4559.6 kpa) H$_2$ for 3 hours. The reaction mixture was filtered through a plug of diatomaceous earth eluting with EtOAc. The filtrate was concentrated then purified directly be reverse phase column chromatography [RediSep Gold C18 150 g, 5 to 100% (0.1% NH$_4$OH in MeOH)/(0.1% NH$_4$OH in water)] yielding 5-(2-(4-methyl-1H-imidazol-1-yl)-4-(trifluoromethyl)phenyl)-1,2,3,4-tetrahydroisoquinoline (0.808 g, 2.261 mmol).

Step 3: N-(5-Fluorothiazol-2-yl)-5-(2-(4-methyl-1H-imidazol-1-yl)-4-(trifluoromethyl)phenyl)-3,4-dihydroisoquino line-2(1H)-sulfonamide A solution of 5-fluorothiazol-2-amine hydrochloride (Milestone Pharmatech, Brunswick, N.J., 0.692 g, 4.48 mmol) and imidazole (1.219 g, 17.91 mmol) in 10 mL DCM was cooled to −78° C. and was treated with sulfuryl chloride (0.364 ml, 4.48 mmol). After stirring for 10 minutes, the reaction mixture was placed in a 0° C. bath and was allowed to stir for one hour at which point about 3 mL heptane was added, and the organics were decanted off. The resulting solid was treated with a solution of 5-(2-(4-methyl-1H-imidazol-1-yl)-4-(trifluoromethyl)phenyl)-1,2,3,4-tetrahydroisoquinoline (0.800 g, 2.239 mmol) in 15 mL DCM followed by DIPEA (4.69 ml, 26.9 mmol) and was heated to 80° C. for 30 minutes. The reaction mixture was poured into 1N citric acid solution and was extracted with EtOAc. The organics were concentrated then purified directly by reverse phase column chromatography [RediSep Gold C18 150 g, 10 to 100% (0.1% NH$_4$OH in MeOH)/(0.1% NH$_4$OH in water)] yielding N-(5-fluorothiazol-2-yl)-5-(2-(4-methyl-1H-imidazol-1-yl)-4-(trifluoromethyl)phenyl)-3,4-dihydroisoquinoline-2(1H)-sulfonamide (0.005 g, 9.30 μmol). [M+H]$^+$=538.0 $^1$H NMR (400 MHz, Acetone-d$_6$) δ ppm: 7.93 (s, 1H), 7.88 (d, J=8.0 Hz, 1H), 7.67 (d, J=8.0 Hz, 1H), 7.28 (s, 1H), 7.23 (s, 1H), 7.09-7.20 (m, 2H), 7.02 (d, J=7.0 Hz, 1H), 6.99 (d, J=0.7 Hz, 1H), 4.25-4.43 (m, 2H), 3.78-3.83 (m, 1H), 3.18-3.28 (m, 1H), 2.45-2.55 (m, 1H), 2.33-2.42 (m, 1H), 2.14 (s, 3H)

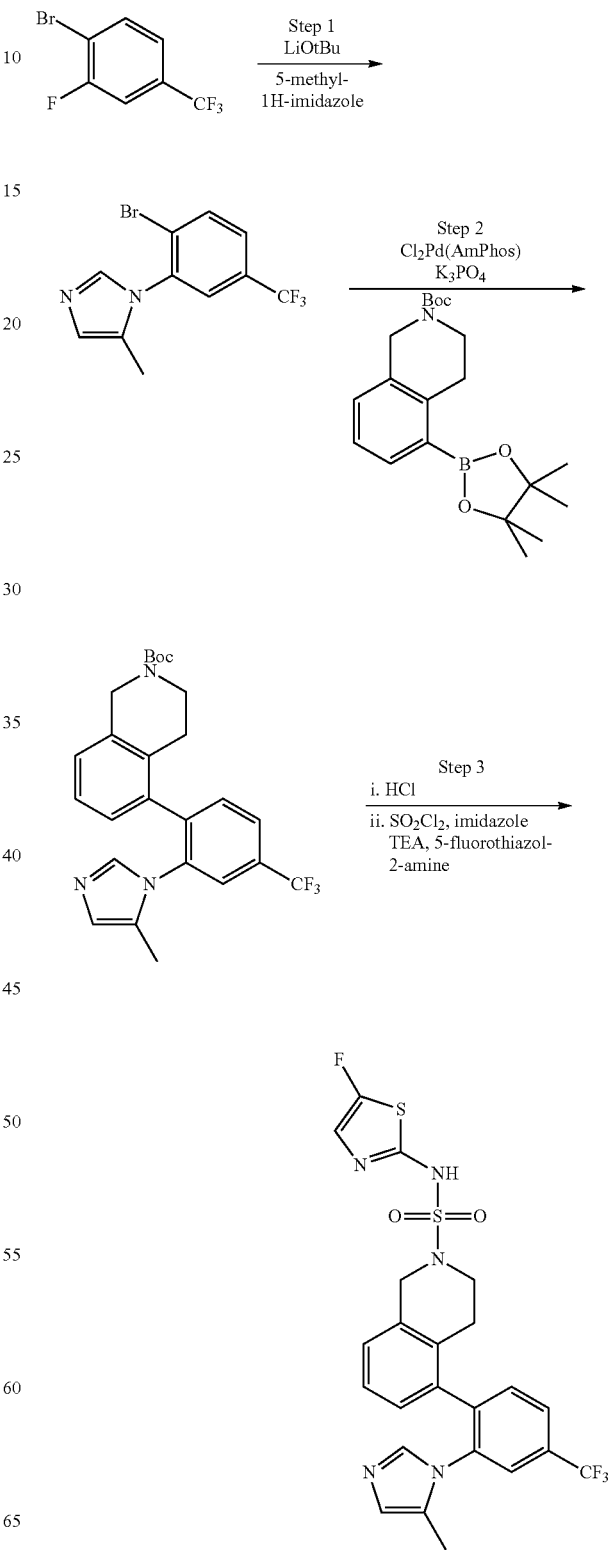

Example 43

N-(5-Fluorothiazol-2-yl)-5-(2-(5-methyl-1H-imidazol-1-yl)-4-(trifluoromethyl)phenyl)-3,4-dihydroisoquinoline-2(1H)-sulfonamide Step 1: 1-(2-Bromo-5-(trifluoromethyl)phenyl)-5-methyl-1H-imidazole A solution of 4-methyl-1H-imidazole (1.352 g, 16.46 mmol) in 20 mL THF was treated with lithium tert-butoxide 1N in hexane (16.46 ml, 16.46 mmol) and was allowed to stir for one hour. The reaction mixture was concentrated and then transferred to a microwave vial charged with 1-bromo-2-fluoro-4-(trifluoromethyl)benzene (2.360 ml, 16.46 mmol) and 10 mL dioxane. The reaction mixture was heated to 180° C. in a microwave reactor for one hour. After cooling to room temperature, the reaction mixture was poured into saturated $NH_4Cl$ solution and was extracted with DCM. The organics were concentrated. then purified directly by silica gel column chromatography (0 to 50% EtOAc/heptane) yielding 1-(2-bromo-5-(trifluoromethyl)phenyl)-5-methyl-1H-imidazole (0.710 g, 2.327 mmol).

Step 2: tert-Butyl 5-(2-(5-methyl-1H-imidazol-1-yl)-4-(trifluoromethyl)phenyl)-3,4-dihydroisoquinoline-2(1H)-carboxylate A solution of $Cl_2Pd(AmPhos)$ (Sigma-Aldrich, St. Louis, Mo., 0.165 g, 0.233 mmol), tert-butyl 5-(4,4,5,5-tetramethyl-1,3,2-dioxaborolan-2-yl)-3,4-dihydroisoquinoline-2(1H)-carboxylate (ASW Medchem, Brunswick, N.J., 1.254 g, 3.49 mmol), 1-(2-bromo-5-(trifluoromethyl)phenyl)-5-methyl-1H-imidazole (derived above, 0.710 g, 2.327 mmol), and potassium phosphate (1.976 g, 9.31 mmol) in 10 mL dioxane 5 mL water was heated to 120° C. for 2 hours. After cooling to room temperature, the reaction mixture was diluted with EtOAc and the organics were concentrated. The resulting residue was purified by silica gel column chromatography (0 to 100% EtOAc/heptane) yielding tert-butyl 5-(2-(5-methyl-1H-imidazol-1-yl)-4-(trifluoromethyl)phenyl)-3,4-dihydroisoquinoline-2(1H)-carboxylate (0.450 g, 0.984 mmol).

Step 3: N-(5-Fluorothiazol-2-yl)-5-(2-(5-methyl-1H-imidazol-1-yl)-4-(trifluoromethyl)phenyl)-3,4-dihydroisoquinoline-2(1H)-sulfonamide A solution of tert-butyl 5-(2-(5-methyl-1H-imidazol-1-yl)-4-(trifluoromethyl)phenyl)-3,4-dihydroisoquinoline-2(1H)-carboxylate (0.450 g, 0.984 mmol) in 2 mL THF was treated with HCl 4N in dioxane (1.230 ml, 4.92 mmol) and was allowed to stir over the weekend at room temperature. The reaction mixture was diluted with heptane and the resulting solid was collected and dried and used without further purification. A separate solution of imidazole (0.536 g, 7.87 mmol) and 5-fluorothiazol-2-amine hydrochloride (0.304 g, 1.967 mmol) in 10 mL DCM was cooled to −78° C. and was treated with sulfuryl chloride (0.160 ml, 1.967 mmol). After stirring for 10 minutes, the reaction mixture was placed in a 0° C. bath and was allowed to stir for one hour. The tetrahydroisoquinoline HCl salt derived above was added as a solution in 7 mL DCM followed by DIPEA (2.062 ml, 11.80 mmol) and the reaction mixture was heated to 80° C. (sealed vial) for one hour. After cooling to rt, the reaction mixture was poured into 1N citric acid solution and was extracted with EtOAc. The organics were concentrated then purified directly by reverse phase column chromatography [RediSep Gold C18 100 g, 15 to 100% (0.1% $NH_4OH$ in MeOH)/(0.1% $NH_4OH$ in water)] then normal phase silica gel column chromatography (0 to 100% EtOAc/heptane) yielding N-(5-fluorothiazol-2-yl)-5-(2-(5-methyl-1H-imidazol-1-yl)-4-(trifluoromethyl)phenyl)-3,4-dihydroisoquinoline-2(1H)-sulfonamide (0.081 g, 0.151 mmol). $[M+H]^+=538.0$ $^1H$ NMR (400 MHz, Acetone-$d_6$) δ ppm: 7.95-8.03 (m, 2H), 7.76 (d, J=8.0 Hz, 1H), 7.48 (d, J=1.0 Hz, 1H), 6.99-7.04 (m, 2H), 6.96 (s, 1H), 6.75-6.79 (m, 1H), 6.73 (s, 1H), 4.24-4.42 (m, 2H), 3.80-3.91 (m, 1H), 3.25-3.39 (m, 1H), 2.55-2.73 (m, 2H), 2.20 (s, 3H)

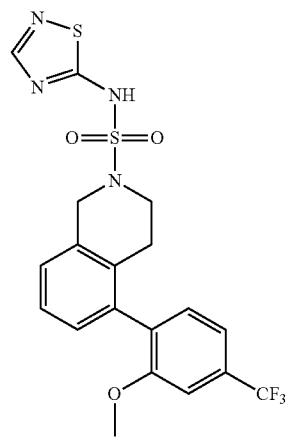 [SMILES: COc1cc(C(F)(F)F)ccc1-c1cccc2c1CCN(S(=O)(=O)Nc1ncns1)C2]

Example 44

5-(2-Methoxy-4-(trifluoromethyl)phenyl)-N-(1,2,4-thiadiazol-5-yl)-3,4-dihydroisoquinoline-2(1H)-sulfonamide The title compound was prepared in a manner analogous to Example 1, except that (2-methoxy-4-(trifluoromethyl)phenyl)boronic acid (Combi-Blocks, San Diego, Calif.) was used in place of (2-(1-methyl-1H-pyrazol-5-yl)-4-(trifluoromethyl)phenyl)boronic acid. $[M+H]^+=471.0$ $^1H$ NMR (400 MHz, Acetone-$d_6$) δ ppm: 8.29 (s, 1H), 7.29-7.38 (m, 3H), 7.25 (t, J=7.7 Hz, 1H), 7.18 (d, J=8.4 Hz, 1H), 7.05 (d, J=6.6 Hz, 1H), 4.28-4.46 (m, 2H), 3.87 (s, 3H), 3.41 (dt, J=12.0, 5.8 Hz, 1H), 3.18-3.28 (m, 1H), 2.66-2.78 (m, 2H), 2.46-2.56 (m, 1H)

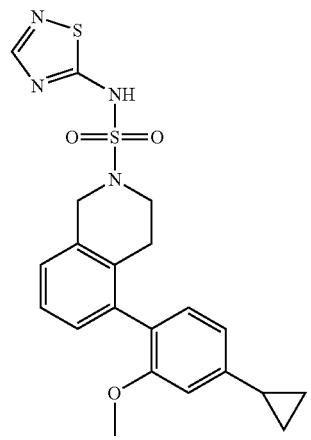 [SMILES: COc1cc(C2CC2)ccc1-c1cccc2c1CCN(S(=O)(=O)Nc1ncns1)C2]

Example 45

5-(4-Cyclopropyl-2-methoxyphenyl)-N-(1,2,4-thiadiazol-5-yl)-3,4-dihydroisoquinoline-2(1H)-sulfonamide The title compound was prepared in a manner analogous to Example 1, except that 2-(4-cyclopropyl-2-methoxyphenyl)-4,4,5,5-tetramethyl-1,3,2-dioxaborolane (Intermediate W) was used in place of (2-(1-methyl-1H-pyrazol-5-yl)-4-(trifluoromethyl)phenyl)boronic acid. [M+H]$^+$=443.0 $^1$H NMR (400 MHz, Acetone-d$_6$) δ ppm: 8.24-8.27 (m, 1H), 7.19 (t, J=7.6 Hz, 1H), 7.09 (d, J=7.0 Hz, 1H), 6.99 (d, J=7.6 Hz, 1H), 6.94 (d, J=7.7 Hz, 1H), 6.81 (d, J=1.6 Hz, 1H), 6.72 (dd, J=7.7, 1.7 Hz, 1H), 4.25-4.44 (m, 2H), 3.74 (s, 3H), 3.37-3.42 (m, 1H), 3.14-3.25 (m, 1H), 2.66-2.81 (m, 1H), 2.43-2.55 (m, 1H), 1.94-2.00 (m, 1H), 0.92-1.02 (m, 2H), 0.70-0.79 (m, 2H)

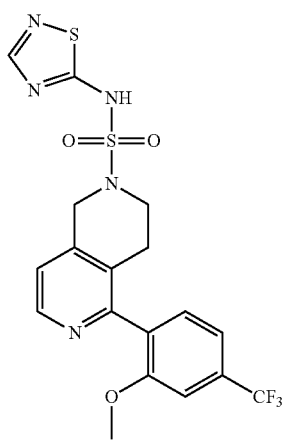 [SMILES: COc1cc(C(F)(F)F)ccc1-c1nccc2c1CCN(S(=O)(=O)Nc1ncns1)C2]

Example 46

5-(2-Methoxy-4-(trifluoromethyl)phenyl)-N-(1,2,4-thiadiazol-5-yl)-3,4-dihydro-2,6-naphthyridine-2(1H)-sulfonamide The title compound was prepared in a manner analogous to Example 1, except that (2-methoxy-4-(trifluoromethyl)phenyl)boronic acid was used in place of (2-(1-methyl-1H-pyrazol-5-yl)-4-(trifluoromethyl)phenyl)boronic acid and 5-chloro-N-(1,2,4-thiadiazol-5-yl)-3,4-dihydro-2,6-naphthyridine-2(1H)-sulfonamide (Intermediate V) was used in place of 5-bromo-N-(1,2,4-thiadiazol-5-yl)-3,4-dihydroisoquinoline-2(1H)-sulfonamide. [M+H]$^+$=472.0 $^1$H NMR (400 MHz, Acetone-d$_6$) δ ppm: 8.41 (d, J=5.1 Hz, 1H), 8.25 (s, 1H), 7.35-7.44 (m, 3H), 7.20 (d, J=5.1 Hz, 1H), 4.26-4.51 (m, 2H), 3.89 (s, 3H), 3.43-3.56 (m, 1H), 3.15-3.26 (m, 1H), 2.82-2.93 (m., 1H), 2.40-2.56 (m, 1H)

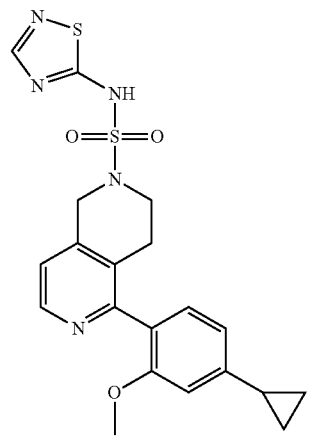 [SMILES: COc1cc(C2CC2)ccc1-c1nccc2c1CCN(S(=O)(=O)Nc1ncns1)C2]

Example 47

5-(4-Cyclopropyl-2-methoxyphenyl)-N-(1,2,4-thiadiazol-5-yl)-3,4-dihydro-2,6-naphthyridine-2(1H)-sulfonamide The title compound was prepared in a manner analogous to Example 1, except that 2-(4-cyclopropyl-2-methoxyphenyl)-4,4,5,5-tetramethyl-1,3,2-dioxaborolane (Intermediate W) was used in place of (2-(1-methyl-1H-pyrazol-5-yl)-4-(trifluoromethyl)phenyl)boronic acid and 5-chloro-N-(1,2,4-thiadiazol-5-yl)-3,4-dihydro-2,6-naphthyridine-2(1H)-sulfonamide (Intermediate V) was used in place of 5-bromo-N-(1,2,4-thiadiazol-5-yl)-3,4-dihydroisoquinoline-2(1H)-sulfonamide. [M+H]$^+$=444.0 $^1$H NMR (400 MHz, Acetone-d$_6$) δ ppm: 8.35 (d, J=5.0 Hz, 1H), 8.12-8.17 (m, 1H), 7.10 (d, J=5.1 Hz, 1H), 7.05 (d, J=7.8 Hz, 1H), 6.82 (d, J=1.6 Hz, 1H), 6.74 (d, J=7.7 Hz, 1H), 4.28-4.43 (m, 2H), 3.76 (s, 3H), 3.43-3.56 (m, 1H), 2.79-3.22 (br. m, 2H), 2.38-2.52 (br. m, 1H), 1.94-2.02 (m, 1H), 0.93-1.03 (m, 2H), 0.71-0.81 (m, 2H)

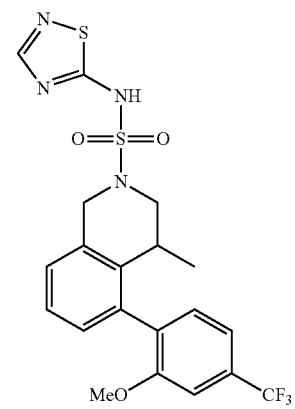 [SMILES: COc1cc(C(F)(F)F)ccc1-c1cccc2c1C(C)CN(S(=O)(=O)Nc1ncns1)C2]

Example 48

Racemic 5-(2-Methoxy-4-(trifluoromethyl)phenyl)-4-methyl-N-(1,2,4-thiadiazol-5-yl)-3,4-dihydroisoquinoline-2(1H)-sulfonamide The title compound was prepared in a manner analogous to Example 33, except that 5-(2-methoxy-4-(trifluoromethyl)

phenyl)-4-methyl-1,2,3,4-tetrahydroisoquinoline (Intermediate X) was used in place of 8-(2-(1H-imidazol-1-yl)-4-(trifluoromethyl)phenyl)-1,2,3,4-tetrahydroisoquinoline [M+H]$^+$=481.0 $^1$H NMR (400 MHz, Acetone-d$_6$) δ ppm: 7.25-7.46 (m, 6H), 7.06 (d, J=2.2 Hz, 1H), 4.83-5.07 (m, 1H), 4.34-4.63 (m, 1H), 3.90-4.02 (m, 1H), 3.87 (s, 3H), 3.24-3.66 (m, 1H), 2.94-3.17 (m, 1H), 0.81-0.94 (m, 3H)

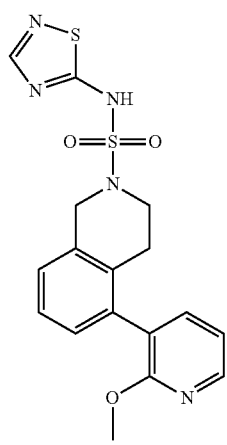

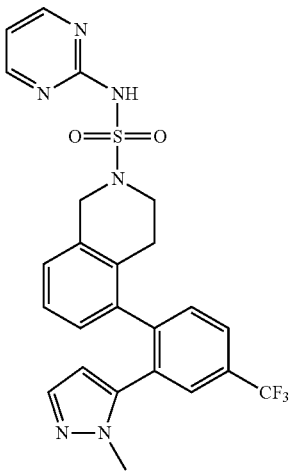 [SMILES: Cn1nccc1-c1cc(C(F)(F)F)ccc1-c1cccc2c1CCN(S(=O)(=O)Nc1ncccn1)C2]

Example 50

5-(2-Methoxypyridin-3-yl)-N-(1,2,4-thiadiazol-5-yl)-3,4-dihydroisoquinoline-2(1H)-sulfonamide The title compound was prepared in a manner analogous to Example 1, except that 2-methoxy-3-(4,4,5,5-tetramethyl-1,3,2-dioxaborolan-2-yl)pyridine was used in place of (2-(1-methyl-1H-pyrazol-5-yl)-4-(trifluoromethyl)phenyl)boronic acid. [M+H]$^+$=404.3 $^1$H NMR (400 MHz, DMSO-d$_6$) δ ppm: 8.40 (s, 1H), 8.21 (dd, J=5.0, 1.8 Hz, 1H), 7.53 (dd, J=7.2, 1.9 Hz, 1H), 7.17-7.25 (m, 2H), 7.01-7.09 (m, 2H), 4.33 (br. s., 1H), 4.26 (br. s., 1H), 3.81 (s, 3H), 3.17 (s, 2H), 2.54-2.68 (m, 1H), 2.44-2.54 (m, 1H)

Example 49

5-(2-(1-Methyl-1H-pyrazol-5-yl)-4-(trifluoromethyl)phenyl)-N-(pyrimidin-2-yl)-3,4-dihydroisoquinoline-2(1H)-sulfonamide A microwave vial was charged with 5-(2-(1-methyl-1H-pyrazol-5-yl)-4-(trifluoromethyl)phenyl)-1,2,3,4-tetrahydroisoquinoline (Intermediate O, 55.90 mg, 0.156 mmol), 2-oxo-N-(pyrimidin-2-yl)oxazolidine-3-sulfonamide (Intermediate Q, 96 mg, 0.391 mmol), and acetonitrile (587 μl) to give a suspension. Triethylamine (218 μl, 1.564 mmol) was added resulting in the formation of a yellow solution. The vial was sealed and heated in a microwave reactor for 30 min at 130° C. The mixture was concentrated, then chromatographed on a 12 g silica gel column with 0 to 10% MeOH/DCM to provide 5-(2-(1-methyl-1H-pyrazol-5-yl)-4-(trifluoromethyl)phenyl)-N-(pyrimidin-2-yl)-3,4-dihydroisoquinoline-2(1H)-sulfonamide (33.42 mg, 0.065 mmol) as a light-yellow solid. [M+H]$^+$=515.2. $^1$H NMR (400 MHz, DMSO-d$_6$) δ ppm=11.19 (br. s., 1H), 8.48 (d, J=4.9 Hz, 2H), 7.88 (dd, J=1.4, 8.1 Hz, 1H), 7.83 (br. s, 1H), 7.50 (d, J=8.0 Hz, 1H), 7.22 (d, J=2.0 Hz, 1H), 7.20-7.10 (m, 2H), 7.03 (t, J=4.8 Hz, 1H), 6.89 (dd, J=1.3, 7.4 Hz, 1H), 5.88 (d, J=1.9 Hz, 1H), 4.62-4.49 (m, 2H), 3.59-3.52 (m, 1H), 3.48 (s, 3H), 3.23 (ddd, J=4.3, 8.0, 12.4 Hz, 1H), 2.59 (ddd, J=4.9, 8.3, 16.1 Hz, 1H), 2.28-2.19 (m, 1H).

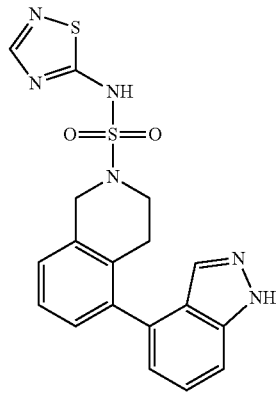 [SMILES: O=S(=O)(Nc1ncns1)N1CCc2c(cccc2-c2cccc3[nH]ncc23)C1]

Example 51

5-(1H-Indazol-4-yl)-N-(1,2,4-thiadiazol-5-yl)-3,4-dihydroisoquinoline-2(1H)-sulfonamide The title compound was prepared in a manner analogous to Example 1, except that 4-(4,4,5,5-tetramethyl-1,3,2-dioxaborolan-2-yl)-1H-indazole was used in place of (2-(1-methyl-1H-pyrazol-5-yl)-4-(trifluoromethyl)phenyl)boronic acid. [M+H]$^+$=413.3 $^1$H NMR (400 MHz, DMSO-d$_6$) δ ppm: 13.19 (br. s., 1H), 8.40 (s, 1H), 7.68 (s, 1H), 7.54 (d, J=8.4 Hz, 1H), 7.40 (dd, J=8.3, 7.0 Hz, 1H), 7.18-7.32 (m, 3H), 6.98 (d, J=6.9 Hz, 1H), 4.36 (s, 2H), 3.22-3.27 (m, 2H), 2.59-2.65 (m, 2H)

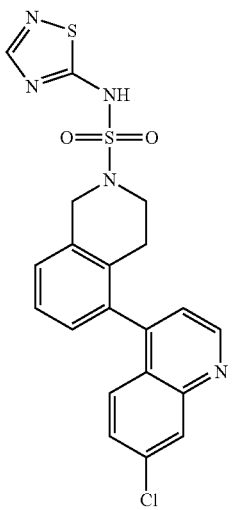 [SMILES: O=S(=O)(Nc1ncns1)N1CCc2c(cccc2-c2ccnc3cc(Cl)ccc23)C1]

Example 52

7-chloro-N-(1,2,4-Thiadiazol-5-yl)-3',4'-dihydro-[4,5'-biisoquinoline]-2'(1'H)-sulfonamide

The title compound was prepared in a manner analogous to Example 1, except that 7-chloro-4-(4,4,5,5-tetramethyl-1,3,2-dioxaborolan-2-yl)isoquinoline was used in place of (2-(1-methyl-1H-pyrazol-5-yl)-4-(trifluoromethyl)phenyl)boronic acid. [M+H]$^+$=458.3 $^1$H NMR (400 MHz, DMSO-d$_6$) δ ppm: 9.04 (d, J=4.9 Hz, 1H), 8.42 (s, 1H), 8.20 (d, J=1.9 Hz, 1H), 7.58-7.68 (m, 1H), 7.35-7.54 (m, 4H), 7.14-7.19 (m, 1H), 4.32-4.44 (m, 2H), 3.18-3.25 (m, 2H), 2.46-2.54 (m, 1H), 2.24-2.30 (m, 1H)

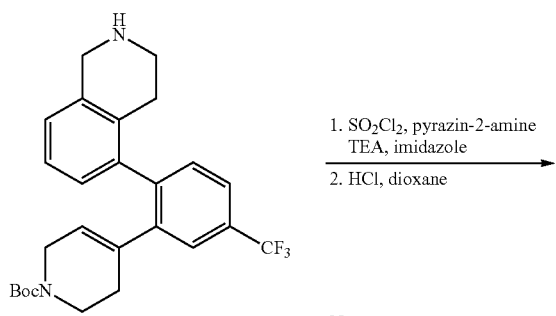

Example 53

N-(Pyrazin-2-yl)-5-(2-(1,2,3,6-tetrahydropyridin-4-yl)-4-(trifluoromethyl)phenyl)-3,4-dihydroisoquinoline-2(1H)-sulfonamide hydrochloride

A solution of 1H-imidazole (0.238 g, 3.49 mmol) and pyrazin-2-amine (0.083 g, 0.872 mmol) in 5 mL DCM and 1 mL DMF was cooled to −10° C. and treated with sulfuryl chloride (0.071 ml, 0.872 mmol). After stirring for 15 minutes, the cooling bath was removed, and the reaction mixture was allowed to stir for an additional 15 minutes. The reaction mixture was then treated with tert-butyl 4-(2-(1,2,3,4-tetrahydroisoquinolin-5-yl)-5-(trifluoromethyl)phenyl)-5,6-dihydropyridine-1(2H)-carboxylate (Example 46, Step 2, 0.200 g, 0.436 mmol) and triethylamine (0.608 ml, 4.36 mmol) and was heated to 80° C. for 20 minutes. After cooling to room temperature, the reaction mixture was diluted with EtOAc, washed with 1N citric acid solution and the organics concentrated. Purification of the resulting residue by reverse phase column chromatography [RediSep Gold C18 150 g, 10 to 100% (0.1% NH$_4$OH in MeOH)/(0.1% NH$_4$OH in water)] gave tert-butyl 4-(2-(2-(N-(pyrazin-2-yl)sulfamoyl)-1,2,3,4-tetrahydroisoquinolin-5-yl)-5-(trifluoromethyl)phenyl)-5,6-dihydropyridine-1(2H)-carboxylate (0.180 g, 0.292 mmol). This material was taken up in 1 mL THF, was treated with HCl 4N in dioxane (0.109 ml, 0.436 mmol) and was heated to 80° C. for one hour. LC/MS showed exclusively product so the reaction mixture was concentrated. Purification of the resulting residue by reverse phase column chromatography [RediSep Gold C18 100 g, 10 to 100% (0.1% NH$_4$OH in MeOH)/(0.1% NH$_4$OH in water)] gave N-(pyrazin-2-yl)-5-(2-(1,2,3,6-tetrahydropyridin-4-yl)-4-(trifluoromethyl)phenyl)-3,4-dihydroisoquinoline-2(1H)-sulfonamide (0.113 g, 0.219 mmol). [M+H]$^+$=515.8 $^1$H NMR (400 MHz, DMSO-d$_6$) δ ppm: 8.25 (s, 1H), 7.94 (s, 1H), 7.71-7.78 (m, 2H), 7.50 (d, J=8.0 Hz, 1H), 7.43 (s, 1H), 7.16 (t, J=7.80 Hz, 1H), 7.09 (d, J=7.80 Hz, 1H), 7.00 (d, J=8.22 Hz, 1H), 5.67 (br. s., 1H), 4.24-4.42 (m, 2H), 3.48 (br. s., 2H), 3.30-3.39 (m, 1H), 3.19-3.29 (m, 1H), 2.91-3.01 (m, 1H), 2.78-2.86 (m, 1H), 2.45-2.52 (m, 1H), 2.29-2.36 (m, 1H), 1.81-2.08 (m, 2H)

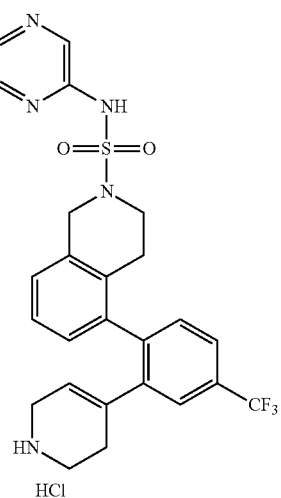

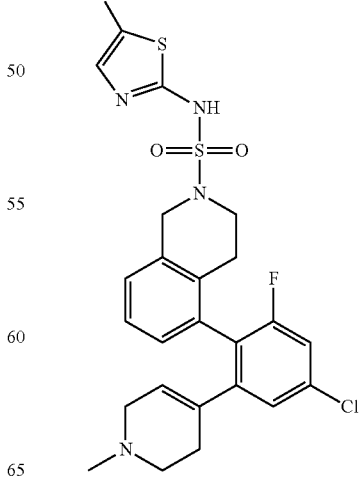

Example 54

5-(4-Chloro-2-fluoro-6-(1-methyl-1,2,3,6-tetrahydropyridin-4-yl)phenyl)-N-(5-fluorothiazol-2-yl)-3,4-dihydroisoquinoline-2(1H)-sulfonamide The title compound was prepared as Example 40 with the exception that 5-(2-bromo-4-chloro-6-fluorophenyl)-1,2,3,4-tetrahydroisoquinoline hydrochloride (Intermediate U) was used in Step 1 rather than 5-(2-bromo-5-(trifluoromethyl)phenyl)-1,2,3,4-tetrahydroisoquinoline hydrochloride. [M+H]$^+$=537.0 $^1$H NMR (400 MHz, Acetone-d$_6$) δ ppm: 7.30 (d, J=8.8 Hz, 1H), 7.16 (s, 1H), 7.03-7.13 (m, 2H), 6.94 (d, J=7.0 Hz, 1H), 6.65 (s, 1H), 5.85 (s, 1H), 4.50 (d, J=17.3 Hz, 1H), 4.22 (d, J=17.1 Hz, 1H), 3.62-3.81 (m, 2H), 3.11-3.36 (m, 4H), 2.73-2.91 (m, 2H), 2.53 (s, 3H), 2.08-2.15 (m, 2H)

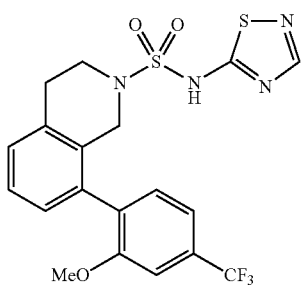 [SMILES: COc1cc(C(F)(F)F)ccc1-c1cccc2c1CN(S(=O)(=O)Nc1ncns1)CC2]

Example 55

8-(2-Methoxy-4-(trifluoromethyl)phenyl)-N-(1,2,4-thiadiazol-5-yl)-3,4-dihydroisoquinoline-2(1H)-sulfonamide The title compound was prepared in a manner analogous to Example 32, except that 8-(2-methoxy-4-(trifluoromethyl)phenyl)-1,2,3,4-tetrahydroisoquinoline (Intermediate Y) was used in place of 8-(2-(1H-imidazol-1-yl)-4-(trifluoromethyl)phenyl)-1,2,3,4-tetrahydroisoquinoline [M+H]$^+$=471.0 $^1$H NMR (400 MHz, Acetone-d$_6$) δ ppm: 8.16 (s, 1H), 7.32-7.38 (m, 2H), 7.16-7.29 (m, 3H), 7.01 (d, J=7.3 Hz, 1H), 3.86-4.13 (m, 2H), 3.81 (s, 3H), 3.34-3.48 (m, 2H), 2.96-3.06 (m, 2H)

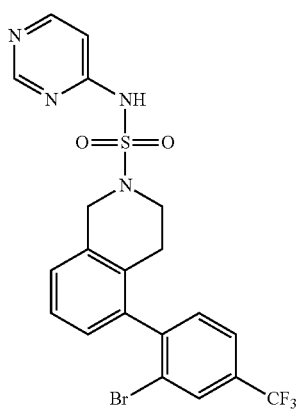 [SMILES: O=S(=O)(Nc1ccncn1)N1CCc2c(cccc2-c2ccc(C(F)(F)F)cc2Br)C1]

Example 56

5-(2-Bromo-4-(trifluoromethyl)phenyl)-N-(pyrimidin-4-yl)-3,4-dihydroisoquinoline-2(1H)-sulfonamide A 15-mL round-bottom flask was charged with 5-(2-bromo-4-(trifluoromethyl)phenyl)-1,2,3,4-tetrahydroisoquinoline hydrochloride (Intermediate D, 287.2 mg, 0.731 mmol) and triethylamine (224 μl, 1.609 mmol) in DCM (3.8 mL) to give a brown solution. The flask was cooled in an ice-bath for 10 min, then sulfuryl chloride (125 μl, 1.536 mmol) was added dropwise. Stirring was continued for 2 hours at which time the mixture was quenched with water, then extracted with DCM (3×). The combined organic extracts were dried over sodium sulfate, filtered, and concentrated. The residue was chromatographed on a 40 g silica gel column with 0 to 40% EtOAc/Heptane to give 5-(2-bromo-4-(trifluoromethyl)phenyl)-3,4-dihydroisoquinoline-2(1H)-sulfonyl chloride (253.01 mg, 0.556 mmol) as a clear, very viscous oil that was immediately used in the next step. A vial was charged with 5-(2-bromo-4-(trifluoromethyl)phenyl)-3,4-dihydroisoquinoline-2(1H)-sulfonyl chloride (40.045 mg, 0.088 mmol), pyrimidin-4-amine (41.9 mg, 0.440 mmol), chloroform (587 μl), and pyridine (71.2 μl, 0.881 mmol) and was placed into a 50° C. bath. The mixture was heated overnight before being allowed to cool to rt. The mixture was concentrated under a vacuum, and the residue was chromatographed on a 12 g silica gel column with 0 to 6% MeOH/DCM to give 5-(2-bromo-4-(trifluoromethyl)phenyl)-N-(pyrimidin-4-yl)-3,4-dihydroisoquinoline-2(1H)-sulfonamide (29.77 mg, 0.058 mmol) as a yellow solid. [M+H]$^+$=513.0. $^1$H NMR (400 MHz, DMSO-d$_6$) δ ppm=9.55 (br. s., 1H), 9.07 (br. s., 1H), 8.57 (br. s., 1H), 8.13 (d, J=1.3 Hz, 1H), 7.99 (br. s., 1H), 7.83 (dd, J=1.1, 8.0 Hz, 1H), 7.55-7.44 (m, 1H), 7.35-7.21 (m, 2H), 7.02 (dd, J=2.0, 6.8 Hz, 1H), 4.71 (d, J=6.4 Hz, 1H), 4.32-4.17 (m, 2H), 3.24-3.07 (m, 2H), 2.45 (br. s., 2H).

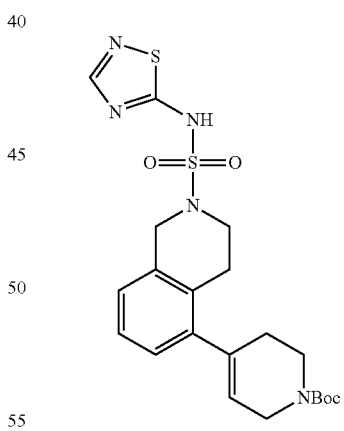

Example 57 tert-Butyl 4-(2-(N-(1,2,4-thiadiazol-5-yl)sulfamoyl)-1,2,3,4-tetrahydroisoquinolin-5-yl)-5,6-dihydropyridine-1(2H)-carboxylate The title compound was prepared in a manner analogous to Example 7 employing (1-(tert-butoxycarbonyl)-1,2,3,6-tetrahydropyridin-4-yl)boronic acid instead of (4-(trifluoromethyl)phenyl)boronic acid. [M+H]$^+$=NA (did not ionize of instrument)$^1$H NMR (400 MHz, Acetone-$d_6$) δ ppm: 8.23-8.27 (m, 1H), 7.11-7.19 (m, 1H), 7.05 (d, J=7.5 Hz, 1H), 6.99 (d, J=8.1 Hz, 1H), 5.59 (s, 1H), 4.32 (s, 2H), 4.01 (br. s., 2H), 3.60 (br. s., 2H), 3.37 (m, 2H), 2.85-2.91 (m, 3H), 2.32 (br. s., 2H), 1.44-1.50 (m, 9H)

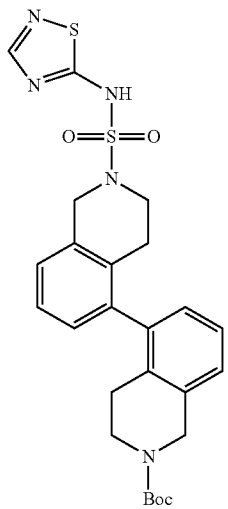 [SMILES: CC(C)(C)OC(=O)N1CCc2c(cccc2-c2cccc3c2CCN(S(=O)(=O)Nc2ncns2)C3)C1]

Example 58 tert-Butyl 2'-(N-(1,2,4-thiadiazol-5-yl)sulfamoyl)-1',2',3,3',4,4'-hexahydro-[5,5'-biisoquinoline]-2(1H)-carboxylate The title compound was prepared in a manner analogous to Example 7 using tert-butyl 5-(4,4,5,5-tetramethyl-1,3,2-dioxaborolan-2-yl)-3,4-dihydroisoquinoline-2(1H)-carboxylate (ASW Medchem, Brunswick, N.J.) instead of (4-(trifluoromethyl)phenyl)boronic acid. [M+H]$^+$=528.1 $^1$H NMR (400 MHz, Acetone-$d_6$) δ ppm: 8.24-8.29 (m, 1H), 7.23-7.29 (m, 2H), 7.13-7.22 (m, 2H), 6.98 (d, J=7.1 Hz, 2H), 4.61 (s, 2H), 4.39 (s, 2H), 3.52-3.61 (m, 1H), 3.38-3.51 (m, 1H), 3.28-3.37 (m, 2H), 2.55-2.61 (m, 1H), 2.25-2.51 (m, 3H), 1.45 (s, 9H)

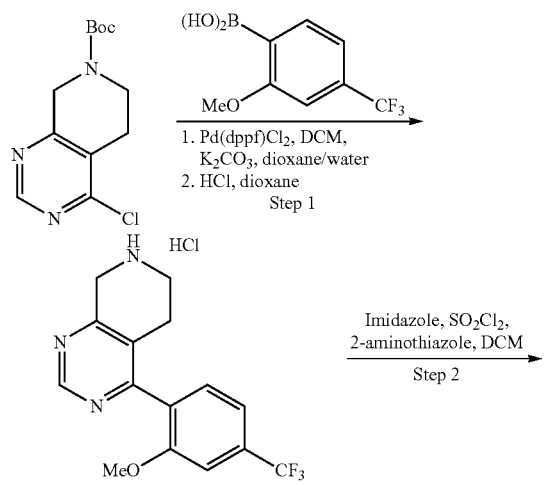

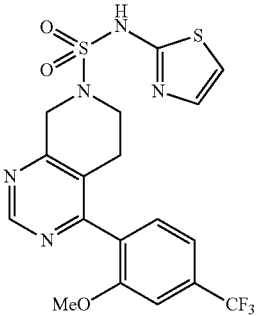

Example 59

4-(2-methoxy-4-(trifluoromethyl)phenyl)-N-(thiazol-2-yl)-5,6-dihydropyrido[3,4-d]pyrimidine-7(8H)-sulfonamide Step 1: 4-(2-methoxy-4-(trifluoromethyl)phenyl)-5,6,7,8-tetrahydropyrido[3,4-d]pyrimidine hydrochloride A solution of PdCl$_2$(dppf)-CH$_2$Cl$_2$ adduct (0.091 g, 0.111 mmol), (2-methoxy-4-(trifluoromethyl)phenyl)boronic acid (0.815 g, 3.71 mmol), tert-butyl 4-chloro-5,6-dihydropyrido[3,4-d]pyrimidine-7(8H)-carboxylate (1.000 g, 3.71 mmol), and potassium carbonate (2.050 g, 14.83 mmol) in 12 mL of dioxane and 4 mL water was heated to 110° C. for one hour. The reaction mixture was then diluted with DCM, the organics were dried over MgSO$_4$ and concentrated. The crude residue was treated with HCl (4N in dioxane) (9.27 ml, 37.1 mmol) and was allowed to stir at room temperature overnight. The reaction mixture was diluted with ether, and the resulting solids were filtered off and dried yielding 4-(2-methoxy-4-(trifluoromethyl)phenyl)-5,6,7,8-tetrahydropyrido[3,4-d]pyrimidine hydrochloride (1.333 g, 3.86 mmol, 104% yield) as a gray solid with minor impurities. (M+H)$^+$=310.2.

Step 2: 4-(2-methoxy-4-(trifluoromethyl)phenyl)-N-(thiazol-2-yl)-5,6-dihydropyrido[3,4-d]pyrimidine-7(8H)-sulfonamide A solution of thiazol-2-amine (0.097 g, 0.970 mmol) and imidazole (0.198 g, 2.91 mmol) in 4 mL of DCM was cooled to −78° C. Sulfuryl chloride (0.079 ml, 0.970 mmol) was added, the cooling bath was removed, and the reaction mixture was allowed to stir for an additional 30 minutes. 4-(2-methoxy-4-(trifluoromethyl)phenyl)-5,6,7,8-tetrahydropyrido[3,4-d]pyrimidine hydrochloride (0.150 g, 0.485 mmol) was added, followed by n,n-diisopropylethylamine (0.847 ml, 4.85 mmol), and the reaction mixture was heated to reflux for one hour, after which time the reaction was concentrated. Purification of the crude residue by reverse phase column chromatography [Puriflash C18, 30µ 55 g, 10-100% (0.1% NH4OH in MeOH)/(0.1% NH4OH in water)] gave 4-(2-methoxy-4-(trifluoromethyl)phenyl)-N-(thiazol-2-yl)-5,6-dihydropyrido[3,4-d]pyrimidine-7(8H)-sulfonamide (0.138 g, 0.293 mmol, 60.4% yield). $^1$H NMR (MeCN-$d_3$) δ: 8.96 (s, 1H), 7.33-7.42 (m, 3H), 6.93 (d, J=4.8 Hz, 1H), 6.55 (d, J=4.8 Hz, 1H), 4.35 (br. s., 2H), 3.79-3.87 (m, 3H), 3.08-3.53 (m, 2H), 2.39-2.89 (m, 1H); (M+H)+=472.0.

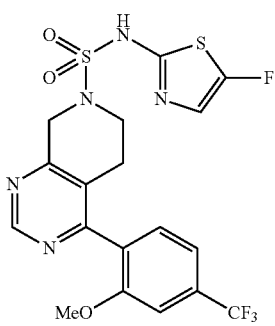 [SMILES: COc1cc(C(F)(F)F)ccc1-c1ncnc2c1CCN(S(=O)(=O)Nc1ncc(F)s1)C2]

Example 60

N-(5-fluorothiazol-2-yl)-4-(2-methoxy-4-(trifluoromethyl)phenyl)-5,6-dihydropyrido[3,4-d]pyrimidine-7(8H)-sulfonamide This compound was prepared in an analogous manner to example 59, using 2-amino-5-fluorothiazole hydrochloride instead of 2-aminothiazole in Step 2. $^1$H NMR (MeCN-$d_3$) δ: 8.94-9.00 (m, 1H), 7.34-7.42 (m, 3H), 6.75 (s, 1H), 4.35 (br. s., 2H), 3.77-3.87 (m, 3H), 3.18-3.47 (m, 2H), 2.40-2.89 (m, 2H); (M+H)$^+$=490.0.

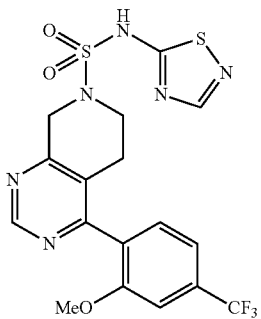 [SMILES: COc1cc(C(F)(F)F)ccc1-c1ncnc2c1CCN(S(=O)(=O)Nc1ncns1)C2]

Example 61

4-(2-methoxy-4-(trifluoromethyl)phenyl)-N-(1,2,4-thiadiazol-5-yl)-5,6-dihydropyrido[3,4-d]pyrimidine-7(8H)-sulfonamide This compound was prepared in an analogous manner to example 59, using 5-amino-1,2,4-thiadiazole instead of 2-aminothiazole, and triethylamine instead of imidazole in step 2. $^1$HNMR (MeCN-d3) δ: 8.95 (s, 1H), 7.85-7.92 (m, 1H), 7.32-7.43 (m, 3H), 4.32 (br. s., 2H), 3.77-3.86 (m, 3H), 3.20-3.46 (m, 2H), 2.33-2.81 (m, 2H); (M+H)$^+$=473.0.

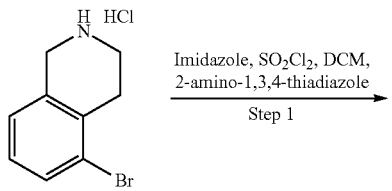

Imidazole, SO$_2$Cl$_2$, DCM,
2-amino-1,3,4-thiadiazole
———————————→
Step 1

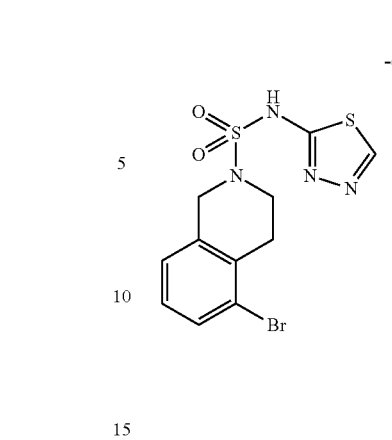

1. 4-chloro-2-methoxyphenylboronic acid, Pd(Amphos)$_2$Cl$_2$, K$_3$PO$_4$, dioxane/water
2. 3,4-difluorophenylboronic acid, Pd(Amphos)$_2$Cl$_2$, K$_3$PO$_4$, dioxane/water
———————————→
Step 2

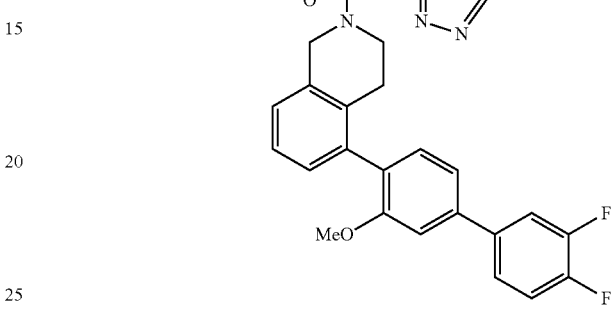

Example 62

5-(3',4'-difluoro-3-methoxy-[1,1'-biphenyl]-4-yl)-N-(1,3,4-thiadiazol-2-yl)-3,4-dihydroisoquinoline-2(1H)-sulfonamide Step 1: 5-bromo-N-(1,3,4-thiadiazol-2-yl)-3,4-dihydroisoquinoline-2(1H)-sulfonamide A solution of 1,1''-sulfonyldiimidazole (0.588 g, 2.97 mmol) and 1,3,4-thiadiazol-2-amine (0.300 g, 2.97 mmol) in 6 mL of DMF was cooled to 0° C. NaH (60% in mineral oil) (0.238 g, 9.91 mmol) was added. After 30 minutes, the reaction mixture was heated to 80° C. for one hour. 5-bromo-1,2,3,4-tetrahydroisoquinoline hydrochloride (0.737 g, 2.97 mmol) and n,n-diisopropylethylamine (2.59 ml, 14.83 mmol) were added, and the reaction mixture was heated to 110° C. for an additional 3 hours. The reaction mixture was then diluted with DCM and washed with 1N citric acid solution. The organics were dried over MgSO$_4$ and concentrated. Purification of the crude residue by reverse phase column chromatography [Redisep Gold C18, 10-100% (0.1% NH4OH in MeOH)/(0.1% NH4OH in water)] gave 5-bromo-N-(1,3,4-thiadiazol-2-yl)-3,4-dihydroisoquinoline-2(1H)-sulfonamide (0.520 g, 1.386 mmol, 46.7% yield). (M+H)$^+$=375.0.

Step 2: 5-(3',4'-difluoro-3-methoxy-[1,1'-biphenyl]-4-yl)-N-(1,3,4-thiadiazol-2-yl)-3,4-dihydroisoquinoline-2(1H)-sulfonamide A microwave vial charged with Pd(Amphos)$_2$Cl$_2$ (9.43 mg, 0.013 mmol), (4-chloro-2-methoxy)phenylboronic acid (0.050 g, 0.266 mmol), 5-bromo-N-(1,3,4-thiadiazol-2-yl)-3,4-dihydroisoquinoline-2(1H)-sulfonamide (0.100 g, 0.266 mmol), potassium phosphate (0.339 g, 1.599 mmol), 1.5 mL of dioxane and 0.25 mL of water was heated to 150° C. in the microwave for 30 minutes. (3,4-difluorophenyl)boronic acid (0.053 g, 0.333 mmol) and an additional portion of Pd(Amphos)$_2$Cl$_2$ (9.43 mg, 0.013 mmol) were added, and the reaction mixture was heated to 150° C. in the microwave for an additional 30 minutes. The aqueous layer was removed, and the reaction mixture was treated with HCl (4N in dioxane) (0.266 ml, 1.066 mmol). After stirring for 10 minutes, the reaction mixture was concentrated. Purification of the crude residue by reverse phase column chromatography [RediSep Gold C18, 10-100% (0.1% NH4OH in MeOH)/(0.1% NH4OH in water)] gave 5-(3',4'-difluoro-3-methoxy-[1,1'-biphenyl]-4-yl)-N-(1,3,4-thiadiazol-2-yl)-3,4-dihydroisoquinoline-2(1H)-sulfonamide (0.048 g, 0.093 mmol, 35.0% yield). $^1$H NMR (MeCN-d3) δ: 8.31 (s, 1H), 7.65 (ddd, J=12.2, 7.8, 2.2 Hz, 1H), 7.52 (dddt, J=7.1, 4.3, 2.7, 1.2 Hz, 1H), 7.37 (dt, J=10.6, 8.5 Hz, 1H), 7.14-7.27 (m, 4H), 7.07-7.12 (m, 1H), 6.99-7.05 (m, 1H), 4.20-4.41 (m, 2H), 3.81 (s, 3H), 3.30-3.39 (m, 1H), 3.12-3.24 (m, 1H), 2.63-2.76 (m, 1H), 2.42-2.55 (m, 1H); (M+H)$^+$=515.0.

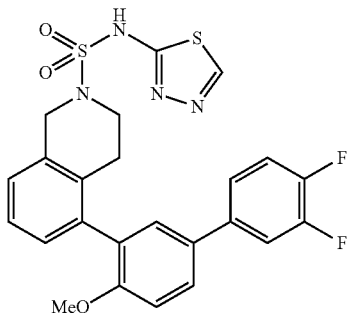 [SMILES: COc1ccc(-c2ccc(F)c(F)c2)cc1-c1cccc2c1CCN(S(=O)(=O)Nc1nncs1)C2]

Example 63

5-(3',4'-difluoro-4-methoxy-[1,1'-biphenyl]-3-yl)-N-(1,3,4-thiadiazol-2-yl)-3,4-dihydroisoquinoline-2(1H)-sulfonamide This compound was prepared in an analogous manner to example 62, using (5-chloro-2-methoxy)phenylboronic acid instead of (4-chloro-2-methoxy)phenylboronic acid in step 2. $^1$H NMR (MeCN-d3) δ: 8.30 (s, 1H), 7.62 (dd, J=8.6, 2.5 Hz, 1H), 7.54 (ddd, J=12.3, 7.7, 2.2 Hz, 1H), 7.42 (dddt, J=7.1, 4.3, 2.7, 1.2 Hz, 1H), 7.18-7.38 (m, 3H), 7.04-7.16 (m, 3H), 4.25-4.41 (m, 2H), 3.77 (s, 3H), 3.36 (dt, J=11.9, 5.9 Hz, 1H), 3.22 (ddd, J=12.2, 7.4, 5.1 Hz, 1H), 2.65-2.77 (m, 1H), 2.49-2.59 (m, 1H); (M+H)$^+$=515.0.

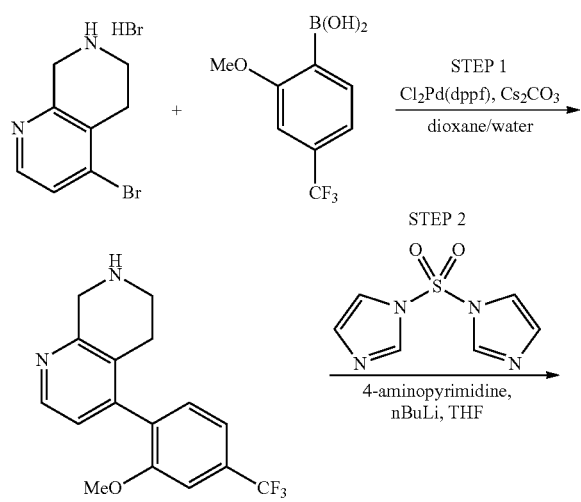

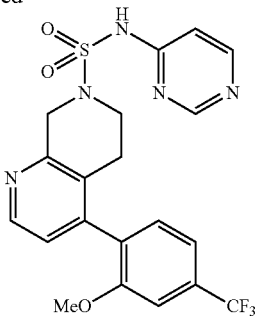

Example 64

4-(2-methoxy-4-(trifluoromethyl)phenyl)-N-4-pyrimidinyl-5,8-dihydro-1,7-naphthyridine-7(6H)-sulfonamide Step 1. 4-(2-methoxy-4-(trifluoromethyl)phenyl)-5,6,7,8-tetrahydro-1,7-naphthyridine A pressure vessel was charged with 4-bromo-5,6,7,8-tetrahydro-1,7-naphthyridine hydrobromide (331 mg, 1.126 mmol), 2-methoxy-4-(trifluoromethyl)phenylboronic acid (488 mg, 2.219 mmol), cesium carbonate, 99.9% (metal basis) (0.275 mL, 3.44 mmol), and dichloro 1,1'-bis(diphenylphosphino)ferrocene palladium (ii) dichloromethane adduct (86 mg, 0.105 mmol). Dioxane (2 mL) and water (0.4 mL) were added, and argon was streamed into the vessel for about 20 seconds. The mixture was stirred in a 70° C. oil bath for two hours, then diluted with CH$_2$Cl$_2$ and washed with H$_2$O. The layers were separated and the water layer was extracted with another portion of CH$_2$Cl$_2$. The combined organic layers were dried over Na$_2$SO$_4$ and concentrated. The residue was purified by column chromatography (Combiflash, 40 gram Redisep gold column), eluting with 0-100% (3:1 EtoAc/EtOH with 2% NH4OH in heptane) to obtain 4-(2-methoxy-4-(trifluoromethyl)phenyl)-5,6,7,8-tetrahydro-1,7-naphthyridine (232 mg, 0.753 mmol, 66.8% yield) as a brown viscous oil. [M+H]$^+$=309.0.

Step 2: 4-(2-methoxy-4-(trifluoromethyl)phenyl)-N-4-pyrimidinyl-5,8-dihydro-1,7-naphthyridine-7(6H)-sulfonamide 4-(2-Methoxy-4-(trifluoromethyl)phenyl)-N-4-pyrimidinyl-5,8-dihydro-1,7-naphthyridine-7(6H)-sulfonamide was prepared from 4-(2-methoxy-4-(trifluoromethyl)phenyl)-5,6,7,8-tetrahydro-1,7-naphthyridine by the Step 1 procedure of Example 37. $^1$H NMR (400 MHz, DMSO-d$_6$) δ ppm 3.53 (br. s., 4H) 3.78 (s, 3H) 4.57 (br. s., 2H) 6.98 (br. s., 1H) 7.09 (d, J=4.50 Hz, 1H) 7.29 (br. s., 1H) 7.40 (br. s., 2H) 8.32-8.48 (m, 2H) 8.53 (br. s., 1H); [M+H]$^+$=466.0.

Nav 1.7 and Nav 1.5 Ion Works Quattro (IWQ) In Vitro Assays 293 cells stably transfected with either Nav 1.7 or with Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the $26^{th}$ pulse to −20 mV was subtracted from the peak current evoked by the $26^{th}$ pulse to −20 mV to correct for leak current. Percent block was calculated for each concentration in duplicate, and $IC_{50}$ curves were fitted to percent block as a function of concentration. Data for compounds of the present invention are shown in the table below. It is noted that more than one experiment may have been conducted and the number presented may be the average of the results of more than one experiment.

Nav 1.7 In Vitro PatchExpress (PX) Assay 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and $IC_{50}$ curves were fitted to percent inhibition as a function of concentration.

| Example No. | Nav 1.7 (IWQ) $IC_{50}$ (µM) | Nav 1.5 (IWQ) $IC_{50}$ (µM) | Nav 1.7 PX $IC_{50}$ (µM) |
| --- | --- | --- | --- |
| 1 | 0.0363 | >10.0 | 0.12 |
| 2 | 0.217 | >10.0 | 0.64 |
| 3 | 0.414 | >10.0 | 2.01 |
| 4 | 0.527 | >10.0 | 0.56 |
| 5 | 1.03 | 5.63 | 1.7 |
| 6 | 0.0221 | >10.0 | 0.03 |
| 7 | 1.64 | >10.0 | 5.8 |
| 8 | 1.84 | >10.0 | 3.13 |
| 9 | 0.477 | >10.0 | 0.61 |
| 10 | 5.47 | >10.0 | 7.46 |
| 11 | 4.22 | >10.0 | 7.66 |
| 12 | 2.41 | >10.0 | 1.33 |
| 13 | 3.87 | >10.0 | >30.0 |
| 14 | 0.684 | >10.0 | 3.53 |
| 15 | 0.0783 | >10.0 | 0.09 |
| 16 | 2.66 | >10.0 | 5.42 |
| 17 | 0.157 | >10.0 | 0.35 |
| 18 | 0.0453 | >10.0 | 0.07 |
| 19 | 0.378 | >10.0 | 1.71 |
| 20 | 5.83 | >10.0 | |
| 21 | 1.8 | 4.08 | |
| 22 | 0.0805 | >10.0 | 0.47 |
| 23 | 0.186 | >10.0 | 0.8 |
| 24 | 2.68 | >10.0 | 4.91 |
| 25 | 6.9 | >10.0 | |
| 26 | 1.51 | >10.0 | 2.2 |
| 27 | 0.125 | >10.0 | 0.67 |
| 28 | 4.67 | >10.0 | >30.0 |
| 29 | 0.0628 | >10.0 | 0.37 |
| 30 | 0.137 | >10.0 | 0.56 |
| 31 | 0.758 | >10.0 | 1.74 |
| 32 | 0.0258 | 6.68 | 0.22 |
| 33 | 0.351 | >10.0 | 0.19 |
| 34 | 0.0645 | >10.0 | 0.05 |
| 35 | 0.315 | >10.0 | 0.17 |
| 36 | 1.89 | >10.0 | 4.68 |
| 37 | 3.94 | >10.0 | 19 |
| 38 | 0.0917 | >10.0 | 0.69 |
| 39 | 0.24 | >10.0 | 1.17 |
| 40 | 2.81 | >10.0 | 12.1 |
| 41 | 0.395 | >10.0 | 7.34 |
| 42 | 0.228 | >10.0 | 1.34 |
| 43 | 0.171 | >10.0 | 1.92 |
| 44 | 0.135 | >10.0 | 0.26 |
| 45 | 0.0675 | >10.0 | 0.87 |
| 46 | 0.019 | >10.0 | 0.94 |
| 47 | 0.059 | >10.0 | 0.56 |
| 48 | 4.1 | 7.26 | 6.11 |
| 49 | 12.71 | >10.0 | 14.6 |
| 50 | 7.6 | >10.0 | |
| 51 | 19.07 | >10.0 | |
| 52 | 23* | >10.0 | |
| 53 | 10.49 | >10.0 | |
| 54 | 14.89 | >10.0 | |
| 55 | 9.44 | >10.0 | |
| 56 | 38.9 | >10.0 | >10.0 |
| 57 | 7.1 | >10.0 | |
| 58 | 15.84 | >10.0 | 16.5 |
| 59 | 0.087 | >10.0 | 1.05 |
| 60 | | | 0.81 |
| 61 | 0.141 | >10.0 | 1.21 |
| 62 | | | 8.05 |
| 63 | | | 11.2 |
| 64 | | | 6.19 |

*percent inhibition at 4.9 µM

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 µL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula: (−(Individual score−Vehicle average score)/Vehicle average score))*100=% MPE Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

On the test day, animals (Naïve, male C57Bl/6 mice) weighing between 22-30 g at the start of testing were obtained from Harlan (Frederick, Md.). All animals are housed under a 12/12 h light/dark cycle with lights on at 0600. Rodents are housed up to four per cage on solid bottom cages with corn cob bedding and have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing, animals are acclimated to the individual testing chambers for 5 minutes immediately preceding the test. At test time, each animal is gently wrapped in a glove with the left hind paw exposed. A dilute solution of formalin (2.0%) in phosphate buffered saline is injected subcutaneously into the dorsal surface of the left hindpaw in a volume to 20 µL with a 30 g needle. Animals are then placed into the testing chambers and the time the animal spends licking and/or lifting the hind paw is recorded for up to one hour. Individual data can be expressed as a % reversal calculated with the following formula: (1−(Drug group average score−Vehicle group average score))*100=% Reversal Statistical analysis is performed by analysis of variance (ANOVA), with post-hoc analysis using Dunett's multiple comparison test compared to the vehicle group for any significant main effect. Data can be represented as mean+/−standard error for each group.

CFA-Thermal Assay

Animals (Naïve, male Sprague Dawley rats) weighing between 260-300 g at the start of testing can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then returned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

What is claimed is:

1. A compound of Formula I, or a pharmaceutically acceptable salt thereof,

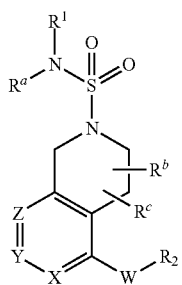

I wherein:
- $R^1$ is a five to six membered heteroaryl group, where the heteroaryl group can have from one to three heteroatoms independently selected from O, N or S, and can be unsubstituted or substituted with from 1 to 3 substituents independently selected from halo, $C_{1-6}$alkyl, —CN, —CF$_3$, —OH, —OCF$_3$, —OC$_{1-6}$alkyl, —COO or —(CH$_2$)—NR$^e$R$^e$;
- $R^2$ is a three to ten membered cycloalkyl, six to ten membered aryl, five to ten membered heteroaryl or three to ten membered heterocycloalkyl group, where the heteroaryl or heterocycloalkyl group can have from one to three heteroatoms independently selected from O, N or S, and where the cycloalkyl, aryl, heteroaryl or heterocycloalkyl group can be unsubstituted or substituted with from 1 to 3 substituents independently selected from an A group, halo, —N$_3$, —CF$_3$, —OH, —OCF$_3$, $C_{1-6}$alkyl, —OC$_{1-6}$alkyl, —CN, —(CH$_2$)$_n$NR$^e$R$^e$, —O(CH$_2$)$_m$OR$^e$, —CO$_2$R$^e$, —SR$_e$, —S(=O)$_2$R$^e$ or —NR$^e$(CH$_2$)$_m$OR$^e$;
- A is a three to ten membered cycloalkyl, six to ten membered aryl, five to ten membered heteroaryl or three to ten membered heterocycloalkyl group, where the heteroaryl or heterocycloalkyl group can have from one to three heteroatoms independently selected from O, N or S, and where the cycloalkyl, aryl, heteroaryl or heterocycloalkyl group can be unsubstituted or substituted with from 1 to 3 substituents independently selected from halo, $C_{1-6}$alkyl, —CN, —CF$_3$, —OH, —OCF$_3$, —OC$_{1-6}$alkyl, —CO$_2$R$^e$ or —(CH$_2$)—NR$^e$R$^e$;
- $R^a$ is hydrogen, $C_{1-6}$alkyl or a three to ten membered cycloalkyl group, where the cycloalkyl group may be unsubstituted or substituted with from 1 to 3 substitutents independently selected from halo, $C_{1-6}$alkyl, —CN, —CF$_3$, —OH, —OCF$_3$, —OC$_2$R$^e$ or —OC$_{1-6}$alkyl;
- $R^b$ is hydrogen, halo, —CN, —OC$_{1-6}$alkyl, $C_{1-6}$alkyl, —CF$_3$, —OH, —CF$_2$H, —OCF$_3$, —OCF$_2$H, —OC$_2$R$^e$, —(=O) or —OCFH$_2$;
- $R^c$ is hydrogen, halo, —CN, —OC$_{1-6}$alkyl, $C_{1-6}$alkyl, —CF$_3$, —OH, —CF$_2$H, —OCF$_3$, —OCF$_2$H, —CO$_2$R$^e$ or —OCFH$_2$;
- W is a bond;
- X is CR$^d$ or N;
- Y is CR$^d$ or N;
- Z is CR$^d$ or N;
- each R$^d$ is independently selected from hydrogen, halo, —CN, —OC$_{1-6}$alkyl, $C_{1-6}$alkyl, —CF$_3$, —OH, —CF$_2$H, —OCF$_3$, —OCF$_2$H, —CO$_2$R$^e$ or —OCFH$_2$;
- each n is independently 0 to 3;
- each m is independently 1 to 3; and
- each R$^e$ is independently hydrogen or $C_{1-6}$alkyl,
- provided that the compound of Formula I is not
  5-(2-(1,2,3,6-tetrahydropyridin-4-yl)-4-(trifluoromethyl)phenyl)-N-(1,3,4-thiadiazol-2-yl)-3,4-dihydroisoquinoline-2(1H)-sulfonamide or
  5-(1,2,3,6-tetrahydropyridin-4-yl)-N-(1,2,4-thiadiazol-5-yl)-3,4-dihydroisoquinoline-2(1H)-sulfonamide.

2. A compound in accordance with claim 1, or a pharmaceutically acceptable salt thereof, wherein $R^1$ is a five or six membered substituted or unsubstituted heteroaryl group.

3. A compound in accordance with claim 1, or a pharmaceutically acceptable salt thereof, wherein $R^1$ is a five membered substituted or unsubstituted heteroaryl group.

4. A compound in accordance with claim 1, or a pharmaceutically acceptable salt thereof, wherein $R^1$ is selected from substituted or unsubstituted thiadiazolyl, thiazolyl, pyrimidinyl or pyrazinyl.

5. A compound in accordance with claim 1, or a pharmaceutically acceptable salt thereof, wherein $R^1$ is selected from substituted or unsubstituted thiadiazolyl.

6. A compound in accordance with claim 1, or a pharmaceutically acceptable salt thereof, wherein $R^a$ is hydrogen.

7. A compound in accordance with claim 1, or a pharmaceutically acceptable salt thereof, wherein $R^b$ is hydrogen.

8. A compound in accordance with claim 1, or a pharmaceutically acceptable salt thereof, wherein $R^c$ is hydrogen.

9. A compound in accordance with claim 1, or a pharmaceutically acceptable salt thereof, wherein X, Y and Z are CH.

10. A compound in accordance with claim 1, or a pharmaceutically acceptable salt thereof, wherein X is N, and Y and Z are CH.

11. A compound in accordance with claim 1, or a pharmaceutically acceptable salt thereof, wherein $R^2$ is a six to ten membered aryl group, six to ten membered heterocycloalkyl group or five to ten membered heteroaryl group, which group can be substituted or unsubstituted.

12. A compound in accordance with claim 11, or a pharmaceutically acceptable salt thereof, wherein $R^2$ is a substituted or unsubstituted six membered aryl group.

13. A compound in accordance with claim 12, or a pharmaceutically acceptable salt thereof, wherein $R^2$ is phenyl substituted with from 1 to 3 substituents independently selected from an A group, halo, —$N_3$, —$CF_3$, —OH, —$OCF_3$, $C_{1-6}$alkyl, —$OC_{1-6}$alkyl, —CN, —$(CH_2)$—$NR^eR^e$, —$O(CH_2)_mOR^e$, —COO, —$SR^e$, —$S(=O)_2R^e$ or —$NR^e(CH_2)_mOR^e$.

14. A compound in accordance with claim 12, or a pharmaceutically acceptable salt thereof, wherein $R^2$ is selected from phenyl, tetrahydroisoquinolinyl, isoquinolinyl, naphthalenyl, quinolinyl, indazolyl, pyridyl or dihydropyridyl substituted with from one to three substituents independently selected from an A group or substituted A group, halo, —$CF_3$, —$OC_{1-6}$alkyl, cyclopropyl, or —$CO_2C_{1-6}$alkyl.

15. A compound in accordance with claim 13, or a pharmaceutically acceptable salt thereof, wherein $R^2$ is

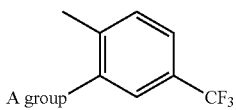

and the A group can be substituted or unsubstituted.

16. A compound in accordance with claim 13, or a pharmaceutically acceptable salt thereof, wherein $R^2$

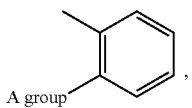

which can have up to two additional substitutents, and the A group can be substituted or unsubstituted.

17. A compound, or a pharmaceutically acceptable salt thereof, selected from:
5-(2-(1-methyl-1H-pyrazol-5-yl)-4-(trifluoromethyl)phenyl)-N-(1,2,4-thiadiazol-5-yl)-3,4-dihydroisoquinoline-2(1H)-sulfonamide;
5-(2-(pyridin-4-yl)-4-(trifluoromethyl)phenyl)-N-(1,2,4-thiadiazol-5-yl)-3,4-dihydroisoquinoline-2(1H)-sulfonamide;
5-(2-bromo-4-(trifluoromethyl)phenyl)-N-(thiazol-2-yl)-3,4-dihydroisoquinoline-2(1H)-sulfonamide;
5-(2-bromo-4-(trifluoromethyl)phenyl)-N-(1,2,4-thiadiazol-5-yl)-3,4-dihydroisoquinoline-2(1H)-sulfonamide;
tert-butyl 4-(2-(2-(N-(1,2,4-thiadiazol-5-yl)sulfamoyl)-1,2,3,4-tetrahydroisoquinolin-5-yl)-5-(trifluoromethyl)phenyl)-5,6-dihydropyridine-1(2H)-carboxylate;
5-(2-(1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide;
N-(1,2,4-thiadiazol-5-yl)-5-(4-(trifluoromethyl)phenyl)-3,4-dihydroisoquinoline-2(1H)-sulfonamide;
5-(2-fluoro-4-(trifluoromethyl)phenyl)-N-(1,2,4-thiadiazol-5-yl)-3,4-dihydroisoquinoline-2(1H)-sulfonamide;
5-(2-chloro-4-(trifluoromethyl)phenyl)-N-(1,2,4-thiadiazol-5-yl)-3,4-dihydroisoquinoline-2(1H)-sulfonamide;
5-(2-chloro-4-(trifluoromethyl)phenyl)-N-(1,2,4-thiadiazol-5-yl)-3,4-dihydroisoquinoline-2(1H)-sulfonamide;
5-(4-chloro-2-fluorophenyl)-N-(1,2,4-thiadiazol-5-yl)-3,4-dihydroisoquinoline-2(1H)-sulfonamide;
5-(2,4-dichlorophenyl)-N-(1,2,4-thiadiazol-5-yl)-3,4-dihydroisoquinoline-2(1H)-sulfonamide;
N-(1,2,4-thiadiazol-5-yl)-1',2',3,3',4,4'-hexahydro-[5,5'-biisoquinoline]-2(1H)-sulfonamide;
4-(2-(2-(N-(1,2,4-thiadiazol-5-yl)sulfamoyl)-1,2,3,4-tetrahydroisoquinolin-5-yl)-5-(trifluoromethyl)phenyl)-1,1-dimethyl-1,2,3,6-tetrahydropyridin-1-ium hydroxide;
5-(2-(1-methyl-1,2,3,6-tetrahydropyridin-4-yl)-4-(trifluoromethyl)phenyl)-N-(1,2,4-thiadiazol-5-yl)-3,4-dihydroisoquinoline-2(1H)-sulfonamide;
5-(2-(1-methyl-1H-pyrazol-4-yl)-4-(trifluoromethyl)phenyl)-N-(1,2,4-thiadiazol-5-yl)-3,4-dihydroisoquinoline-2(1H)-sulfonamide;
5-(2-(1H-pyrazol-4-yl)-4-(trifluoromethyl)phenyl)-N-(1,2,4-thiadiazol-5-yl)-3,4-dihydroisoquinoline-2(1H)-sulfonamide;
5-(2-(2-aminopyridin-4-yl)-4-(trifluoromethyl)phenyl)-N-(1,2,4-thiadiazol-5-yl)-3,4-dihydroisoquinoline-2(1H)-sulfonamide;
5-(2-(3,6-dihydro-2H-pyran-4-yl)-4-(trifluoromethyl)phenyl)-N-(1,2,4-thiadiazol-5-yl)-3,4-dihydroisoquinoline-2(1H)-sulfonamide;
5-(2-(5-methoxypyridin-3-yl)-4-(trifluoromethyl)phenyl)-N-(1,2,4-thiadiazol-5-yl)-3,4-dihydroisoquinoline-2(1H)-sulfonamide;
5-(2-(5-methylpyridin-3-yl)-4-(trifluoromethyl)phenyl)-N-(1,2,4-thiadiazol-5-yl)-3,4-dihydroisoquinoline-2(1H)-sulfonamide;
5-(2-(pyridin-3-yl)-4-(trifluoromethyl)phenyl)-N-(1,2,4-thiadiazol-5-yl)-3,4-dihydroisoquinoline-2(1H)-sulfonamide;
5-(2-(pyrimidin-5-yl)-4-(trifluoromethyl)phenyl)-N-(1,2,4-thiadiazol-5-yl)-3,4-dihydroisoquinoline-2(1H)-sulfonamide;
5-(naphthalen-1-yl)-N-(1,2,4-thiadiazol-5-yl)-3,4-dihydroisoquinoline-2(1H)-sulfonamide;
N-(1,2,4-thiadiazol-5-yl)-3',4'-dihydro-[4,5'-biisoquinoline]-2'(1'H)-sulfonamide;
5-(2,4-dimethoxyphenyl)-N-(1,2,4-thiadiazol-5-yl)-3,4-dihydroisoquinoline-2(1H)-sulfonamide;
5-(2,5-dimethoxyphenyl)-N-(1,2,4-thiadiazol-5-yl)-3,4-dihydroisoquinoline-2(1H)-sulfonamide;
5-(2,6-dimethoxyphenyl)-N-(1,2,4-thiadiazol-5-yl)-3,4-dihydroisoquinoline-2(1H)-sulfonamide;
5-(5-fluoro-2-methoxyphenyl)-N-(1,2,4-thiadiazol-5-yl)-3,4-dihydroisoquinoline-2(1H)-sulfonamide;
5-(4-fluoro-2-methoxyphenyl)-N-(1,2,4-thiadiazol-5-yl)-3,4-dihydroisoquinoline-2(1H)-sulfonamide;
5-(2-morpholino-4-(trifluoromethyl)phenyl)-N-(1,2,4-thiadiazol-5-yl)-3,4-dihydroisoquinoline-2(1H)-sulfonamide;
5-(2-(1H-imidazol-1-yl)-4-(trifluoromethyl)phenyl)-N-(1,2,4-thiadiazol-5-yl)-3,4-dihydroisoquinoline-2(1H)-sulfonamide;
N-(5-fluorothiazol-2-yl)-5-(2-(1,2,3,6-tetrahydropyridin-4-yl)-4-(trifluoromethyl)phenyl)-3,4-dihydroisoquinoline-2(1H)-sulfonamide;
5-(2-(2,5-dihydro-1H-pyrrol-3-yl)-4-(trifluoromethyl)phenyl)-N-(1,2,4-thiadiazol-5-yl)-3,4-dihydroisoquinoline-2(1H)-sulfonamide;
N-(5-fluorothiazol-2-yl)-5-(2-(piperidin-4-yl)-4-(trifluoromethyl)phenyl)-3,4-dihydroisoquinoline-2(1H)-sulfonamide;
5-(2-(1,2,3,6-tetrahydropyridin-4-yl)-4-(trifluoromethyl)phenyl)-N-(thiazol-2-yl)-3,4-dihydroisoquinoline-2(1H)-sulfonamide;
N-(pyrimidin-4-yl)-5-(2-(1,2,3,6-tetrahydropyridin-4-yl)-4-(trifluoromethyl)phenyl)-3,4-dihydroisoquinoline-2(1H)-sulfonamide;

5-(2-(1H-imidazol-1-yl)-4-(trifluoromethyl)phenyl)-N-(5-fluorothiazol-2-yl)-3,4-dihydroisoquinoline-2(1H)-sulfonamide;

N-(5-fluorothiazol-2-yl)-5-(2-(1-methyl-1,2,3,6-tetrahydropyridin-4-yl)-4-(trifluoromethyl)phenyl)-3,4-dihydroisoquinoline-2(1H)-sulfonamide;

N-(5-fluorothiazol-2-yl)-5-(2-(1-methyl-1,2,3,6-tetrahydropyridin-4-yl)-5-(trifluoromethyl)phenyl)-3,4-dihydroisoquinoline-2(1H)-sulfonamide;

N-(5-fluorothiazol-2-yl)-5-(2-(4-methylpiperazin-1-yl)-4-(trifluoromethyl)phenyl)-3,4-dihydroisoquinoline-2(1H)-sulfonamide;

N-(5-fluorothiazol-2-yl)-5-(2-(4-methylpiperazin-1-yl)-4-(trifluoromethyl)phenyl)-3,4-dihydroisoquinoline-2(1H)-sulfonamide;

N-(5-fluorothiazol-2-yl)-5-(2-(5-methyl-1H-imidazol-1-yl)-4-(trifluoromethyl)phenyl)-3,4-dihydroisoquinoline-2(1H)-sulfonamide;

5-(2-methoxy-4-(trifluoromethyl)phenyl)-N-(1,2,4-thiadiazol-5-yl)-3,4-dihydroisoquinoline-2(1H)-sulfonamide;

5-(4-cyclopropyl-2-methoxyphenyl)-N-(1,2,4-thiadiazol-5-yl)-3,4-dihydroisoquinoline-2(1H)-sulfonamide;

5-(2-methoxy-4-(trifluoromethyl)phenyl)-N-(1,2,4-thiadiazol-5-yl)-3,4-dihydro-2,6-naphthyridine-2(1H)-sulfonamide;

5-(4-cyclopropyl-2-methoxyphenyl)-N-(1,2,4-thiadiazol-5-yl)-3,4-dihydro-2,6-naphthyridine-2(1H)-sulfonamide;

5-(2-methoxy-4-(trifluoromethyl)phenyl)-4-methyl-N-(1,2,4-thiadiazol-5-yl)-3,4-dihydroisoquinoline-2(1H)-sulfonamide;

5-(2-(1-methyl-1H-pyrazol-5-yl)-4-(trifluoromethyl)phenyl)-N-(pyrimidin-2-yl)-3,4-dihydroisoquinoline-2(1H)-sulfonamide;

5-(2-methoxypyridin-3-yl)-N-(1,2,4-thiadiazol-5-yl)-3,4-dihydroisoquinoline-2(1H)-sulfonamide;

5-(1H-indazol-4-yl)-N-(1,2,4-thiadiazol-5-yl)-3,4-dihydroisoquinoline-2(1H)-sulfonamide;

7-chloro-N-(1,2,4-thiadiazol-5-yl)-3',4'-dihydro-[4,5'-biisoquinoline]-2'(1'H)-sulfonamide;

N-(pyrazin-2-yl)-5-(2-(1,2,3,6-tetrahydropyridin-4-yl)-4-(trifluoromethyl)phenyl)-3,4-dihydroisoquinoline-2(1H)-sulfonamide;

5-(4-chloro-2-fluoro-6-(1-methyl-1,2,3,6-tetrahydropyridin-4-yl)phenyl)-N-(5-fluorothiazol-2-yl)-3,4-dihydroisoquinoline-2(1H)-sulfonamide;

8-(2-methoxy-4-(trifluoromethyl)phenyl)-N-(1,2,4-thiadiazol-5-yl)-3,4-dihydroisoquinoline-2(1H)-sulfonamide;

5-(2-bromo-4-(trifluoromethyl)phenyl)-N-(pyrimidin-4-yl)-3,4-dihydroisoquinoline-2(1H)-sulfonamide;

tert-butyl 4-(2-(N-(1,2,4-thiadiazol-5-yl)sulfamoyl)-1,2,3,4-tetrahydroisoquinolin-5-yl)-5,6-dihydropyridine-1(2H)-carboxylate;

tert-butyl 2'-(N-(1,2,4-thiadiazol-5-yl)sulfamoyl)-1',2',3,3',4,4'-hexahydro-[5,5'-biisoquinoline]-2(1H)-carboxylate;

4-(2-methoxy-4-(trifluoromethyl)phenyl)-N-1,3-thiazol-2-yl-5,8-dihydropyrido[3,4-d]pyrimidine-7(6H)-sulfonamide;

N-(5-fluoro-1,3-thiazol-2-yl)-4-(2-methoxy-4-(trifluoromethyl)phenyl)-5,8-dihydropyrido[3,4-d]pyrimidine-7(6H)-sulfonamide;

4-(2-methoxy-4-(trifluoromethyl)phenyl)-N-1,2,4-thiadiazol-5-yl-5,8-dihydropyrido[3,4-d]pyrimidine-7(6H)-sulfonamide;

5-(3',4'-difluoro-3-methoxy-4-biphenylyl)-N-1,3,4-thiadiazol-2-yl-3,4-dihydro-2(1H)-isoquinolinesulfonamide;

5-(3',4'-difluoro-4-methoxy-3-biphenylyl)-N-1,3,4-thiadiazol-2-yl-3,4-dihydro-2(1H)-isoquinolinesulfonamide, or 4-(2-methoxy-4-(trifluoromethyl)phenyl)-N-4-pyrimidinyl-5,8-dihydro-1,7-naphthyridine-7(6H)-sulfonamide.

18. A method of treating pain, the method comprising administering to a patient in need thereof a therapeutically effective amount of a compound in accordance with claim 1, or a pharmaceutically acceptable salt thereof.

19. The method of claim 18 wherein the treatment is for chronic pain, acute pain, neuropathic pain, pain associated with rheumatoid arthritis, pain associated with osteoarthritis or pain associated with cancer.

20. A pharmaceutical composition comprising a compound in accordance with claim 1, or a pharmaceutically acceptable salt thereof, and a pharmaceutically acceptable excipient.

* * * * *